(12) United States Patent
Reiter et al.

(10) Patent No.: US 9,695,410 B2
(45) Date of Patent: *Jul. 4, 2017

(54) ISOLATED HIGH AFFINITY ENTITIES WITH T-CELL RECEPTOR LIKE SPECIFICITY TOWARDS NATIVE COMPLEXES OF MHC CLASS II AND GLUTAMIC ACID DECARBOXYLASE (GAD) AUTOANTIGENIC PEPTIDES

(75) Inventors: Yoram Reiter, Haifa (IL); Rony Dahan, Mazkeret Batia (IL)

(73) Assignee: Technion Research & Development Foundation Limited, Haifa (IL)

( * ) Notice: Subject to any disclaimer, the term of this patent is extended or adjusted under 35 U.S.C. 154(b) by 217 days.

This patent is subject to a terminal disclaimer.

(21) Appl. No.: 13/810,266

(22) PCT Filed: Jul. 14, 2011

(86) PCT No.: PCT/IL2011/000564
§ 371 (c)(1),
(2), (4) Date: Jan. 15, 2013

(87) PCT Pub. No.: WO2012/007951
PCT Pub. Date: Jan. 19, 2012

(65) Prior Publication Data
US 2013/0115218 A1 May 9, 2013

Related U.S. Application Data

(60) Provisional application No. 61/364,443, filed on Jul. 15, 2010.

(51) Int. Cl.
| | | |
|---|---|---|
| *C12N 9/88* | (2006.01) | |
| *C07K 16/28* | (2006.01) | |
| *C07K 16/40* | (2006.01) | |
| *C12N 15/62* | (2006.01) | |

(52) U.S. Cl.
CPC ............ *C12N 9/88* (2013.01); *C07K 16/2833* (2013.01); *C07K 16/40* (2013.01); *C12N 15/62* (2013.01); *C07K 2317/21* (2013.01); *C07K 2317/32* (2013.01); *C07K 2317/35* (2013.01); *C07K 2317/55* (2013.01); *C07K 2317/76* (2013.01); *C07K 2319/32* (2013.01); *C07K 2319/40* (2013.01); *C07K 2319/73* (2013.01)

(58) Field of Classification Search
None
See application file for complete search history.

(56) References Cited

U.S. PATENT DOCUMENTS

| | | | |
|---|---|---|---|
| 6,060,309 A * | 5/2000 | Kindsvogel et al. | ......... 435/325 |
| 6,270,772 B1 | 8/2001 | Burrows et al. | |
| 6,815,171 B2 | 11/2004 | Burrows et al. | |
| 7,265,218 B2 | 9/2007 | Burrows et al. | |
| 2001/0010820 A1 | 8/2001 | Jacobs et al. | |
| 2002/0114816 A1 | 8/2002 | Endl et al. | |
| 2002/0150914 A1 | 10/2002 | Andersen et al. | |
| 2003/0166277 A1 | 9/2003 | Zauderer et al. | |
| 2004/0191260 A1 | 9/2004 | Reiter et al. | |
| 2005/0142142 A1 | 6/2005 | Burrows et al. | |
| 2009/0155292 A1 | 6/2009 | Santamaria et al. | |
| 2011/0008382 A1 | 1/2011 | Burrows et al. | |
| 2013/0189284 A1 | 7/2013 | Reiter et al. | |
| 2014/0170168 A1 | 6/2014 | Reiter et al. | |

FOREIGN PATENT DOCUMENTS

| | | |
|---|---|---|
| WO | WO 99/14236 | 3/1999 |
| WO | WO 02/14870 | 2/2002 |
| WO | WO 2004/007528 | 1/2004 |
| WO | WO 2005/044982 | 5/2005 |
| WO | WO 2006/007667 | 1/2006 |
| WO | WO 2006/102170 | 9/2006 |
| WO | WO 2012/007950 | 1/2012 |
| WO | WO 2012/007951 | 1/2012 |
| WO | WO 2012/056407 | 5/2012 |

OTHER PUBLICATIONS

Li et al. "Suppression of Ongoing T Cell-Mediated Autoimmunity by Peptide-MHC Class II Dimer Vaccination", The Journal of Immunology, XP055110282, 183(7): 4809-4816, Oct. 1, 2009.
Liu et al. "Detection of Glutamic Acid Decarboxylase-Activated T Cells With I—Ag7 Tetramers", Proc. Natl. Acad. Sci. USA, XP055110389, 97(26): 14596-14601, Dec. 19, 2000.
Adamus et al. "Treatment of Autoimmune Anterior Uveitis With Recombinant TCR Ligands", Investigate Ophthalmology & Visual Science, 47(6): 2555-2561, Jun. 2006.
Aharoni et al. "Immunomodulation of Experimental Allergic Encephalomyelitis by Antibodies to the Antigen-Ia Complex", Nature, XP002514757, 351(6322): 147-150, May 9, 1991. Abstract.
Bach et al. "High Affinity Presentation of An Autoantigenic Peptide in Type I Diabetes by An HLA Class II Protein Encoded in A Haplotype Protecting From Disease", Journal of Autoimmune, JAI, 10: 375-386, 1997.
Becker "Sensitization and Tolerization to Brain Antigens in Stroke", Neuroscience, 158(3): 1090-1097, Feb. 6, 2009.

(Continued)

*Primary Examiner* — Gerald R Ewoldt

(57) ABSTRACT

Provided are isolated complexes comprising a major histocompatibility complex (MHC) class II and a type I diabetes-associated GAD autoantigenic peptide, the isolated complex having a structural conformation which enables isolation of a high affinity entity which comprises an antigen binding domain capable of specifically binding to a native conformation of a complex composed of the MHC class II and the type I diabetes-associated GAD autoantigenic peptide; and isolated high affinity entities comprising an antigen binding domain capable of specifically binding the complex, wherein the isolated high affinity entity does not bind to the MHC class II in an absence of the diabetes-associated GAD autoantigenic peptide, wherein the isolated high affinity entity does not bind to the diabetes-associated GAD autoantigenic peptide in an absence of the MHC class II; and methods and kits using same for diagnostic and therapeutic purposes.

8 Claims, 15 Drawing Sheets
(13 of 15 Drawing Sheet(s) Filed in Color)

(56) References Cited

OTHER PUBLICATIONS

Burrows et al. "Design, Engineering and Production of Functional Single-Chain T Cell Receptor Ligands", Protein Engineering, 12(9): 771-778, Sep. 1999.
Burrows et al. "Rudimentary TCR Signaling Triggers Default IL-10 Secretion by Human Th1 Cells", The Journal of Immunology, 167(8): 4386-4395, Oct. 15, 2001.
Chang et al. "Design, Engineering and Production of Human Recombinant T Cell Receptor Ligands Derived From Human Leukocyte Antigen DR2", The Journal of Biological Chemistry, XP002538597, 276(26): 24170-24176, Jun. 29, 2001. Abstract, p. 24171, col. 1, Para 2—col. 2, Para 2.
Chung et al. "Competitive Inhibition In Vivo and Skewing of the T Cell Repertoire of Antigen-Specific CTL Priming by An Anti-Peptide-MHC Monoclonal Antibody", The Journal of Immunology, XP055008755, 167(2): 699-707, Jul. 1, 2001.
Cohen et al. "Direct Detection and Quantification of A Distinct T-Cell Epitope Derived From Tumor-Specific Epithelial Cell-Associated Mucin Using Human Recombinant Antibodies Endowed With the Antigen-Specific, Major Histocompatibility Complex-Restricted Specificity of T Cells", Cancer Research, 62: 5835-5844, 2002.
Cohen et al. "Recombinant Antibodies With MHC-Restricted, Peptide-Specific, T-Cell Receptor-Like Specificity: New Tooks to Study Antigen Presentation and TCR-Peptide-MHC Interactions", Journal of Molecular Recognition, XP008050078, 16(5): 324-332, Sep. 1, 2003. Abstract, p. 325, col. 1, Para 5—col. 2, Para 3, p. 330, col. 2, Para 3.
Dahan et al. "TCR-Like Antibodies Distinguish Conformational and Functional Difference in Two- Versus Four-Domain Auto Reactive MHC Class-II-Peptide Complexes", European Journal of Immunology, XP055008690, 41(5): 1465-1479, May 2011. Abstract, Figs.2, 4, p. 1474, col. 1, Para 2—col. 2, Para 3.
Dam-Tuxen et al. "Antibodies Against A Class II HLA-Peptide Complex Raised by Active Immunizatiion of Mice With Antigen Mimicking Peptides", Scandinavian Journal of Immunology, XP055019851, 70(2): 93-100, Aug. 1, 2009. Abstract, p. 93, col. 2, Para 1, p. 94, col. 2, Para 2-4, p. 97, col. 1, Para 2—col. 2, Para 2.
Denkberg et al. "Direct Visualization of Distinct T Cell Epitopes Derived From A Melanoma Tumor-Associated Antigen by Using Human Recombinant Antibodies With MHC-Restricted T Cell Receptor-Like Specificity", Proc. Natl. Acad. Sci. USA, PNAS, 99(14): 9421-9426, Jul. 9, 2002.
Denkberg et al. "Recombinant Antibodies With T-Cell Receptor-Like Specificity: Novel Tools to Study MHC Class I Presentation", Autoimmunity Research XP024977451, 5(4): 252-257, Apr. 1, 2006. Abstract.
Denkberg et al. "Selective Targeting of Melanoma and APCs Using A Recombinant Antibody With TCR-Like Specificity Directed Toward A Melanoma Differentiation Antigen", The Journal of Immunology, 171: 2197-2207, 2003.
Epel et al. "Targeting TARP, A Novel Breast and Prostate Tumor-Associated Antigen, With T-Cell Receptor-Like Human Recombinant Antibodies", European Journal of Immunology, 38(6): 1706-1720, Jun. 2008.
Huan et al. "MHC Class II Derived Recombinant T Cell Receptor Ligands Protect DBA/1LacJ Mice From Collagen-Induced Arthritis", the Journal of Immunology, XP002670030, 180(2): 1249-1257, Jan. 2008. Abstract, p. 1250, col. 2, Para 2-4, p. 1251, col. 2, Para 3—p. 1252, col. 2, Para 2, Fig.2.
International Multiple Sclerosis Genetics Consortium "A High-Density Screen for Linkage in Multiple Sclerosis", American Journal of Human Genetics, 77: 454-467, 2005.
Johns et al. "Myelin Oligodendrocyte Glycoprotein Induces A Demyelinating Encephalomyelitis Resembling Multiple Sclerosis", The Journal of Immunology, 154: 5536-5541, 1995.
Karlsen et al. "Cloning and Primary Structure of A Human Islet Isoform of Glutamic Acid Decarboxylase From Chromosome 10", Proc. Natl. Acad. Sci. USA, 88: 8337-8341, Oct. 1991.

Kerlero de Rosbo et al. "Reactivity to Myelin Antigens in Multiple Sclerosis. Peripheral Blood Lymphocytes Respond Predominantly to Myelin Oligodendrocyte Glycoprotein", Journal of Clinical Investigation, 92: 2602-2608, Dec. 1993.
Kerlero de Rosbo et al. "T-Cell Responses to Myelin Antigens in Multiple Sclerosis; Relevance of the Predominant Autoimmune Reactivity to Myelin Oligodendrocyte Glycoprotein", Journal of Autoimmunity, 11: 287-299, 1998.
Kroogsgaard et al. "Visualization of Myelin Basic Protein (MBP) T Cell Epitopes in Multiple Sclerosis Lesions Using A Monoclonal Antibody Specific for the Human Histocompatibility Leukocyte Antigen (HLA)-DR2-MBP 85-99 Complex", The Journal of Experimental Medicine, 191(8): 1395-1412, Apr. 17, 2000.
Lev et al. "Isolation and Characterization of Human Recombinant Antibodies Endowed With the Antigen-Specific, Major Histocompatibility Complex-Restricted Specifity of T Cells Directed Toward the Widely Expressed Tumor T-Cell Epitopes of the Telomerase Catalytic Subunit", Cancer Research, 62: 3184-3194, Jun. 1, 2002.
Link et al. "Monomeric DR2/MOG-35-55 Recombinant TCR Ligand Treats Relapses of Experimental Encephalomyelitis in DR2 Transgenic Mice", Clinical Immunology, 123: 95-104, 2007.
Lohmann et al. "T Cell Clones to Epitopes of Glutamic Acid Decarboxylase 65 Raised From Normal Subjects and Patients With Insulin-Dependent Diabetes", Journal of Autoimmunity, 9: 385-389, 1996.
Masewicz et al. "Modulation of T Cell Response to hGAD65 Peptide Epitopes", Tissue Antigens, 59: 101-112, 2002.
McDaniel et al. "Molecular Analysis of HLA-D Region Genes in Seropositive Rheumatoid Arthritis", Tissue Antigens, 34: 299-308, 1989.
Nepom "Conversation With GAD", Journal of Autoimmunity, 20: 195-198, 2003.
Nepom et al. "Identification and Modulation of a Naturally Processed T Cell Epitope From the Diabetes-Associated Autoantigen Human Glutamic Acid Decarboxylase 65 (hGAD65)", Proc. Natl. Acad. Sci, USA, PNAS, XP055008762, 98(4): 1763-1768, Feb. 13, 2001. Fig.4, p. 1767, r-h col., Para 3—p. 1768, 1-h col., Para 1.
Nepom et al. "MHC Class-II Molecules and Autoimmunity", Annual Reviews in Immunology, 9: 493-525, 1991.
Olerup et al. "HLA Class II-Asscociated Genetic Susceptibility in Multiple Sclerosis: A Critical Evaluation", Tissue Antigens, 38: 1-15, 1991.
Öling et al. "GAD65- and Proinsulin-Specific CD4+ T-Cells Detected by MHC Class II Tetramers in Peripheral Blood of Type 1 Diabetes Patients and At-Risk Subjects", Journal of Autoimmunity, XP005166208, 25(3): 235-243, Nov. 1, 2005. Abstract, p. 236, Section 2.1, p. 238, Section 2.3.
Ou et al. "CD4+ and CD8+ T-Cell Clones From Congenital Rubella Syndrome Patients With IDDM Recognize Overlapping GAD65 Protein Epitopes. Implications for HLA Clas I and II Allelic Linkage to Disease Susceptibility", Human Immunology, 60: 652-664, 1999.
Patel et al. "Identification of Immunodominant T Cell Epitopes of Human Glutamic Acid Decarboxylase 65 by Using HLA-DR(α1*0101,β1*0401) Transgenic Mice", Proc. Natl. Acad. Sci. USA, 94: 8082-8087, Jul. 1997.
Pawelec et al. "Dissection of Human Allostimulatory Determinants With Cloned T Cells: Stimulation Inhibition by Monoclonal Antibodies T?22, 34, 35, 36, 37, 39, 43, and 58 Against Distinct Human MHC Class II Molecules", Human Immunology, 12: 165-176, 1985.
Quill et al. "Stimulation of Normal Inducer T Cell Clones With Antigen Presented by Purified Ia Molecules in Planar Lipid Membranes: Specific Induction of a Long-Lived State of Proliferative Nonresponsiveness", The Journal of Immunology, 138(11): 3404-3412, Jun. 1, 1987.
Reijonen et al. "Detection of GAD65-Specific T-Cells by Major Histocompatibility Complex Class II Tetramers in Type 1 Diabetic Patients and At-Risk Subjects", Diabetes, 51: 1375-1382, 2002.
Reijonen et al. "Detection of GAD65-Specific T-Cells by Major Histocompatibility Complex Class II Tetramers in Type 1 Diabetic Patients and At-Risk Subjects", Diabetes, XP003010701, 51: 1375-1382, May 1, 2002.
Rharbaoui et al. "T Cell Response Pattern to Glutamic Acid Decarboxylase 65 (GAD65) Peptides of Newly Diagnosed Type 1

(56) References Cited

OTHER PUBLICATIONS

Diabetic Patients Sharing Susceptible HLA Haplotypes", Clinical and Experimental Immunology, 117: 30-37, 1999.

Rich et al. "Myelin Oligodendrocyte Glycoprotein-35-55 Peptide Induces Severe Chronic Experimental Autoimmune Encephalomyelitis in HLA-DR2-Transgenic Mice", European Journal of Immunology, 34: 1251-1261, 2004.

Roep et al. "Autoreactive T Cell Responses in Insulin-Dependent (Type 1) Diabetes Mellitus", Journal of Autoimmunity, JAI, 13: 267-282, 1999.

Schwartz "Models of T Cells Anergy: Is There A Common Molecular Mechanism?", The Journal of Experimental Medicine, 184: 1-8, Jul. 1996.

Sinha et al. "A Promising Therapeutic Approach for Multiple Sclerosis: Recombinant T-Cell Receptor Ligands Modulate Experimental Autoimmune Encephalomyelitis by Reducing Interleukin-17 Production and Inhibiting Migration of Encephalitogenic Cells Into the CNS", The Journal of Neuroscience, 27(46): 12531-12539, Nov. 14, 2007.

Sinha et al. "Binding of Recombinant T Cell Receptor Ligands (RTL) to Antigen Presenting Cells Prevents Upregulation of CD11b and Inhibits T Cell Activation and Transfer of Experimental Autoimmune Encephalomyelitis", Journal of Neuroimmunology, 225: 52-61, 2010.

Sinha et al. "Cytokine Switch and Bystander Suppression of Autoimmune Responses to Multiple Antigens in Experimental Autoimmune Encephalomyelitis by A Single Recombinant T-Cell Receptor Ligand", The Journal of Neuroscience, 29(12): 3816-3823, Mar. 25, 2000.

Svendsen et al. "Tracking of Proinflammatory Collagen-Specific T Cells in Early and Late Collagen-Induced Arthritis in Humanized Mice", sThe Journal of Immunology, XP002661381, 173(11): 7037-7045, Dec. 1, 2004.

Trapp et al. "Multiple Sclerosis: An Immune or Neurodegenerative Disorder?", Annual Review of Neuroscience, 31: 247-267, 2008.

Verge et al. "Prediction of Type I Diabetes in First-Degree Relatives Using A Combination of Insulin, GAD, and ICA512bdc/IA-2 Autoantibodies", Diabetes, 45: 926-233, 1996.

Wang et al. "Recombinant TCR Ligand Induces Early TCR Signaling and A Unique Pattern of Downstream Activation", Journal of Immunology, 171: 1934-1940, 2003.

Yadav "Recombinant T Cell Receptor Ligand (RTL) for the Treatment of Multiple Sclerosis: Report of A Phase I Clinical Trial", Department of Neurology, Oregon Health & Science University (OHSU).

Ziegler et al. "Analysis by Sequential Immunoprecipitations of the Specificities of the Monoclonal Antibodies TÜ22, 34, 35, 36, 37, 39, 43, 58 and YD1/63.HLK Directed Against Human HLA Class II Antigens", Immunobiology, 171: 77-92, 1986.

Jones et al. "MHC Class II Proteins and Disease: A Structural Perspective", Nature Reviews Immunology, XP055275619, 6(4): 271-282, Apr. 1, 2006.

Adarnashvili et al. "Soluble HLA Measurement in Saliva and Cerebrospinal Fluid in Caucasian Patients With Multiple Sclerosis: A Preliminary Study", Journal of Neuroinflammation, 2(13): pp. 1-7, Published Online Jun. 2, 2005.

Huan et al. "Rationally Designed Mutations Convert Complexes of Human Recombinant T Cell Receptor Ligands into Monomers that Retain Biological Activity", Journal of Chemical Technology and Biotechnology, 80(1): 2-12, Jan. 2005.

Wang et al. "Monoclonal Antibody Pharmacokinetics and Pharmacodynamics", Clinical Pharmacology and Therapeutics 84(5): 548-558, Nov. 2008.

\* cited by examiner

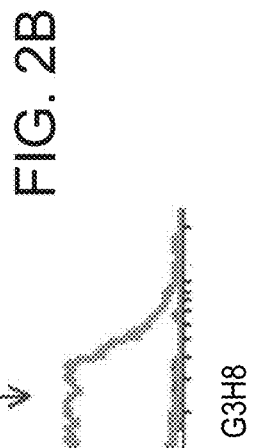
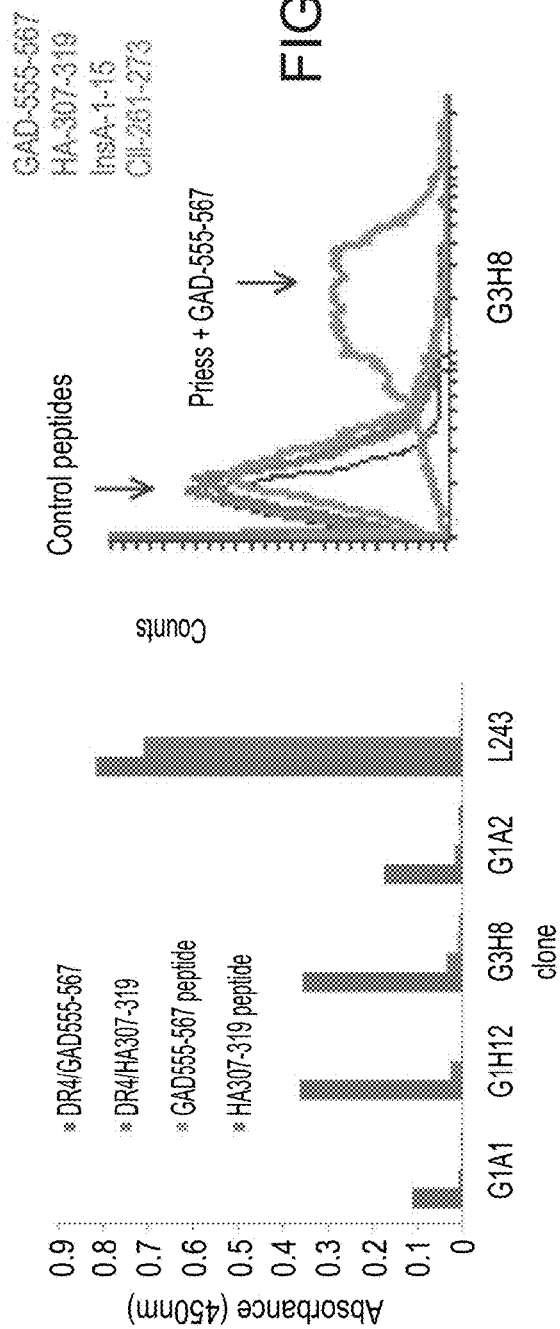
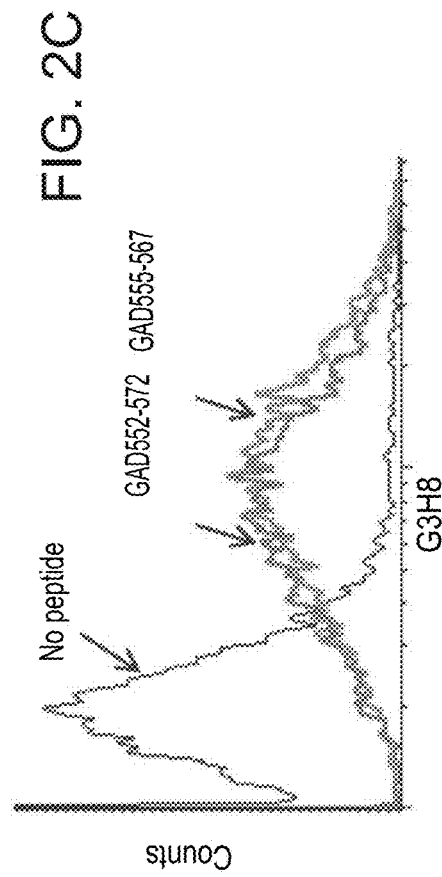

FIG. 2D
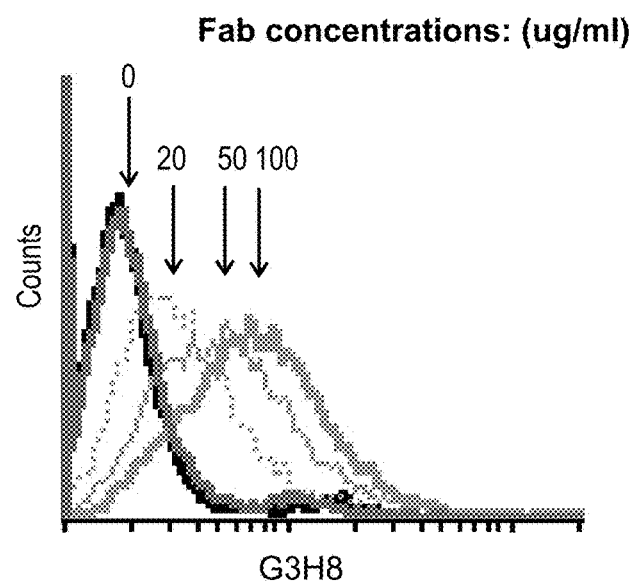
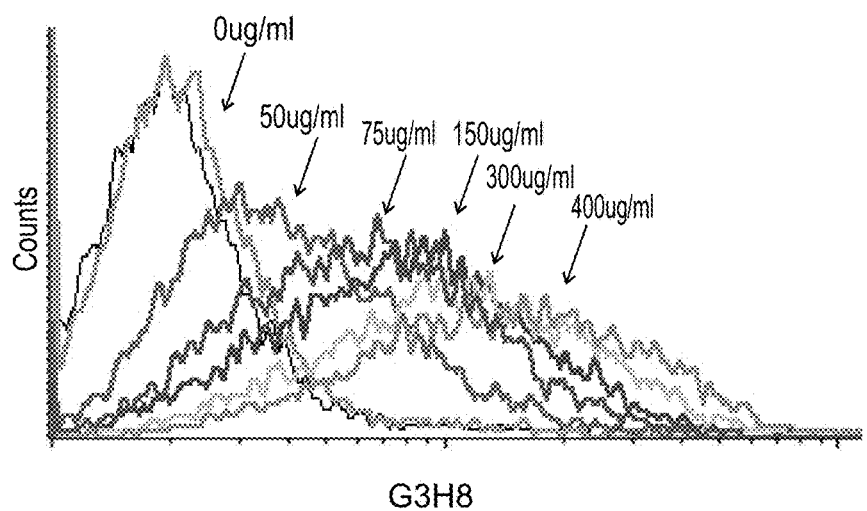
FIG. 2E

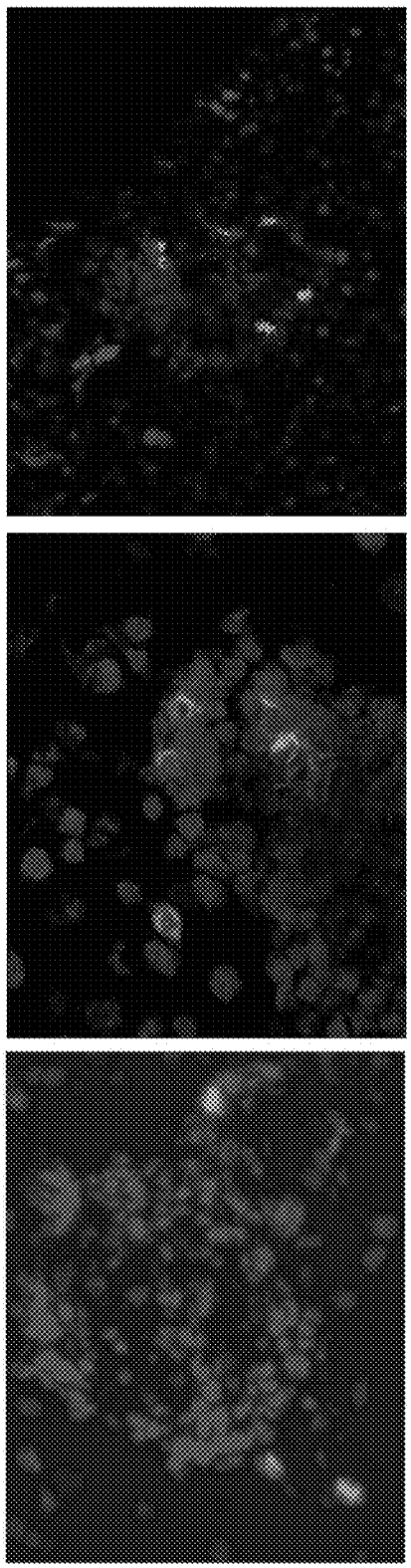
FIG. 5C
FIG. 5B
FIG. 5A
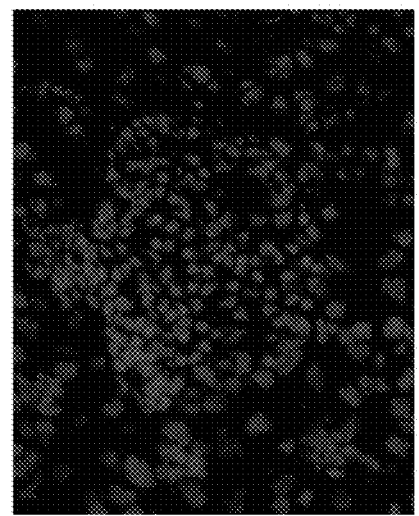
FIG. 5E
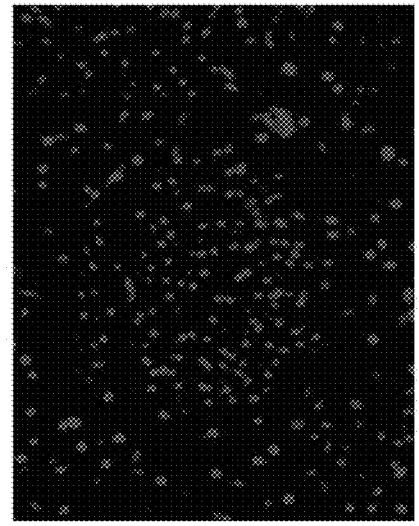
FIG. 5D

G3H8 light chain [variable(VL)+ constant (CL) domains] amino acid sequence
LETTLTQSPATLSVSPGERVTLSCRASQSVGSNLAWYQQKFGQAPRLLIYDASTRATGIPAR
FSGSGSGTEFTLTISRLEPEDFAVYYCHQYGSSPRTFGQGTKVDIKRTVAAPSVFIFPPSDE
QLKSGTASVVCLLNNFYPREAKVQWKVDNALQSGNSQESVTEQDSKDSTYSLSSTLTLSKAD
YEKHKVYACEVTHQGLSSPVTKSFNRGEC(SEQ ID NO:1)

FIG. 6A

G3H8 light chain [variable(VL)+ constant (CL) domains] nucleic acid sequence
CTTGAAACGACACTCACGCAGTCTCCAGCCACCCTGTCTGTGTCTCCAGGGGAAAGAGTCAC
CCTCTCCTGCAGGGCCAGTCAGAGTGTTGGCAGCAACTTAGCCTGGTACCAGCAGAAATTTG
GCCAGGCTCCCAGGCTCCTCATCTATGATGCATCCACCAGGGCCACTGGTATCCCAGCCAGG
TTCAGTGGCAGTGGGTCTGGGACAGAGTTCACTCTCACCATCAGCAGACTGGAGCCTGAAGA
TTTTGCAGTGTATTACTGTCACCAGTATGGTAGCTCACCTCGGACGTTCGGCCAAGGGACCA
AGGTGGACATCAAACGAACTGTGGCTGCACCATCTGTCTTCATCTTCCCGCCATCTGATGAG
CAGTTGAAATCTGGAACTGCCTCTGTTGTGTGCCTGCTGAATAACTTCTATCCCAGAGAGGC
CAAAGTACAGTGGAAGGTGGATAACGCCCTCCAATCGGGTAACTCCCAGGAGAGTGTCACGG
AGCAGGACAGCAAGGACAGCACCTACAGCCTCAGCAGCACCCTGACGCTGAGCAAAGCAGAC
TACGAGAAACACAAAGTCTACGCCTGCGAAGTCACCCATCAGGGCCTGAGCTCGCCCGTCAC
AAAGAGCTTCAACAGGGGAGAGTGTTAATAAGGCGCGCCAATTCTATTT (SEQ ID NO:2)

FIG. 6B

G3H8 heavy chain [variable(VH)+ constant 1(CH1) domains] amino acid sequence
QVQLVQSGAEVKKPGASVKVSCKASGYTFTTYGISWVRQAPGQGLEWMGWISAYNGHTNYAQ
MLQGRVTMTTDTSTSTAYMELRGLRSDDTAVYYCAREAYASYGSGSYWTDYWGQGTLVTVSS
AASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCAAAHHHHHHGAAEQKLISEE
DLNGAA(SEQ ID NO:3)

FIG. 6C

G3H8 heavy chain [variable(VH)+ constant 1(CH1) domains] nucleic acid sequence
CAGGTCCAGCTGGTACAGTCTGGGGCTGAGGTGAAGAAGCCTGGGGCCTCAGTGAAGGTCTC
CTGCAAGGCTTCTGGTTACACCTTTACCACCTATGGTATCAGCTGGGTGCGACAGGCCCCTG
GACAAGGGCTTGAGTGGATGGGATGGATCAGCGCTTACAATGGTCACACAAACTATGCACAG
ATGCTCCAGGGCAGAGTCACCATGACCACAGACACATCCACGAGCACAGCCTACATGGAGCT
GAGGGGCCTGAGATCTGACGACACGGCCGTGTATTACTGTGCGAGAGAGGCCTATGCTTCCT
ATGGTTCGGGGAGTTATTGGACTGACTACTGGGGCCAGGGAACCCTGGTCACCGTCTCAAGC
GCCTCCACCAAGGGCCCATCGGTCTTCCCCCTGGCACCCTCCTCCAAGAGCACCTCTGGGGG
CACAGCGGCCCTGGGCTGCCTGGTCAAGGACTACTTCCCCGAACCGGTGACGGTGTCGTGGA
ACTCAGGCGCCCTGACCAGCGGCGTCCACACCTTCCCGGCTGTCCTACAGTCCTCAGGACTC
TACTCCCTCAGCAGCGTAGTGACCGTGCCCTCCAGCAGCTTGGGCACCCAGACCTACATCTG
CAACGTGAATCACAAGCCCAGCAACACCAAGGTGGACAAGAAAGTTGAGCCCAAATCTTGTG
CGGCCGCACATCATCATCACCATCACGGGGCCGCAGAACAAAAACTCATCTCAGAAGAGGAT
CTGAATGGGGCCGCA (SEQ ID NO:4)

FIG. 6D

G1H12 light chain [variable(VL)+ constant (CL) domains] amino acid sequence
QSVLTQPPSVSAAPGQKVTISCSGSSSNIGNNYVSWYQQLPGTAPKLLIYDNNKRPSGIPDR
FSGSKSGTSATLGITGLQTGDEADYYCGTWDSSLSVWVFGGGTKLTVLGQPKAAPSVTLFPP
SSEELQANKATLVCLISDFYPGAVTVAWKADSSPVKAGVETTTPSKQSNNKYAASSYLSLTP
EQWKSHRSYSCQVTHEGSTVEKTVAPTECS (SEQ ID NO:5)

FIG. 7A

G1H12 light chain [variable(VL)+ constant (CL) domains] nucleic acid sequence
CAGTCTGTGCTGACGCAGCCGCCCTCAGTGTCTGCGGCCCAGGACAGAAGGTCACCATCTC
CTGCTCTGGAAGCAGCTCCAACATTGGGAATAATTATGTATCCTGGTACCAGCAGCTCCCAG
GAACAGCCCCCAAACTCCTCATTTATGACAATAATAAGCGACCCTCAGGGATTCCTGACCGA
TTCTCTGGCTCCAAGTCTGGCACGTCAGCCACCCTGGGCATCACCGGACTCCAGACTGGGGA
CGAGGCCGATTATTACTGCGGAACATGGGATAGCAGCCTGAGTGTCTGGGTGTTCGGCGGAG
GGACCAAGCTGACCGTCCTAGGTCAGCCCAAGGCTGCCCCCTCGGTCACTCTGTTCCCGCCC
TCCTCTGAGGAGCTTCAAGCCAACAAGGCCACACTGGTGTGTCTCATAAGTGACTTCTACCC
GGGAGCCGTGACAGTGGCCTGGAAGGCAGATAGCAGCCCCGTCAAGGCGGGAGTGGAGACCA
CCACACCCTCCAAACAAAGCAACAACAAGTACGCGGCCAGCAGCTACCTGAGCCTGACGCCT
GAGCAGTGGAAGTCCCACAGAAGCTACAGCTGCCAGGTCACGCATGAAGGGAGCACCGTGGA
GAAGACAGTGGCCCCTACAGAATGTTCATAATAA (SEQ ID NO:6)

FIG. 7B

G1H12 heavy chain [variable(VH)+ constant 1(CH1) domains]
amino acid sequence
QVQLVQSGAEVKKPGASVKVSCKASGYTFTSYGISWVRQAPGQGLEWMGGIIPIFGTANYAQ
KFQGRVTITADKSTSTAYMELSSLRSEDTAVYYCARDPQSYYYDSSGFDYWGQGTLVTVSSA
STKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCAAAHHHHHGAAEQKLISEEDL
NGAA (SEQ ID NO:7)

FIG. 7C

G1H12 heavy chain [variable(VH)+ constant 1(CH1) domains]
nucleic acid sequence

CAGGTCCAGCTGGTGCAGTCTGGAGCTGAGGTGAAGAAGCCTGGGGCCTCAGTGAAGGTCTC
CTGCAAGGCTTCTGGTTACACCTTTACCAGCTATGGTATCAGCTGGGTGCGACAGGCCCCTG
GACAAGGGCTTGAGTGGATGGGAGGGATCATCCCTATCTTTGGTACAGCAAACTACGCACAG
AAGTTCCAGGGCAGAGTCACGATTACCGCGGACAAATCCACGAGCACAGCCTACATGGAGCT
GAGCAGCCTGAGATCTGAAGACACGGCTGTGTATTACTGTGCGAGAGATCCCAGTCCTATT
ACTATGATAGTAGTGGTTTTGACTACTGGGGCCAGGGAACCCTGGTCACCGTCTCAAGCGCC
TCCACCAAGGGCCCATCGGTCTTCCCCCTGGCACCCTCCTCCAAGAGCACCTCTGGGGGCAC
AGCGGCCCTGGGCTGCCTGGTCAAGGACTACTTCCCCGAACCGGTGACGGTGTCGTGGAACT
CAGGCGCCCTGACCAGCGGCGTCCACACCTTCCCGGCTGTCCTACAGTCCTCAGGACTCTAC
TCCCTCAGCAGCGTAGTGACCGTGCCCTCCAGCAGCTTGGGCACCCAGACCTACATCTGCAA
CGTGAATCACAAGCCCAGCAACACCAAGGTGGACAAGAAAGTTGAGCCCAAATCTTGTGCGG
CCGCACATCATCATCACCATCACGGGGCCGCAGAACAAAAACTCATCTCAGAAGAGGATCTG
AATGGGGCCGCA (SEQ ID NO:8)

FIG. 7D

[...]GDTNFFRMVISNPAATGGGSLVPRGSGGGGSRP
PFLEQVKHECHFFNGTERVRFLDRYFYHQEEYVRFDSDVGEYRAVTELGRPDAEYWNSQKDL
LEQRRAAVDTYCRHNYGVGESFTVQRRVYPEVTVYPAKTQPLQHHNLLVCSVNGFYPGSIEV
RWFRNGQEEKTGVVSTGLIQNGDWTFQTLVMLETVPRSGEVYTCQVEHPSLTSPLTVEWRAR
SESAQSKVDGGGGGPIAPLEEKVKTLRAQNSELASTANMLREQVAQLKQKVMNH (SEQ ID
NO:9)

FIG. 8A

[...]IKEEHVIIQAEFYLNPDQSGEFMFDFDGDEIFHVDMA
KKETVWRLEEFGRFASFEAQGALANIAVDKANLEIMTKRSNYTPITNVPPEVTVLTNSPVEL
REPNVLICFIDKFTPPVVNVTWLRNGKPVTTGVSETVFLPREDHLFRKFHYLPFLPSTEDVY
DCRVEHWGLDEPLLKHWEFDAPSPLPETTENVDGGGGGLFDTLQAETDQLEDEKSALQTEIA
NLLKEKEKLEFILAAHGLNDIFEAQKIEWH (SEQ ID NO:10)

FIG. 8B

```
[shaded header region]GGGGACACCAACTTCTTTCGTATGGTTATCAGCAATC
CAGCTGCGACTGGTGGTGGCTCACTAGTGCCACGGGGCTCTGGAGGAGGTGGGTCCCGACCA
CGTTCTTGGAGCAGGTTAAACATGAGTGTCATTCTTCAACGGGACGGAGCGGGTGCGGTT
CCTGGACAGATACTTCTATCACCAAGAGGAGTACGTGCGCTTCGACAGCGACGTGGGGAGT
ACCGGGCGGTGACGGAGCTGGGGCGGCCTGATGCCGAGTACTGGAACAGCCAGAAGGACCTC
CTGGAGCAGAAGCGGGCCGCGGTGGACACCTACTGCAGACACAACTACGGGGTTGGTGACAG
CTTCACAGTGCAGCGGCGAGTCTATCCTGAGGTGACTGTGTATCCTGCAAAGACCCAGCCCC
TGCAGCACCACAACCTCCTGGTCTGCTCTGTGAATGGTTTCTATCCAGGCAGCATTGAAGTC
AGGTGGTTCCGGAACGGCCAGGAAGAGAAGACTGGGGTGGTGTCCACAGGCCTGATCCAGAA
TGGAGACTGGACCTTCCAGACCCTGGTGATGCTGGAAACAGTTCCTCGGAGTGGAGAGGTTT
ACACCTGCCAAGTGGAGCACCCAAGCCTGACGAGCCCTCTCACAGTGGAATGGAGAGCACGG
TCTGAATCTGCACAGAGCAAGGTCGACGGAGGTGGCGGCGGTCGCATCGCCCGGCTGAGGA
AAAAGTGAAAACCTTGAAAGCTCAGAACTCGGAGCTGGCGTCCACGGCCAACATGCTCAGGG
AACAGGTGGCACAGCTTAAACAGAAAGTCATGAACCAT (SEQ ID NO:11)
```

FIG. 9A

```
[shaded header region]ATCAAAGAAGAACATGTGATCATCCAGGCCGAGTTCTATCTGAATCCTG
ACCAATCAGGCGAGTTTATGTTTGACTTTGATGGTGATGAGATTTTCCATGTGGATATGGCA
AAGAAGGAGACGGTCTGGCGGCTTGAAGAATTTGGACGATTTGCCAGCTTTGAGGCTCAAGG
TGCATTGGCCAACATAGCTGTGGACAAAGCCAACCTGGAAATCATGACAAAGCGCTCCAACT
ATACTCCGATCACCAATGTACCTCCAGAGGTAACTGTGCTCACGAACAGCCCTGTGGAACTG
AGAGAGCCCAACGTCCTCATCTGTTTCATCGACAAGTTCACCCCACCAGTGGTCAATGTCAC
GTGGCTTCGAAATGGAAAACCTGTCACCACAGGAGTGTCAGAGACAGTCTTCCTGCCCAGGG
AAGACCACCTTTTCCGCAAGTTCCACTATCTCCCCTTCCTGCCCTCAACTGAGGACGTTTAC
GACTGCAGGGTGAGCACTGGGCTTGGATGAGCCTCTTCTCAAGCACTGGGAGTTTGATGCT
CCAAGCCCTCTCCAGAGACTACAGAGAACGTCGACGGAGGTGGCGGCGGTTAACTGATACA
CTCCAAGCGGAGACAGATCAACTTGAAGACGAGAAGTCTGCGTTGCAGACCGAGATTGCCAA
TCTACTGAAAGAGAAGGAAAAACTGGAGTTCATCCTGGCCGCCATGGCCTGAACGACATCT
TCGAGGCCCAGAAGATCGAGTGGCAC (SEQ ID NO:12)
```

FIG. 9B

SEQUENCE LISTING

```
<160> NUMBER OF SEQ ID NOS: 102

<210> SEQ ID NO 1
<211> LENGTH: 215
<212> TYPE: PRT
<213> ORGANISM: Artificial sequence
<220> FEATURE:
<223> OTHER INFORMATION: G3H8 light chain [variable(VL)+ constant (CL)
      domains] amino acid sequence

<400> SEQUENCE: 1

Leu Glu Thr Thr Leu Thr Gln Ser Pro Ala Thr Leu Ser Val Ser Pro
1               5                   10                  15

Gly Glu Arg Val Thr Leu Ser Cys Arg Ala Ser Gln Ser Val Gly Ser
            20                  25                  30

Asn Leu Ala Trp Tyr Gln Gln Lys Phe Gly Gln Ala Pro Arg Leu Leu
        35                  40                  45

Ile Tyr Asp Ala Ser Thr Arg Ala Thr Gly Ile Pro Ala Arg Phe Ser
    50                  55                  60

Gly Ser Gly Ser Gly Thr Glu Phe Thr Leu Thr Ile Ser Arg Leu Glu
65                  70                  75                  80

Pro Glu Asp Phe Ala Val Tyr Tyr Cys His Gln Tyr Gly Ser Ser Pro
                85                  90                  95

Arg Thr Phe Gly Gln Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 2
<211> LENGTH: 669
<212> TYPE: DNA
<213> ORGANISM: Artificial sequence
<220> FEATURE:
<223> OTHER INFORMATION: G3H8 light chain [variable(VL)+ constant (CL)
      domains] nucleic acid sequence

<400> SEQUENCE: 2
cttgaaacga cactcacgca gtctccagcc accctgtctg tgtctccagg ggaaagagtc        60
accctctcct gcagggccag tcagagtgtt ggcagcaact tagcctggta ccagcagaaa       120
```

```
tttggccagg ctcccaggct cctcatctat gatgcatcca ccagggccac tggtatccca      180
gccaggttca gtggcagtgg gtctgggaca gagttcactc tcaccatcag cagactggag      240
cctgaagatt ttgcagtgta ttactgtcac cagtatggta gctcacctcg acgttcggc      300 caagggacca aggtggacat caaacgaact gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacggagca ggacagcaag gacagcacct acagcctcag cagcaccctg      540
acgctgagca agcagactac gagaaacac aaagtctacg cctgcgaagt cacccatcag      600
ggcctgagct cgcccgtcac aaagagcttc aacaggggag agtgttaata aggcgcgcca      660
attctatt                                                              669
```

<210> SEQ ID NO 3
<211> LENGTH: 254
<212> TYPE: PRT
<213> ORGANISM: Artificial sequence
<220> FEATURE:
<223> OTHER INFORMATION: G3H8 heavy chain [variable(VH)+ constant 1(CH1) domains] amino acid sequence

<400> SEQUENCE: 3

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly His Thr Asn Tyr Ala Gln Met Leu
    50                  55                  60

Gln Gly Arg Val Thr Met Thr Thr Asp Thr Ser Thr Ser Thr Ala Tyr
65                  70                  75                  80

Met Glu Leu Arg Gly Leu Arg Ser Asp Asp Thr Ala Val Tyr Tyr Cys
                85                  90                  95

Ala Arg Glu Ala Tyr Ala Ser Tyr Gly Ser Gly Ser Tyr Trp Thr Asp
            100                 105                 110

Tyr Trp Gly Gln Gly Thr Leu Val Thr Val Ser Ser Ala Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Ala Ala Ala His His His His His His Gly Ala Ala
225                 230                 235                 240

Glu Gln Lys Leu Ile Ser Glu Glu Asp Leu Asn Gly Ala Ala
                245                 250
```

<210> SEQ ID NO 4
<211> LENGTH: 759
<212> TYPE: DNA
<213> ORGANISM: Artificial sequence
<220> FEATURE:
<223> OTHER INFORMATION: G3H8 heavy chain [variable(VH)+ constant 1(CH1) domains] nucleic acid sequence

<400> SEQUENCE: 4

```
caggtccagc tggtacagtc tggggctgag gtgaagaagc tggggcctc  agtgaaggtc      60
tcctgcaagg cttctggtta cacctttacc acctatggta tcagctgggt gcgacaggcc     120
cctggacaag gcttgagtg gatgggatgg atcagcgctt acaatggtca cacaaactat     180
gcacagatgc tccagggcag agtcaccatg accacagaca catccacgag cacagcctac     240
atggagctga ggggcctgag atctgacgac acggccgtgt attactgtgc gagagaggcc     300
tatgcttcct atggttcggg gagttattgg actgactact ggggccaggg aaccctggtc     360
accgtctcaa gcgcctccac caagggccca tcggtcttcc ccctggcacc ctcctccaag     420
agcacctctg ggggcacagc ggccctgggc tgcctggtca aggactactt ccccgaaccg     480
gtgacggtgt cgtggaactc aggcgccctg accagcggcg tccacacctt cccggctgtc     540
ctacagtcct caggactcta ctccctcagc agcgtagtga ccgtgccctc agcagcttg     600
ggcacccaga cctacatctg caacgtgaat cacaagccca gcaacaccaa ggtgacaag     660
aaagttgagc ccaaatcttg tgcggccgca catcatcatc accatcacgg ggccgcagaa     720
caaaaactca tctcagaaga ggatctgaat ggggccgca                           759
```

<210> SEQ ID NO 5
<211> LENGTH: 216
<212> TYPE: PRT
<213> ORGANISM: Artificial sequence
<220> FEATURE:
<223> OTHER INFORMATION: G1H12 light chain [variable(VL)+ constant (CL) domains] amino acid sequence

<400> SEQUENCE: 5

```
Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Val Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
```

```
                165                 170                 175
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 6
<211> LENGTH: 654
<212> TYPE: DNA
<213> ORGANISM: Artificial sequence
<220> FEATURE:
<223> OTHER INFORMATION: G1H12 light chain [variable(VL)+ constant (CL)
      domains] nucleic acid sequence

<400> SEQUENCE: 6
cagtctgtgc tgacgcagcc gccctcagtg tctgcggccc caggacagaa ggtcaccatc      60
tcctgctctg gaagcagctc caacattggg aataattatg tatcctggta ccagcagctc     120
ccaggaacag cccccaaact cctcatttat gacaataata gcgaccctca gggattcct      180 gaccgattct ctggctccaa gtctggcacg tcagccaccc tgggcatcac cggactccag     240
actggggacg aggccgatta ttactgcgga acatgggata gcagcctgag tgtctgggtg     300
ttcggcggag gaccaagct gaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca caagtacgc ggccagcagc     540 tacctgagcc tgacgcctga cagtggaag tcccacagaa gctacagctg ccaggtcacg     600
catgaaggga gcaccgtgga agacagtg gcccctacag aatgttcata ataa            654

<210> SEQ ID NO 7
<211> LENGTH: 252
<212> TYPE: PRT
<213> ORGANISM: Artificial sequence
<220> FEATURE:
<223> OTHER INFORMATION: G1H12 heavy chain [variable(VH)+ constant
      1(CH1) domains] amino acid sequence

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gln Ser Tyr Tyr Tyr Asp Ser Ser Gly Phe Asp Tyr
            100                 105                 110

Trp Gly Gln Gly Thr Leu Val Thr Val Ser Ser Ala Ser Thr Lys Gly
        115                 120                 125
```

-continued

```
Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Ala Ala Ala His His His His His Gly Ala Ala Glu Gln
225                 230                 235                 240

Lys Leu Ile Ser Glu Glu Asp Leu Asn Gly Ala Ala
                245                 250
```

<210> SEQ ID NO 8
<211> LENGTH: 756
<212> TYPE: DNA
<213> ORGANISM: Artificial sequence
<220> FEATURE:
<223> OTHER INFORMATION: G1H12 heavy chain [variable(VH)+ constant
      1(CH1) domains] nucleic acid sequence

<400> SEQUENCE: 8

```
caggtccagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag gcttgagtg gatgggaggg atcatccta tctttggtac agcaaactac      180
gcacagaagt tccagggcag agtcacgatt accgcggaca atccacgag cacagcctac      240 atggagctga gcagcctgag atctgaagac acggctgtgt attactgtgc gagagatccc      300
cagtcctatt actatgatag tagtggtttt gactactggg gccagggaac cctggtcacc      360
gtctcaagcg cctccaccaa gggcccatcg gtcttccccc tggcaccctc ctccaagagc      420
acctctgggg gcacagcggc cctgggctgc ctggtcaagg actacttccc cgaaccggtg      480
acggtgtcgt ggaactcagg cgccctgacc agcggcgtcc acaccttccc ggctgtccta      540
cagtcctcag gactctactc cctcagcagc gtagtgaccg tgccctccag cagcttgggc      600
acccagacct acatctgcaa cgtgaatcac aagcccagca acaccaaggt ggacaagaaa      660
gttgagccca atcttgtgc ggccgcacat catcatcacc atcacggggc cgcagaacaa      720
aaactcatct cagaagagga tctgaatggg gccgca                               756
```

<210> SEQ ID NO 9
<211> LENGTH: 302
<212> TYPE: PRT
<213> ORGANISM: Artificial sequence
<220> FEATURE:
<223> OTHER INFORMATION: Recombinant beta chain (DRB1*0401)

<400> SEQUENCE: 9

```
Met Val Cys Leu Lys Phe Pro Gly Gly Ser Cys Met Thr Ala Leu Thr
1               5                   10                  15

Val Thr Leu Met Val Leu Ser Ser Pro Leu Ala Leu Ala Gly Asp Thr
            20                  25                  30

Asn Phe Phe Arg Met Val Ile Ser Asn Pro Ala Ala Thr Gly Gly Gly
        35                  40                  45
```

```
Ser Leu Val Pro Arg Gly Ser Gly Gly Gly Ser Arg Pro Arg Phe
 50                  55                  60

Leu Glu Gln Val Lys His Glu Cys His Phe Phe Asn Gly Thr Glu Arg
 65                  70                  75                  80

Val Arg Phe Leu Asp Arg Tyr Phe Tyr His Gln Glu Glu Tyr Val Arg
                 85                  90                  95

Phe Asp Ser Asp Val Gly Glu Tyr Arg Ala Val Thr Glu Leu Gly Arg
            100                 105                 110

Pro Asp Ala Glu Tyr Trp Asn Ser Gln Lys Asp Leu Leu Glu Gln Lys
            115                 120                 125

Arg Ala Ala Val Asp Thr Tyr Cys Arg His Asn Tyr Gly Val Gly Glu
            130                 135                 140

Ser Phe Thr Val Gln Arg Arg Val Tyr Pro Glu Val Thr Val Tyr Pro
145                 150                 155                 160

Ala Lys Thr Gln Pro Leu Gln His His Asn Leu Leu Val Cys Ser Val
                165                 170                 175

Asn Gly Phe Tyr Pro Gly Ser Ile Glu Val Arg Trp Phe Arg Asn Gly
            180                 185                 190

Gln Glu Glu Lys Thr Gly Val Val Ser Thr Gly Leu Ile Gln Asn Gly
            195                 200                 205

Asp Trp Thr Phe Gln Thr Leu Val Met Leu Glu Thr Val Pro Arg Ser
            210                 215                 220

Gly Glu Val Tyr Thr Cys Gln Val Glu His Pro Ser Leu Thr Ser Pro
225                 230                 235                 240

Leu Thr Val Glu Trp Arg Ala Arg Ser Glu Ser Ala Gln Ser Lys Val
                245                 250                 255

Asp Gly Gly Gly Gly Arg Ile Ala Arg Leu Glu Glu Lys Val Lys
            260                 265                 270

Thr Leu Lys Ala Gln Asn Ser Glu Leu Ala Ser Thr Ala Asn Met Leu
            275                 280                 285

Arg Glu Gln Val Ala Gln Leu Lys Gln Lys Val Met Asn His
            290                 295                 300

<210> SEQ ID NO 10
<211> LENGTH: 278
<212> TYPE: PRT
<213> ORGANISM: Artificial sequence
<220> FEATURE:
<223> OTHER INFORMATION: Recombinant alpha chain (DRA1*0101)

<400> SEQUENCE: 10

Met Ala Ile Ser Gly Val Pro Val Leu Gly Phe Phe Ile Ile Ala Val
 1               5                  10                  15

Leu Met Ser Ala Gln Glu Ser Trp Ala Ile Lys Glu Glu His Val Ile
                 20                  25                  30

Ile Gln Ala Glu Phe Tyr Leu Asn Pro Asp Gln Ser Gly Glu Phe Met
            35                  40                  45

Phe Asp Phe Asp Gly Asp Glu Ile Phe His Val Asp Met Ala Lys Lys
 50                  55                  60

Glu Thr Val Trp Arg Leu Glu Glu Phe Gly Arg Phe Ala Ser Phe Glu
 65                  70                  75                  80

Ala Gln Gly Ala Leu Ala Asn Ile Ala Val Asp Lys Ala Asn Leu Glu
                 85                  90                  95

Ile Met Thr Lys Arg Ser Asn Tyr Thr Pro Ile Thr Asn Val Pro Pro
            100                 105                 110
```

```
Glu Val Thr Val Leu Thr Asn Ser Pro Val Glu Leu Arg Glu Pro Asn
        115                 120                 125

Val Leu Ile Cys Phe Ile Asp Lys Phe Thr Pro Pro Val Val Asn Val
130                 135                 140

Thr Trp Leu Arg Asn Gly Lys Pro Val Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
                180                 185                 190

Trp Gly Leu Asp Glu Pro Leu Leu Lys His Trp Glu Phe Asp Ala Pro
                195                 200                 205

Ser Pro Leu Pro Glu Thr Thr Glu Asn Val Asp Gly Gly Gly Gly Gly
        210                 215                 220

Leu Thr Asp Thr Leu Gln Ala Glu Thr Asp Gln Leu Glu Asp Glu Lys
225                 230                 235                 240

Ser Ala Leu Gln Thr Glu Ile Ala Asn Leu Leu Lys Glu Lys Glu Lys
                245                 250                 255

Leu Glu Phe Ile Leu Ala Ala His Gly Leu Asn Asp Ile Phe Glu Ala
            260                 265                 270

Gln Lys Ile Glu Trp His
        275

<210> SEQ ID NO 11
<211> LENGTH: 906
<212> TYPE: DNA
<213> ORGANISM: Artificial sequence
<220> FEATURE:
<223> OTHER INFORMATION: Recombinant beta chain (DRB1*0401) nucleic acid
      sequence

<400> SEQUENCE: 11
atggtgtgtc tgaagttccc tggaggctcc tgcatgacag cgctgacagt gacactgatg      60
gtgctgagct ccccactggc tttggctggg acaccaact tctttcgtat ggttatcagc      120
aatccagctg cgactggtgg tggctcacta gtgccacggg gctctggagg aggtgggtcc      180
cgaccacgtt tcttggagca ggttaaacat gagtgtcatt tcttcaacgg gacggagcgg      240
gtgcggttcc tggacagata cttctatcac caagaggagt acgtgcgctt cgacagcgac      300
gtgggggagt accgggcggt gacggagctg gggcggcctg atgccgagta ctggaacagc      360
cagaaggacc tcctggagca gaagcgggcc gcggtgaca cctactgcag acacaactac      420
ggggttggtg agagcttcac agtgcagcgg cgagtctatc ctgaggtgac tgtgtatcct      480
gcaaagaccc agccctgca gcaccacaac ctcctggtct gctctgtgaa tggtttctat      540
ccaggcagca ttgaagtcag gtggttccgg aacggccagg aagagaagac tgggtggtg      600 tccacaggcc tgatccagaa tggagactgg accttccaga ccctggtgat gctgaaaca      660 gttcctcgga gtgagaggt ttacacctgc caagtggagc acccaagcct gacgagccct      720
ctcacagtgg aatggagagc acggtctgaa tctgcacaga gcaaggtcga cggaggtggc      780
ggcggtcgca tcgcccggct cgaggaaaaa gtgaaaacct tgaaagctca gaactcggag      840
ctggcgtcca cggccaacat gctcagggaa caggtggcac agcttaaaca gaaagtcatg      900
aaccat                                                                906

<210> SEQ ID NO 12
```

-continued

```
<211> LENGTH: 834
<212> TYPE: DNA
<213> ORGANISM: Artificial sequence
<220> FEATURE:
<223> OTHER INFORMATION: Recombinant alpha chain (DRA1*0101) nucleic
      acid sequence

<400> SEQUENCE: 12
atggccataa gtggagtccc tgtgctagga tttttcatca tagctgtgct gatgagcgct      60
caggaatcat gggctatcaa agaagaacat gtgatcatcc aggccgagtt ctatctgaat     120
cctgaccaat caggcgagtt tatgtttgac tttgatggtg atgagatttt ccatgtggat     180
atggcaaaga aggagacggt ctggcggctt gaagaatttg gacgatttgc cagctttgag     240
gctcaaggtg cattggccaa catagctgtg acaaagcca acctggaaat catgacaaag      300
cgctccaact atactccgat caccaatgta cctccagagg taactgtgct cacgaacagc     360
cctgtggaac tgagagagcc aacgtcctc atctgtttca tcgacaagtt caccccacca      420
gtggtcaatg tcacgtggct tcgaaatgga aaacctgtca ccacaggagt gtcagagaca     480
gtcttcctgc cagggaaga ccacctttc cgcaagttcc actatctccc cttcctgccc       540
tcaactgagg acgtttacga ctgcagggtg gagcactggg gcttggatga gcctcttctc     600
aagcactggg agtttgatgc tccaagccct ctcccagaga ctacagagaa cgtcgacgga     660
ggtggcggcg gttaactga tacactccaa gcggagacag atcaacttga agacgagaag      720
tctgcgttgc agaccgagat tgccaatcta ctgaaagaga aggaaaaact ggagttcatc     780
ctggccgccc atggcctgaa cgacatcttc gaggcccaga gatcgagtg gcac            834

<210> SEQ ID NO 13
<211> LENGTH: 21
<212> TYPE: PRT
<213> ORGANISM: Artificial sequence
<220> FEATURE:
<223> OTHER INFORMATION: Gad derived peptide (552-572)

<400> SEQUENCE: 13

Asp Lys Val Asn Phe Phe Arg Met Val Ile Ser Asn Pro Ala Ala Thr
1               5                   10                  15

His Gln Asp Ile Asp
            20

<210> SEQ ID NO 14
<211> LENGTH: 10
<212> TYPE: PRT
<213> ORGANISM: Artificial sequence
<220> FEATURE:
<223> OTHER INFORMATION: GAD556-565 peptide

<400> SEQUENCE: 14

Phe Phe Arg Met Val Ile Ser Asn Pro Ala
1               5                   10

<210> SEQ ID NO 15
<211> LENGTH: 266
<212> TYPE: PRT
<213> ORGANISM: Homo sapiens

<400> SEQUENCE: 15

Met Val Cys Leu Lys Phe Pro Gly Gly Ser Cys Met Ala Ala Leu Thr
1               5                   10                  15

Val Thr Leu Met Val Leu Ser Ser Pro Leu Ala Leu Ala Gly Asp Thr
            20                  25                  30
```

Arg Pro Arg Phe Leu Glu Gln Val Lys His Glu Cys His Phe Phe Asn
            35                  40                  45

Gly Thr Glu Arg Val Arg Phe Leu Asp Arg Tyr Phe Tyr His Gln Glu
    50                  55                  60

Glu Tyr Val Arg Phe Asp Ser Asp Val Gly Glu Tyr Arg Ala Val Thr
65                  70                  75                  80

Glu Leu Gly Arg Pro Asp Ala Glu Tyr Trp Asn Ser Gln Lys Asp Leu
                85                  90                  95

Leu Glu Gln Lys Arg Ala Ala Val Asp Thr Tyr Cys Arg His Asn Tyr
            100                 105                 110

Gly Val Gly Glu Ser Phe Thr Val Gln Arg Arg Val Tyr Pro Glu Val
            115                 120                 125

Thr Val Tyr Pro Ala Lys Thr Gln Pro Leu Gln His His Asn Leu Leu
130                 135                 140

Val Cys Ser Val Asn Gly Phe Tyr Pro Gly Ser Ile Glu Val Arg Trp
145                 150                 155                 160

Phe Arg Asn Gly Gln Glu Glu Lys Thr Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Arg Ser Gly Glu Val Tyr Thr Cys Gln Val Glu His Pro Ser
            195                 200                 205

Leu Thr Ser Pro Leu Thr Val Glu Trp Arg Ala Arg Ser Glu Ser Ala
        210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
                245                 250                 255

Ser Gly Leu Gln Pro Thr Gly Phe Leu Ser
            260                 265

<210> SEQ ID NO 16
<211> LENGTH: 254
<212> TYPE: PRT
<213> ORGANISM: Homo sapiens

<400> SEQUENCE: 16

Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
            20                  25                  30

Ile Gln Ala Glu Phe Tyr Leu Asn Pro Asp Gln Ser Gly Glu Phe Met
        35                  40                  45

Phe Asp Phe Asp Gly Asp Glu Ile Phe His Val Asp Met Ala Lys Lys
    50                  55                  60

Glu Thr Val Trp Arg Leu Glu Glu Phe Gly Arg Phe Ala Ser Phe Glu
65                  70                  75                  80

Ala Gln Gly Ala Leu Ala Asn Ile Ala Val Asp Lys Ala Asn Leu Glu
                85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
            115                 120                 125

Val Leu Ile Cys Phe Ile Asp Lys Phe Thr Pro Pro Val Val Asn Val

```
                   130                 135                 140
Thr Trp Leu Arg Asn Gly Lys Pro Val Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
            180                 185                 190

Trp Gly Leu Asp Glu Pro Leu Leu Lys His Trp Glu Phe Asp Ala Pro
        195                 200                 205

Ser Pro Leu Pro Glu Thr Thr Glu Asn Val Val Cys Ala Leu Gly Leu
    210                 215                 220

Thr Val Gly Leu Val Gly Ile Ile Ile Gly Thr Ile Phe Ile Ile Lys
225                 230                 235                 240

Gly Leu Arg Lys Ser Asn Ala Ala Glu Arg Arg Gly Pro Leu
                245                 250

<210> SEQ ID NO 17
<211> LENGTH: 2824
<212> TYPE: DNA
<213> ORGANISM: Homo sapiens

<400> SEQUENCE: 17
gcggccgccc gcacttcccg cctctggctc gcccgaggac gcgctggcac gcctcccacc      60
ccctcactct gactccagct ggcgtgcatg gtctgcctcg catcctcacg actcagctcc     120
ctccctctct cgtgtttttt tcctccgccg ccccctcatt catccccact gggctccctt     180
tccctcaaat gctctggggc tctccgcgct ttcctgagtc cgggctccga ggacccttag     240
gtagtcccgg tctcttttaa agctccccgg cttccaaagg gttgccacgt ccctaaaccc     300
tgtctccagc tcgcatacac acacgcacag acacgcacgt tttctgttcc tgcgtgacac     360
ccgcccctcgc cgctcggccc cgccggtccc cgcgcggtgc cctcctcccg ccacacgggc     420
acgcacgcgc gcgcagggcc aagcccgagg cagctcgccc gcagctcgca ctcgcaggcg     480
acctgctcca gtctccaaag ccgatggcat ctccgggctc tggcttttgg tctttcgggt     540
cggaagatgg ctctggggat tccgagaatc ccggcacagc gcgagcctgg tgccaagtgg     600
ctcagaagtt cacgggcggc atcggaaaca aactgtgcgc cctgctctac ggagacgccg     660
agaagccggc ggagagcggc gggagccaac ccccgcgggc cgccgcccgg aaggccgcct     720
gcgcctgcga ccagaagccc tgcagctgct ccaaagtgga tgtcaactac gcgtttctcc     780
atgcaacaga cctgctgccg gcgtgtgatg agaaaggcc cactttggcg tttctgcaag     840
atgttatgaa catttttactt cagtatgtgg tgaaaagttt cgatagatca accaaagtga     900
ttgatttcca ttatcctaat gagcttctcc aagaatataa ttgggaattg gcagaccaac     960
cacaaaattt ggaggaaatt ttgatgcatt gccaaacaac tctaaaatat gcaattaaaa    1020
cagggcatcc tagatacttc aatcaacttt ctactggttt ggatatggtt ggattagcag    1080
cagactggct gacatcaaca gcaaatacta acatgttcac ctatgaaatt gctccagtat    1140
ttgtgctttt ggaatatgtc acactaaaga aaatgagaga atcattggc tggccagggg    1200
gctctggcga tgggatattt tctcccggtg gcgccatatc taacatgtat gccatgatga    1260
tcgcacgctt taagatgttc ccagaagtca aggagaaagg aatggctgct cttcccaggc    1320
tcattgcctt cacgtctgaa catagtcatt tttctctcaa gagggagct gcagccttag    1380
ggattggaac agacagcgtg attctgatta aatgtgatga gagagggaaa atgattccat    1440
```

```
ctgatcttga aagaaggatt cttgaagcca aacagaaagg gtttgttcct ttcctcgtga    1500
gtgccacagc tggaaccacc gtgtacgagc atttgaccc cctcttagct gtcgctgaca    1560
tttgcaaaaa gtataagatc tggatgcatg tggatgcagc ttggggtggg ggattactga    1620
tgtcccgaaa acacaagtgg aaactgagtg gcgtggagag ggccaactct gtgacgtgga    1680
atccacacaa gatgatggga gtccctttgc agtgctctgc tctcctggtt agagaagagg    1740
gattgatgca gaattgcaac caaatgcatg cctcctacct cttcagcaa gataaacatt    1800 atgacctgtc ctatgacact ggagacaagg ccttacagtg cggacgccac gttgatgttt    1860
ttaaactatg gctgatgtgg agggcaaagg ggactaccgg gtttgaagcg catgttgata    1920
aatgtttgga gttggcagag tatttataca acatcataaa aaaccgagaa ggatatgaga    1980
tggtgtttga tgggaagcct cagcacacaa atgtctgctt ctggtacatt cctccaagct    2040
tgcgtactct ggaagacaat gaagagagaa tgagtcgcct ctcgaaggtg gctccagtga    2100
ttaaagccag aatgatggag tatgaaccca caatggtcag ctaccaaccc ttgggagaca    2160
aggtcaattt cttccgcatg gtcatctcaa acccagcggc aactcaccaa gacattgact    2220
tcctgattga agaaatagaa cgccttggac aagatttata ataaccttgc tcaccaagct    2280
gttccacttc tctagagaac atgccctcag ctaagccccc tactgagaaa cttcctttga    2340
gaattgtgcg acttcacaaa atgcaaggtg aacaccactt tgtctctgag aacagacgtt    2400
accaattatg gagtgtcacc agctgccaaa atcgtaggtg ttggctctgc tggtcactgg    2460
agtagttgct actcttcaga atatggacaa agaaggcaca ggtgtaaata tagtagcagg    2520
atgaggaacc tcaaactggg tatcattttg cacgtgctct tctgttctca aatgctaaat    2580
gcaaacactg tgtatttatt agttaggtgt gccaaactac cgttcccaaa ttggtgtttc    2640
tgaatgacat caacattccc ccaacattac tccattacta aagacagaaa aaaataaaaa    2700
cataaaatat acaaacatgt ggcaacctgt tcttcctacc aaatataaac ttgtgtatga    2760
tccaagtatt ttatctgtgt tgtctctcta aacccaaata aatgtgtaaa tgtggacaca    2820
tctc                                                                2824

<210> SEQ ID NO 18
<211> LENGTH: 2419
<212> TYPE: DNA
<213> ORGANISM: Homo sapiens

<400> SEQUENCE: 18
gcggccgccc gcacttcccg cctctggctc gcccgaggac gcgctggcac gcctcccacc      60
ccctcactct gactccagct ggcgtgcatg gtctgcctcg catcctcacg actcagctcc     120
ctccctctct cgtgtttttt tcctccgccg cccctcatt catccccact gggctccctt      180
tccctcaaat gctctggggc tctccgcgct ttcctgagtc cgggctccga ggacccttag     240
gtagtcccgg tctcttttaa agctccccgg cttccaaagg gttgccacgt ccctaaaccc     300
tgtctccagc tcgcatacac acacgcacag acacgcacgt tttctgttcc tgcgtgacac     360
ccgccctcgc cgctcggccc cgccggtccc cgcgcggtgc cctcctcccg ccacacgggc     420
acgcacgcgc gcgcagggcc aagcccgagg cagctcgccc gcagtcgca ctcgcaggcg      480 acctgctcca gtctccaaag ccgatggcat ctccgggctc tggcttttgg tctttcgggt     540
cggaagatgg ctctggggat tccgagaatc ccggcacagc gcgagcctgg tgccaagtgg     600
ctcagaagtt cacgggcggc atcggaaaca aactgtgcgc cctgctctac ggagacgccg     660
agaagccggc ggagagcggc gggagccaac cccgcgggc cgccgcccgg aaggccgcct      720
```

```
gcgcctgcga ccagaagccc tgcagctgct ccaaagtgga tgtcaactac gcgtttctcc    780
atgcaacaga cctgctgccg gcgtgtgatg agaaaggcc cactttggcg tttctgcaag     840
atgttatgaa cattttactt cagtatgtgg tgaaaagttt cgatagatca accaaagtga    900
ttgatttcca ttatcctaat gagcttctcc aagaatataa ttgggaattg gcagaccaac    960
cacaaaattt ggaggaaatt ttgatgcatt gccaacaac tctaaaatat gcaattaaaa    1020
cagggcatcc tagatacttc aatcaacttt ctactggttt ggatatggtt ggattagcag   1080
cagactggct gacatcaaca gcaaatacta acatgttcac ctatgaaatt gctccagtat   1140
ttgtgctttt ggaatatgtc acactaaaga aaatgagaga atcattggc tggccagggg    1200
gctctggcga tgggatattt tctcccggtg gcgccatatc taacatgtat gccatgatga   1260
tcgcacgctt aagatgttc ccagaagtca aggagaaagg aatggctgct cttcccaggc    1320
tcattgcctt cacgtctgaa catagtcatt tttctctcaa gagggagct gcagccttag    1380
ggattggaac agacagcgtg attctgatta aatgtgatga gagagggaaa atgattccat   1440
ctgatcttga agaaggatt cttgaagcca acagaaagg gtttgttcct ttcctcgtga     1500
gtgccacagc tggaaccacc gtgtacgagc atttgacccc cctcttagct gtcgctgaca   1560
tttgcaaaaa gtataagatc tggatgcatg tggatgcagc ttggggtggg ggattactga   1620
tgtcccgaaa acacaagtgg aaactgagtg gcgtggagag ggccaactct gtgacgtgga   1680
atccacacaa gatgatggga gtccctttgc agtgctctgc tctcctggtt agagaagagg   1740
gattgatgca gaattgcaac caaatgcatg cctcctacct ctttcagcaa gataaacatt   1800
atgacctgtc ctatgacact ggagacaagg ccttacagtg cggacgccac gttgatgttt   1860
ttaaactatg gctgatgtgg agggcaaagg ggactaccgg gtttgaagcg catgttgata   1920
aatgtttgga gttggcagag tatttataca acatcataaa aaaccgagaa ggatatgaga   1980
tggtgtttga tgggaagcct cagcacacaa atgtctgctt ctggtacatt cctccaagct   2040
tgcgtactct ggaagacaat gaagagagaa tgagtcgcct ctcgaaggtg gctccagtga   2100
ttaaagccag aatgatggag tatgaaacca caatggtcag ctaccaaccc ttgggagaca   2160
aggtcaattt cttccgcatg gtcatctcaa acccagcggc aactcaccaa gacattgact   2220
tcctgattga agaaatagaa cgccttggac aagatttata ataaccttgc tcaccaagct   2280
gttccacttc tctaggtaga caattaagtt gtcacaaact gtgtgaatgt atttgtagtt   2340
tgttccaaag taaatctatt tctatattgt ggtgtcaaag tagagtttaa aaattaaaca   2400
aaaaagacat tgctcctttt                                              2419
```

<210> SEQ ID NO 19
<211> LENGTH: 585
<212> TYPE: PRT
<213> ORGANISM: Homo sapiens

<400> SEQUENCE: 19

Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
    50                  55                  60

```
Arg Ala Ala Ala Arg Lys Ala Ala Cys Ala Cys Asp Gln Lys Pro Cys
 65                  70                  75                  80

Ser Cys Ser Lys Val Asp Val Asn Tyr Ala Phe Leu His Ala Thr Asp
                 85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
        355                 360                 365

Gly Gly Leu Leu Met Ser Arg Lys His Lys Trp Lys Leu Ser Gly Val
    370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Gly Leu Met Gln
                405                 410                 415

Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
        435                 440                 445

His Val Asp Val Phe Lys Leu Trp Leu Met Trp Arg Ala Lys Gly Thr
    450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
```

```
                485              490              495
Gly Lys Pro Gln His Thr Asn Val Cys Phe Trp Tyr Ile Pro Pro Ser
            500                  505                  510

Leu Arg Thr Leu Glu Asp Asn Glu Glu Arg Met Ser Arg Leu Ser Lys
            515                  520                  525

Val Ala Pro Val Ile Lys Ala Arg Met Met Glu Tyr Gly Thr Thr Met
            530                  535                  540

Val Ser Tyr Gln Pro Leu Gly Asp Lys Val Asn Phe Phe Arg Met Val
545                 550                  555                  560

Ile Ser Asn Pro Ala Ala Thr His Gln Asp Ile Asp Phe Leu Ile Glu
                565                  570                  575

Glu Ile Glu Arg Leu Gly Gln Asp Leu
            580                  585

<210> SEQ ID NO 20
<211> LENGTH: 3488
<212> TYPE: DNA
<213> ORGANISM: Homo sapiens

<400> SEQUENCE: 20
gcaaaaccgt gagctggatt tataatcgcc ctataaagct ccagaggcgg tcaggcacct      60
gcagaggagc cccgccgctc cgccgactag ctgcccccgc gagcaacggc ctcgtgattt     120
ccccgccgat ccggtccccg cctcccact  ctgcccccgc ctaccccgga gccgtgcagc     180
cgcctctccg aatctctctc ttctcctggc gctcgcgtgc gagagggaac tagcgagaac     240
gaggaagcag ctggaggtga cgccgggcag attacgcctg tcaggccgga ccgagcggga    300
tcgctgggcg ctgtgcagag gaaaggcggg agtgcccggc tcgctgtcgc agagccgagc    360
ctgtttctgc gccggaccag tcgaggactc tggacagtag aggcccgggg acgaccgagc    420
tgatggcgtc ttcgacccca tcttcgtccg caacctcctc gaacgcggga gcggacccca    480
ataccactaa cctgcgcccc acaacgtacg ataccggtg cggcgtggcc catggatgca     540
ccagaaaact ggggctcaag atctgcggct tcttgcaaag gaccaacagc tggaagaga     600
agagtcgcct tgtgagtgcc ttcaaggaga ggcaatcctc caagaacctg ctttcctgtg    660
aaaacagcga ccgggatgcc cgcttccggc gcacagagac tgacttctct aatctgtttg    720
ctagagatct gcttccggct aagaacggtg aggagcaaac cgtgcaattc ctcctggaag    780
tggtggacat actcctcaac tatgtccgca agacatttga tcgctccacc aaggtgctgg    840
actttcatca cccacaccag ttgctggaag catggaggg cttcaacttg agctctctg     900
accacccga gtccctggag cagatcctgg ttgactgcag agacaccttg aagtatgggg    960
ttcgcacagg tcatcctcga ttttcaacc agctctccac tggattggat attattggcc    1020
tagctggaga atggctgaca tcaacggcca ataccaacat gtttacatat gaaattgcac   1080
cagtgtttgt cctcatggaa caaataacac ttaagaagat gagagagata gttgatggt    1140
caagtaaaga tggtgatggg atattttctc ctggggcgc catatccaac atgtacagca    1200
tcatggctgc tcgctacaag tacttcccgg aagttaagac aaagggcatg gcggctgtgc   1260
ctaaactggt cctcttcacc tcagaacaga gtcactattc cataaagaaa gctgggctg    1320
cacttggctt tggaactgac aatgtgattt tgataaagtg caatgaaagg gggaaaataa   1380
ttccagctga ttttgaggca aaaattcttg aagccaaaca gaagggatat gttcccttt    1440
atgtcaatgc aactgctggc acgactgttt atggagcttt tgatccgata caagagattg   1500
cagatatatg tgagaaatat aacctttggt tgcatgtcga tgctgcctgg ggaggtgggc   1560
```

-continued

```
tgctcatgtc caggaagcac cgccataaac tcaacggcat agaaagggcc aactcagtca      1620
cctggaaccc tcacaagatg atgggcgtgc tgttgcagtg ctctgccatt ctcgtcaagg      1680
aaaagggtat actccaagga tgcaaccaga tgtgtgcagg atacctcttc cagccagaca      1740
agcagtatga tgtctcctac gacaccgggg acaaggcaat tcagtgtggc cgccacgtgg      1800
atatcttcaa gttctggctg atgtggaaag caagggcac agtgggattt gaaaaccaga      1860
tcaacaaatg cctggaactg gctgaatacc tctatgccaa gattaaaaac agagaagaat      1920
ttgagatggt tttcaatggc gagcctgagc acacaaacgt ctgttttggt tatattccac      1980
aaagcctcag gggtgtgcca gacagccctc aacgacggga aaagctacac aaggtggctc      2040
caaaaatcaa agccctgatg atggagtcag gtacgaccat ggttggctac cagccccaag      2100
gggacaaggc caacttcttc cggatggtca tctccaaccc agccgctacc cagtctgaca      2160
ttgacttcct cattgaggag atagaaagac tgggccagga tctgtaatca tccttcgcag      2220
aacatgagtt tatgggaatg cctttttccct ctggcactcc agaacaaacc tctatatgtt      2280
gctgaaacac acaggccatt tcattgaggg aaaacataat atcttgaaga atattgttaa      2340
aaccttactt aaagcttgtt tgttctagtt agcaggaaat agtgttcttt ttaaaaagtt      2400
gcacattagg aacagagtat atatgtacag ttatacatac ctctctctat atatacatgt      2460
atagtgagtg tggcttagta atagatcacg gcatgtttcc cgctccaaga gaattcactt      2520
taccttcagc agttaccgag gagctaaaca tgctgccaac cagcttgtcc aacaactcca      2580
ggaaaactgt ttttcaaaac gccatgtcct aggggccaag ggaaatgctg ttggtgagaa      2640
tcgacctcac tgtcagcgtt tctccacctg aagtgatgat ggatgagaaa aaacaccacc      2700
aaatgacaag tcacaccctc cccattagta tcctgttagg ggaaaatagt agcagagtca      2760 tgttacagg tgtactatgg ctgtattttt agagattaat ttgtgtagat tgtgtaaatt      2820
cctgttgtct gaccttggtg gtgggagggg gagactatgt gtcatgattt caatgattgt      2880
ttaattgtag gtcaatgaaa tatttgctta tttatattca gagatgtacc atgttaaaga      2940
ggcgtcttgt attttcttcc catttgtaat gtatcttatt tatatatgaa gtaagttctg      3000
aaaactgttt atggtatttt cgtgcatttg tgagccaaag agaaaagatt aaaattagtg      3060
agatttgtat ttatattaga gtgcccttaa aataatgatt taagcatttt actgtctgta      3120
agagaattct aagattgtac ataaagtcat atatatggaa atcctgttac ttaaatagca      3180
tctgctcttc tcttacgctc tctgtctggc tgtacgtctg gtgttctcaa tgcttttcta      3240
gcaactgttg gataataact agatctcctg taattttgta gtagttgatg accaatctct      3300
gtgactcgct tagctgaaac ctaaggcaac atttccgaag accttctgaa gatctcagat      3360
aaagtgacca ggctcacaac tgtttttgaa gaagggaaat tcacactgtg cgttttagag      3420
tatgcaagaa gaatataaat aaataaaaat attctccatg gagaatttga acaaaaaaaa      3480
aaaaaaaa                                                              3488
```

<210> SEQ ID NO 21
<211> LENGTH: 594
<212> TYPE: PRT
<213> ORGANISM: Homo sapiens

<400> SEQUENCE: 21

Met Ala Ser Ser Thr Pro Ser Ser Ser Ala Thr Ser Ser Asn Ala Gly
1               5                   10                  15

Ala Asp Pro Asn Thr Thr Asn Leu Arg Pro Thr Thr Tyr Asp Thr Trp

-continued

```
                    20                  25                  30
        Cys Gly Val Ala His Gly Cys Thr Arg Lys Leu Gly Leu Lys Ile Cys
                    35                  40                  45
        Gly Phe Leu Gln Arg Thr Asn Ser Leu Glu Glu Lys Ser Arg Leu Val
                    50                  55                  60
        Ser Ala Phe Lys Glu Arg Gln Ser Ser Lys Asn Leu Leu Ser Cys Glu
         65                  70                  75                  80
        Asn Ser Asp Arg Asp Ala Arg Phe Arg Arg Thr Glu Thr Asp Phe Ser
                            85                  90                  95
        Asn Leu Phe Ala Arg Asp Leu Leu Pro Ala Lys Asn Gly Glu Glu Gln
                            100                 105                 110
        Thr Val Gln Phe Leu Leu Glu Val Val Asp Ile Leu Leu Asn Tyr Val
                            115                 120                 125
        Arg Lys Thr Phe Asp Arg Ser Thr Lys Val Leu Asp Phe His His Pro
                    130                 135                 140
        His Gln Leu Leu Glu Gly Met Glu Gly Phe Asn Leu Glu Leu Ser Asp
        145                 150                 155                 160
        His Pro Glu Ser Leu Glu Gln Ile Leu Val Asp Cys Arg Asp Thr Leu
                            165                 170                 175
        Lys Tyr Gly Val Arg Thr Gly His Pro Arg Phe Phe Asn Gln Leu Ser
                            180                 185                 190
        Thr Gly Leu Asp Ile Ile Gly Leu Ala Gly Glu Trp Leu Thr Ser Thr
                            195                 200                 205
        Ala Asn Thr Asn Met Phe Thr Tyr Glu Ile Ala Pro Val Phe Val Leu
                    210                 215                 220
        Met Glu Gln Ile Thr Leu Lys Lys Met Arg Glu Ile Val Gly Trp Ser
        225                 230                 235                 240
        Ser Lys Asp Gly Asp Gly Ile Phe Ser Pro Gly Gly Ala Ile Ser Asn
                            245                 250                 255
        Met Tyr Ser Ile Met Ala Ala Arg Tyr Lys Tyr Phe Pro Glu Val Lys
                            260                 265                 270
        Thr Lys Gly Met Ala Ala Val Pro Lys Leu Val Leu Phe Thr Ser Glu
                            275                 280                 285
        Gln Ser His Tyr Ser Ile Lys Lys Ala Gly Ala Ala Leu Gly Phe Gly
                    290                 295                 300
        Thr Asp Asn Val Ile Leu Ile Lys Cys Asn Glu Arg Gly Lys Ile Ile
        305                 310                 315                 320
        Pro Ala Asp Phe Glu Ala Lys Ile Leu Glu Ala Lys Gln Lys Gly Tyr
                            325                 330                 335
        Val Pro Phe Tyr Val Asn Ala Thr Ala Gly Thr Thr Val Tyr Gly Ala
                            340                 345                 350
        Phe Asp Pro Ile Gln Glu Ile Ala Asp Ile Cys Glu Lys Tyr Asn Leu
                    355                 360                 365
        Trp Leu His Val Asp Ala Ala Trp Gly Gly Gly Leu Leu Met Ser Arg
                    370                 375                 380
        Lys His Arg His Lys Leu Asn Gly Ile Glu Arg Ala Asn Ser Val Thr
        385                 390                 395                 400
        Trp Asn Pro His Lys Met Met Gly Val Leu Leu Gln Cys Ser Ala Ile
                            405                 410                 415
        Leu Val Lys Glu Lys Gly Ile Leu Gln Gly Cys Asn Gln Met Cys Ala
                            420                 425                 430
        Gly Tyr Leu Phe Gln Pro Asp Lys Gln Tyr Asp Val Ser Tyr Asp Thr
                            435                 440                 445
```

```
Gly Asp Lys Ala Ile Gln Cys Gly Arg His Val Asp Ile Phe Lys Phe
        450                 455                 460

Trp Leu Met Trp Lys Ala Lys Gly Thr Val Gly Phe Glu Asn Gln Ile
465                 470                 475                 480

Asn Lys Cys Leu Glu Leu Ala Glu Tyr Leu Tyr Ala Lys Ile Lys Asn
                485                 490                 495

Arg Glu Glu Phe Glu Met Val Phe Asn Gly Glu Pro Glu His Thr Asn
            500                 505                 510

Val Cys Phe Trp Tyr Ile Pro Gln Ser Leu Arg Gly Val Pro Asp Ser
        515                 520                 525

Pro Gln Arg Arg Glu Lys Leu His Lys Val Ala Pro Lys Ile Lys Ala
        530                 535                 540

Leu Met Met Glu Ser Gly Thr Thr Met Val Gly Tyr Gln Pro Gln Gly
545                 550                 555                 560

Asp Lys Ala Asn Phe Phe Arg Met Val Ile Ser Asn Pro Ala Ala Thr
                565                 570                 575

Gln Ser Asp Ile Asp Phe Leu Ile Glu Ile Glu Arg Leu Gly Gln
            580                 585                 590

Asp Leu

<210> SEQ ID NO 22
<211> LENGTH: 13
<212> TYPE: PRT
<213> ORGANISM: Artificial sequence
<220> FEATURE:
<223> OTHER INFORMATION: GAD555-567 peptide

<400> SEQUENCE: 22

Asn Phe Phe Arg Met Val Ile Ser Asn Pro Ala Ala Thr
1               5                   10

<210> SEQ ID NO 23
<211> LENGTH: 60
<212> TYPE: PRT
<213> ORGANISM: Artificial sequence
<220> FEATURE:
<223> OTHER INFORMATION: Exemplary linker peptide
<220> FEATURE:
<221> NAME/KEY: misc_feature
<222> LOCATION: (3)..(4)
<223> OTHER INFORMATION: may be missing
<220> FEATURE:
<221> NAME/KEY: misc_feature
<222> LOCATION: (5)..(6)
<223> OTHER INFORMATION: may be missing
<220> FEATURE:
<221> NAME/KEY: misc_feature
<222> LOCATION: (7)..(8)
<223> OTHER INFORMATION: may be missing
<220> FEATURE:
<221> NAME/KEY: misc_feature
<222> LOCATION: (9)..(10)
<223> OTHER INFORMATION: may be missing
<220> FEATURE:
<221> NAME/KEY: misc_feature
<222> LOCATION: (11)..(12)
<223> OTHER INFORMATION: may be missing
<220> FEATURE:
<221> NAME/KEY: misc_feature
<222> LOCATION: (13)..(14)
<223> OTHER INFORMATION: may be missing
<220> FEATURE:
<221> NAME/KEY: misc_feature
<222> LOCATION: (15)..(16)
<223> OTHER INFORMATION: may be missing
<220> FEATURE:
```

```
<221> NAME/KEY: misc_feature
<222> LOCATION: (17)..(18)
<223> OTHER INFORMATION: may be missing
<220> FEATURE:
<221> NAME/KEY: misc_feature
<222> LOCATION: (19)..(20)
<223> OTHER INFORMATION: may be missing
<220> FEATURE:
<221> NAME/KEY: misc_feature
<222> LOCATION: (21)..(22)
<223> OTHER INFORMATION: may be missing
<220> FEATURE:
<221> NAME/KEY: misc_feature
<222> LOCATION: (23)..(24)
<223> OTHER INFORMATION: may be missing
<220> FEATURE:
<221> NAME/KEY: misc_feature
<222> LOCATION: (25)..(26)
<223> OTHER INFORMATION: may be missing
<220> FEATURE:
<221> NAME/KEY: misc_feature
<222> LOCATION: (27)..(28)
<223> OTHER INFORMATION: may be missing
<220> FEATURE:
<221> NAME/KEY: misc_feature
<222> LOCATION: (29)..(30)
<223> OTHER INFORMATION: may be missing
<220> FEATURE:
<221> NAME/KEY: misc_feature
<222> LOCATION: (31)..(32)
<223> OTHER INFORMATION: may be missing
<220> FEATURE:
<221> NAME/KEY: misc_feature
<222> LOCATION: (33)..(34)
<223> OTHER INFORMATION: may be missing
<220> FEATURE:
<221> NAME/KEY: misc_feature
<222> LOCATION: (35)..(36)
<223> OTHER INFORMATION: may be missing
<220> FEATURE:
<221> NAME/KEY: misc_feature
<222> LOCATION: (37)..(38)
<223> OTHER INFORMATION: may be missing
<220> FEATURE:
<221> NAME/KEY: misc_feature
<222> LOCATION: (39)..(40)
<223> OTHER INFORMATION: may be missing
<220> FEATURE:
<221> NAME/KEY: misc_feature
<222> LOCATION: (41)..(42)
<223> OTHER INFORMATION: may be missing
<220> FEATURE:
<221> NAME/KEY: misc_feature
<222> LOCATION: (43)..(44)
<223> OTHER INFORMATION: may be missing
<220> FEATURE:
<221> NAME/KEY: misc_feature
<222> LOCATION: (45)..(46)
<223> OTHER INFORMATION: may be missing
<220> FEATURE:
<221> NAME/KEY: misc_feature
<222> LOCATION: (47)..(48)
<223> OTHER INFORMATION: may be missing
<220> FEATURE:
<221> NAME/KEY: misc_feature
<222> LOCATION: (49)..(50)
<223> OTHER INFORMATION: may be missing
<220> FEATURE:
<221> NAME/KEY: misc_feature
<222> LOCATION: (51)..(52)
<223> OTHER INFORMATION: may be missing
<220> FEATURE:
<221> NAME/KEY: misc_feature
<222> LOCATION: (53)..(54)
<223> OTHER INFORMATION: may be missing
<220> FEATURE:
<221> NAME/KEY: misc_feature
<222> LOCATION: (55)..(56)
<223> OTHER INFORMATION: may be missing
```

-continued

<220> FEATURE:
<221> NAME/KEY: misc_feature
<222> LOCATION: (57)..(58)
<223> OTHER INFORMATION: may be missing
<220> FEATURE:
<221> NAME/KEY: misc_feature
<222> LOCATION: (59)..(60)
<223> OTHER INFORMATION: may be missing

<400> SEQUENCE: 23

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
            20                  25                  30

Gly Ser Gly Ser Gly Ser Gly Ser Gly Ser Gly Ser Gly Ser Gly Ser
        35                  40                  45

Gly Ser Gly Ser Gly Ser Gly Ser Gly Ser Gly Ser
    50                  55                  60

<210> SEQ ID NO 24
<211> LENGTH: 30
<212> TYPE: PRT
<213> ORGANISM: Artificial sequence
<220> FEATURE:
<223> OTHER INFORMATION: Exemplary linker peptide
<220> FEATURE:
<221> NAME/KEY: misc_feature
<222> LOCATION: (6)..(10)
<223> OTHER INFORMATION: may be missing
<220> FEATURE:
<221> NAME/KEY: misc_feature
<222> LOCATION: (11)..(15)
<223> OTHER INFORMATION: may be missing
<220> FEATURE:
<221> NAME/KEY: misc_feature
<222> LOCATION: (16)..(20)
<223> OTHER INFORMATION: may be missing
<220> FEATURE:
<221> NAME/KEY: misc_feature
<222> LOCATION: (21)..(25)
<223> OTHER INFORMATION: may be missing
<220> FEATURE:
<221> NAME/KEY: misc_feature
<222> LOCATION: (26)..(30)
<223> OTHER INFORMATION: may be missing

<400> SEQUENCE: 24

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 25
<211> LENGTH: 15
<212> TYPE: PRT
<213> ORGANISM: Artificial sequence
<220> FEATURE:
<223> OTHER INFORMATION: Exemplary linker peptide

<400> SEQUENCE: 25

Gly Gly Gly Ser Leu Val Pro Arg Gly Ser Gly Gly Gly Gly Ser
1               5                   10                  15

<210> SEQ ID NO 26
<211> LENGTH: 16
<212> TYPE: PRT
<213> ORGANISM: Artificial sequence
<220> FEATURE:
<223> OTHER INFORMATION: Exemplary linker peptide

<400> SEQUENCE: 26

Gly Gly Gly Gly Ser Leu Val Pro Arg Gly Ser Gly Gly Gly Gly Ser
1               5                   10                  15

<210> SEQ ID NO 27
<211> LENGTH: 198
<212> TYPE: PRT
<213> ORGANISM: Homo sapiens

<400> SEQUENCE: 27

Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
                20                  25                  30

His Gln Glu Glu Tyr Val Arg Phe Asp Ser Asp Val Gly Glu Tyr Arg
            35                  40                  45

Ala Val Thr Glu Leu Gly Arg Pro Asp Ala Glu Tyr Trp Asn Ser Gln
        50                  55                  60

Lys Asp Leu Leu Glu Gln Lys Arg Ala Ala Val Asp Thr Tyr Cys Arg
65                  70                  75                  80

His Asn Tyr Gly Val Gly Glu Ser Phe Thr Val Gln Arg Arg Val Tyr
                85                  90                  95

Pro Glu Val Thr Val Tyr Pro Ala Lys Thr Gln Pro Leu Gln His His
            100                 105                 110

Asn Leu Leu Val Cys Ser Val Asn Gly Phe Tyr Pro Gly Ser Ile Glu
        115                 120                 125

Val Arg Trp Phe Arg Asn Gly Gln Glu Glu Lys Thr Gly Val Val Ser
130                 135                 140

Thr Gly Leu Ile Gln Asn Gly Asp Trp Thr Phe Gln Thr Leu Val Met
145                 150                 155                 160

Leu Glu Thr Val Pro Arg Ser Gly Glu Val Tyr Thr Cys Gln Val Glu
                165                 170                 175

His Pro Ser Leu Thr Ser Pro Leu Thr Val Glu Trp Arg Ala Arg Ser
            180                 185                 190

Glu Ser Ala Gln Ser Lys
        195

<210> SEQ ID NO 28
<211> LENGTH: 594
<212> TYPE: DNA
<213> ORGANISM: Homo sapiens

<400> SEQUENCE: 28
ggggacaccc gaccacgttt cttggagcag gttaaacatg agtgtcattt cttcaacggg    60
acggagcggg tgcggttcct ggacagatac ttctatcacc aagaggagta cgtgcgcttc   120
gacagcgacg tgggggagta ccgggcggtg acggagctgg gcggccctga tgccgagtac   180
tggaacagcc agaaggacct cctggagcag aagcgggccg cggtggacac ctactgcaga   240
cacaactacg ggttggtga gagcttcaca gtgcagcggc gagtctatcc tgaggtgact   300
gtgtatcctg caaagaccca gcccctgcag caccacaacc tcctggtctg ctctgtgaat   360
ggtttctatc caggcagcat tgaagtcagg tggttccgga acggccagga agagaagact   420
ggggtggtgt ccacaggcct gatccagaat ggagactgga ccttccagac cctggtgatg   480
ctggaaacag ttcctcggag tggagaggtt tacacctgcc aagtggagca cccaagcctg   540
acgagccctc tcacagtgga atggagagca cggtctgaat ctgcacagag caag    594

<210> SEQ ID NO 29
<211> LENGTH: 39
<212> TYPE: DNA
<213> ORGANISM: Artificial sequence
<220> FEATURE:
<223> OTHER INFORMATION: GAD peptide coding polynucleotide sequence

<400> SEQUENCE: 29
aacttctttc gtatggttat cagcaatcca gctgcgact    39

<210> SEQ ID NO 30
<211> LENGTH: 13
<212> TYPE: PRT
<213> ORGANISM: Artificial sequence
<220> FEATURE:
<223> OTHER INFORMATION: HA307-319 peptide

<400> SEQUENCE: 30

Pro Lys Tyr Val Lys Gln Asn Thr Leu Lys Leu Ala Thr
1               5                   10

<210> SEQ ID NO 31
<211> LENGTH: 15
<212> TYPE: PRT
<213> ORGANISM: Artificial sequence
<220> FEATURE:
<223> OTHER INFORMATION: InsA1-15  peptide

<400> SEQUENCE: 31

Gly Ile Val Glu Gln Cys Cys Thr Ser Ile Cys Ser Leu Tyr Gln
1               5                   10                  15

<210> SEQ ID NO 32
<211> LENGTH: 13
<212> TYPE: PRT
<213> ORGANISM: Artificial sequence
<220> FEATURE:
<223> OTHER INFORMATION: CII261-273 peptide

<400> SEQUENCE: 32

Ala Gly Phe Lys Gly Glu Gln Gly Pro Lys Gly Glu Pro
1               5                   10

<210> SEQ ID NO 33
<211> LENGTH: 13
<212> TYPE: PRT
<213> ORGANISM: Artificial sequence
<220> FEATURE:
<223> OTHER INFORMATION: GAD65 APL M559Z peptide

<400> SEQUENCE: 33

Asn Phe Phe Arg Glx Val Ile Ser Asn Pro Ala Ala Thr
1               5                   10

<210> SEQ ID NO 34
<211> LENGTH: 13
<212> TYPE: PRT
<213> ORGANISM: Artificial sequence
<220> FEATURE:
<223> OTHER INFORMATION: GAD65 APL I561M peptide

<400> SEQUENCE: 34

Asn Phe Phe Arg Met Val Met Ser Asn Pro Ala Ala Thr
1               5                   10

<210> SEQ ID NO 35
<211> LENGTH: 13
<212> TYPE: PRT
<213> ORGANISM: Artificial sequence
<220> FEATURE:
<223> OTHER INFORMATION: GAD65 APL N563Q peptide

<400> SEQUENCE: 35

Asn Phe Phe Arg Met Val Ile Ser Gln Pro Ala Ala Thr
1               5                   10

<210> SEQ ID NO 36
<211> LENGTH: 13
<212> TYPE: PRT
<213> ORGANISM: Artificial sequence
<220> FEATURE:
<223> OTHER INFORMATION: GAD65 APL I561M-N563Q peptide

<400> SEQUENCE: 36

Asn Phe Phe Arg Met Val Met Ser Gln Pro Ala Ala Thr
1               5                   10

<210> SEQ ID NO 37
<211> LENGTH: 11
<212> TYPE: PRT
<213> ORGANISM: Artificial sequence
<220> FEATURE:
<223> OTHER INFORMATION: G3H8 light chain CDR1

<400> SEQUENCE: 37

Arg Ala Ser Gln Ser Val Gly Ser Asn Leu Ala
1               5                   10

<210> SEQ ID NO 38
<211> LENGTH: 7
<212> TYPE: PRT
<213> ORGANISM: Artificial sequence
<220> FEATURE:
<223> OTHER INFORMATION: G3H8 light chain CDR2

<400> SEQUENCE: 38

Asp Ala Ser Thr Arg Ala Thr
1               5

<210> SEQ ID NO 39
<211> LENGTH: 9
<212> TYPE: PRT
<213> ORGANISM: Artificial sequence
<220> FEATURE:
<223> OTHER INFORMATION: G3H8 light chain CDR3

<400> SEQUENCE: 39

His Gln Tyr Gly Ser Ser Pro Arg Thr
1               5

<210> SEQ ID NO 40
<211> LENGTH: 33
<212> TYPE: DNA
<213> ORGANISM: Artificial sequence
<220> FEATURE:
<223> OTHER INFORMATION: G3H8 light chain CDR1 nucleotide sequence

<400> SEQUENCE: 40
agggccagtc agagtgttgg cagcaactta gcc                              33

<210> SEQ ID NO 41

```
<211> LENGTH: 21
<212> TYPE: DNA
<213> ORGANISM: Artificial sequence
<220> FEATURE:
<223> OTHER INFORMATION: G3H8 light chain CDR2 nucleotide sequence

<400> SEQUENCE: 41
gatgcatcca ccagggccac t                                              21

<210> SEQ ID NO 42
<211> LENGTH: 27
<212> TYPE: DNA
<213> ORGANISM: Artificial sequence
<220> FEATURE:
<223> OTHER INFORMATION: G3H8 light chain CDR3 nucleotide sequence

<400> SEQUENCE: 42
caccagtatg gtagctcacc tcggacg                                        27

<210> SEQ ID NO 43
<211> LENGTH: 10
<212> TYPE: PRT
<213> ORGANISM: Artificial sequence
<220> FEATURE:
<223> OTHER INFORMATION: G3H8 heavy chain CDR1

<400> SEQUENCE: 43

Gly Tyr Thr Phe Thr Thr Tyr Gly Ile Ser
1               5                   10

<210> SEQ ID NO 44
<211> LENGTH: 17
<212> TYPE: PRT
<213> ORGANISM: Artificial sequence
<220> FEATURE:
<223> OTHER INFORMATION: G3H8 heavy chain CDR2

<400> SEQUENCE: 44

Trp Ile Ser Ala Tyr Asn Gly His Thr Asn Tyr Ala Gln Met Leu Gln
1               5                   10                  15

Gly

<210> SEQ ID NO 45
<211> LENGTH: 15
<212> TYPE: PRT
<213> ORGANISM: Artificial sequence
<220> FEATURE:
<223> OTHER INFORMATION: G3H8 heavy chain CDR3

<400> SEQUENCE: 45

Glu Ala Tyr Ala Ser Tyr Gly Ser Gly Ser Tyr Trp Thr Asp Tyr
1               5                   10                  15

<210> SEQ ID NO 46
<211> LENGTH: 30
<212> TYPE: DNA
<213> ORGANISM: Artificial sequence
<220> FEATURE:
<223> OTHER INFORMATION: G3H8 heavy chain CDR1 nucleotide sequence

<400> SEQUENCE: 46
ggttacacct ttaccaccta tggtatcagc                                     30

<210> SEQ ID NO 47
<211> LENGTH: 51
<212> TYPE: DNA
```

<213> ORGANISM: Artificial sequence
<220> FEATURE:
<223> OTHER INFORMATION: G3H8 heavy chain CDR2 nucleotide sequence

<400> SEQUENCE: 47
tggatcagcg cttacaatgg tcacacaaac tatgcacaga tgctccaggg c           51

<210> SEQ ID NO 48
<211> LENGTH: 45
<212> TYPE: DNA
<213> ORGANISM: Artificial sequence
<220> FEATURE:
<223> OTHER INFORMATION: G3H8 heavy chain CDR3 nucleotide sequence

<400> SEQUENCE: 48
gaggcctatg cttcctatgg ttcggggagt tattggactg actac                  45

<210> SEQ ID NO 49
<211> LENGTH: 13
<212> TYPE: PRT
<213> ORGANISM: Artificial sequence
<220> FEATURE:
<223> OTHER INFORMATION: G1H12 light chain CDR1

<400> SEQUENCE: 49

Ser Gly Ser Ser Ser Asn Ile Gly Asn Asn Tyr Val Ser
1               5                   10

<210> SEQ ID NO 50
<211> LENGTH: 7
<212> TYPE: PRT
<213> ORGANISM: Artificial sequence
<220> FEATURE:
<223> OTHER INFORMATION: G1H12 light chain CDR2

<400> SEQUENCE: 50

Asp Asn Asn Lys Arg Pro Ser
1               5

<210> SEQ ID NO 51
<211> LENGTH: 11
<212> TYPE: PRT
<213> ORGANISM: Artificial sequence
<220> FEATURE:
<223> OTHER INFORMATION: G1H12 light chain CDR3

<400> SEQUENCE: 51

Gly Thr Trp Asp Ser Ser Leu Ser Val Trp Val
1               5                   10

<210> SEQ ID NO 52
<211> LENGTH: 39
<212> TYPE: DNA
<213> ORGANISM: Artificial sequence
<220> FEATURE:
<223> OTHER INFORMATION: G1H12 light chain CDR1 nucleotide sequence

<400> SEQUENCE: 52
tctggaagca gctccaacat tgggaataat tatgtatcc                         39

<210> SEQ ID NO 53
<211> LENGTH: 21
<212> TYPE: DNA
<213> ORGANISM: Artificial sequence
<220> FEATURE:
<223> OTHER INFORMATION: G1H12 light chain CDR2 nucleotide sequence

<400> SEQUENCE: 53
gacaataata agcgaccctc a                                                    21

<210> SEQ ID NO 54
<211> LENGTH: 33
<212> TYPE: DNA
<213> ORGANISM: Artificial sequence
<220> FEATURE:
<223> OTHER INFORMATION: G1H12 light chain CDR3 nucleotide sequence

<400> SEQUENCE: 54
ggaacatggg atagcagcct gagtgtctgg gtg                                       33

<210> SEQ ID NO 55
<211> LENGTH: 10
<212> TYPE: PRT
<213> ORGANISM: Artificial sequence
<220> FEATURE:
<223> OTHER INFORMATION: G1H12 heavy chain CDR1

<400> SEQUENCE: 55

Gly Tyr Thr Phe Thr Ser Tyr Gly Ile Ser
1               5                   10

<210> SEQ ID NO 56
<211> LENGTH: 17
<212> TYPE: PRT
<213> ORGANISM: Artificial sequence
<220> FEATURE:
<223> OTHER INFORMATION: G1H12 heavy chain CDR2

<400> SEQUENCE: 56

Gly Ile Ile Pro Ile Phe Gly Thr Ala Asn Tyr Ala Gln Lys Phe Gln
1               5                   10                  15

Gly

<210> SEQ ID NO 57
<211> LENGTH: 14
<212> TYPE: PRT
<213> ORGANISM: Artificial sequence
<220> FEATURE:
<223> OTHER INFORMATION: G1H12 heavy chain CDR3

<400> SEQUENCE: 57

Asp Pro Gln Ser Tyr Tyr Tyr Asp Ser Ser Gly Phe Asp Tyr
1               5                   10

<210> SEQ ID NO 58
<211> LENGTH: 30
<212> TYPE: DNA
<213> ORGANISM: Artificial sequence
<220> FEATURE:
<223> OTHER INFORMATION: G1H12 heavy chain CDR1 nucleotide sequence

<400> SEQUENCE: 58
ggttacacct ttaccagcta tggtatcagc                                           30

<210> SEQ ID NO 59
<211> LENGTH: 51
<212> TYPE: DNA
<213> ORGANISM: Artificial sequence
<220> FEATURE:
<223> OTHER INFORMATION: G1H12 heavy chain CDR2 nucleotide sequence

<400> SEQUENCE: 59

```
gggatcatcc ctatctttgg tacagcaaac tacgcacaga agttccaggg c         51
```

```
<210> SEQ ID NO 60
<211> LENGTH: 42
<212> TYPE: DNA
<213> ORGANISM: Artificial sequence
<220> FEATURE:
<223> OTHER INFORMATION: G1H12 heavy chain CDR3 nucleotide sequence

<400> SEQUENCE: 60
gatccccagt cctattacta tgatagtagt ggttttgact ac                  42
```

```
<210> SEQ ID NO 61
<211> LENGTH: 17
<212> TYPE: PRT
<213> ORGANISM: Artificial sequence
<220> FEATURE:
<223> OTHER INFORMATION: Diabetes-associated autoantigenic peptide

<400> SEQUENCE: 61
```

Val Asn Phe Phe Arg Met Val Ile Ser Asn Pro Ala Ala Thr His Gln
1               5                   10                  15

Asp

```
<210> SEQ ID NO 62
<211> LENGTH: 21
<212> TYPE: PRT
<213> ORGANISM: Artificial sequence
<220> FEATURE:
<223> OTHER INFORMATION: Diabetes-associated autoantigenic peptide

<400> SEQUENCE: 62
```

Asp Lys Val Asn Phe Phe Arg Met Val Ile Ser Asn Pro Ala Ala Thr
1               5                   10                  15

His Gln Asp Ile Asp
            20

```
<210> SEQ ID NO 63
<211> LENGTH: 15
<212> TYPE: PRT
<213> ORGANISM: Artificial sequence
<220> FEATURE:
<223> OTHER INFORMATION: Exemplary linker peptide

<400> SEQUENCE: 63
```

Gly Gly Gly Ser Leu Val Pro Arg Gly Ser Gly Gly Gly Gly Ser
1               5                   10                  15

```
<210> SEQ ID NO 64
<211> LENGTH: 40
<212> TYPE: PRT
<213> ORGANISM: Artificial sequence
<220> FEATURE:
<223> OTHER INFORMATION: Jun derived peptide

<400> SEQUENCE: 64
```

Arg Ile Ala Arg Leu Glu Glu Lys Val Lys Thr Leu Lys Ala Gln Asn
1               5                   10                  15

Ser Glu Leu Ala Ser Thr Ala Asn Met Leu Arg Glu Gln Val Ala Gln
            20                  25                  30

Leu Lys Gln Lys Val Met Asn His
        35                  40

```
<210> SEQ ID NO 65
```

```
<211> LENGTH: 7
<212> TYPE: PRT
<213> ORGANISM: Artificial sequence
<220> FEATURE:
<223> OTHER INFORMATION: Exemplary linker peptide

<400> SEQUENCE: 65

Val Asp Gly Gly Gly Gly Gly
1               5

<210> SEQ ID NO 66
<211> LENGTH: 40
<212> TYPE: PRT
<213> ORGANISM: Artificial sequence
<220> FEATURE:
<223> OTHER INFORMATION: Fos derived peptide

<400> SEQUENCE: 66

Leu Thr Asp Thr Leu Gln Ala Glu Thr Asp Gln Leu Glu Asp Glu Lys
1               5                   10                  15

Ser Ala Leu Gln Thr Glu Ile Ala Asn Leu Leu Lys Glu Lys Glu Lys
            20                  25                  30

Leu Glu Phe Ile Leu Ala Ala His
        35                  40

<210> SEQ ID NO 67
<211> LENGTH: 14
<212> TYPE: PRT
<213> ORGANISM: Artificial sequence
<220> FEATURE:
<223> OTHER INFORMATION: Bir A recognition sequence

<400> SEQUENCE: 67

Leu Gly Gly Ile Phe Glu Ala Met Lys Met Glu Leu Arg Asp
1               5                   10

<210> SEQ ID NO 68
<211> LENGTH: 238
<212> TYPE: PRT
<213> ORGANISM: Aequorea macrodactyla

<400> SEQUENCE: 68

Met Ser Lys Gly Glu Glu Leu Phe Thr Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Gly Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Met Pro Asp Lys Ala Asn Asn Gly
```

```
                    145                 150                 155                 160
Leu Lys Val Asn Phe Lys Ile Arg His Asn Ile Glu Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Leu Gln Thr Ala Ile Ser
            195                 200                 205

Lys Asp Arg Asn Glu Thr Arg Asp His Met Val Phe Leu Glu Phe Phe
        210                 215                 220

Ser Ala Cys Gly His Thr His Gly Met Asp Glu Leu Tyr Lys
225                 230                 235

<210> SEQ ID NO 69
<211> LENGTH: 717
<212> TYPE: DNA
<213> ORGANISM: Aequorea macrodactyla

<400> SEQUENCE: 69
atgagtaaag gagaagaact tttcactggg attgtcccag ttctcattga gttagacggt      60
gatgtccatg gacataaatt ctctgtcaga ggagaagggg aaggcgatgc agattatgga     120
aaacttgaaa tcaaattcat ttgcactact ggaaagctac cagttccatg gccaacactt     180
gttactacac tgggctacgg catccaatgt ttcgcaagat acccagaaca catgaaaatg     240
aatgacttct tcaagagtgc catgcctgag ggttacattc aagaagaac catcttttc      300 caagatgatg gaaaatacaa gacacgtggt gaagtcaagt ttgaaggtga tactcttgtt     360
aacagaattg agctcaaagg tatggacttt aagaagatg gcaatatcct tggacacaag     420
ttggagtaca atttttaattc acataatgta tacattatgc cggacaaagc caataatgga     480
ctcaaagtca atttcaaaat tagacacaat atcgaaggtg gtggtgtcca acttgctgat     540
cattaccaaa caaatgttcc ccttggagac ggtcctgtcc ttataccaat caatcactac     600
ctatccttgc aaacagccat ttcaaaagat cgaaatgaga cgagagatca tatggtgttt     660
ctggaatttt tctcagcttg tggacataca catggcatgg atgaactata caaataa       717

<210> SEQ ID NO 70
<211> LENGTH: 489
<212> TYPE: PRT
<213> ORGANISM: Artificial sequence
<220> FEATURE:
<223> OTHER INFORMATION: Alkaline phosphatase

<400> SEQUENCE: 70

Met Lys Gln Ser Thr Ile Ala Leu Ala Leu Leu Pro Leu Leu Phe Thr
1               5                   10                  15

Pro Val Thr Lys Ala Arg Thr Pro Glu Met Pro Leu Gln Gly Thr Ala
            20                  25                  30

Val Asp Gly Gly Gly Gly Ser Met His Ala Ser Leu Glu Val Leu Glu
        35                  40                  45

Asn Arg Ala Ala Gln Gly Asp Ile Thr Ala Pro Gly Gly Ala Arg Arg
    50                  55                  60

Leu Thr Gly Asp Gln Thr Ala Ala Leu Arg Asp Ser Leu Ser Asp Lys
65                  70                  75                  80

Pro Ala Lys Asn Ile Ile Leu Leu Ile Gly Asp Gly Met Gly Asp Ser
                85                  90                  95

Glu Ile Thr Ala Ala Arg Asn Tyr Ala Glu Gly Ala Gly Gly Phe Phe
            100                 105                 110
```

Lys Gly Ile Asp Ala Leu Pro Leu Thr Gly Gln Tyr Thr His Tyr Ala
            115                 120                 125

Leu Asn Lys Lys Thr Gly Lys Pro Asp Tyr Val Thr Asp Ser Ala Ala
        130                 135                 140

Ser Ala Thr Ala Trp Ser Thr Gly Val Lys Thr Tyr Asn Gly Ala Leu
145                 150                 155                 160

Gly Val Asp Ile His Glu Lys Asp His Pro Thr Ile Leu Glu Met Ala
                165                 170                 175

Lys Ala Ala Gly Leu Ala Thr Gly Asn Val Ser Thr Ala Glu Leu Gln
            180                 185                 190

Asp Ala Thr Pro Ala Ala Leu Val Ala His Val Thr Ser Arg Lys Cys
        195                 200                 205

Tyr Gly Pro Ser Ala Thr Ser Glu Lys Cys Pro Gly Asn Ala Leu Glu
    210                 215                 220

Lys Gly Gly Lys Gly Ser Ile Thr Glu Gln Leu Leu Asn Ala Arg Ala
225                 230                 235                 240

Asp Val Thr Leu Gly Gly Ala Lys Thr Phe Ala Glu Thr Ala Thr
                245                 250                 255

Ala Gly Glu Trp Gln Gly Lys Thr Leu Arg Glu Gln Ala Gln Ala Arg
            260                 265                 270

Gly Tyr Gln Leu Val Ser Asp Ala Ala Ser Leu Asn Ser Val Thr Glu
        275                 280                 285

Ala Asn Gln Gln Lys Pro Leu Leu Gly Leu Phe Ala Asp Gly Asn Met
290                 295                 300

Pro Val Arg Trp Leu Gly Pro Lys Ala Thr Tyr His Gly Asn Ile Asp
305                 310                 315                 320

Lys Pro Ala Val Thr Cys Thr Pro Asn Pro Gln Arg Asn Asp Ser Val
                325                 330                 335

Pro Thr Leu Ala Gln Met Thr Asp Lys Ala Ile Glu Leu Leu Ser Lys
            340                 345                 350

Asn Glu Lys Gly Phe Phe Leu Gln Val Glu Gly Ala Ser Ile Asp Lys
        355                 360                 365

Gln Asp His Ala Ala Asn Pro Cys Gly Gln Ile Gly Glu Thr Val Asp
    370                 375                 380

Leu Asp Glu Ala Val Gln Arg Ala Leu Glu Phe Ala Lys Lys Glu Gly
385                 390                 395                 400

Asn Thr Leu Val Ile Val Thr Ala Asp His Ala His Ala Ser Gln Ile
                405                 410                 415

Val Ala Pro Asp Thr Lys Ala Pro Gly Leu Thr Gln Ala Leu Asn Thr
            420                 425                 430

Lys Asp Gly Ala Val Met Val Met Ser Tyr Gly Asn Ser Glu Glu Asp
        435                 440                 445

Ser Gln Glu His Thr Gly Ser Gln Leu Arg Ile Ala Ala Tyr Gly Pro
    450                 455                 460

His Ala Ala Asn Val Val Gly Leu Thr Asp Gln Thr Asp Leu Phe Tyr
465                 470                 475                 480

Thr Met Lys Ala Ala Leu Gly Leu Lys
                485

<210> SEQ ID NO 71
<211> LENGTH: 1470
<212> TYPE: DNA
<213> ORGANISM: Artificial sequence
<220> FEATURE:

<223> OTHER INFORMATION: Alkaline phosphatase coding sequence

<400> SEQUENCE: 71

```
ttatttcagc cccagagcgg cttttcatggt gtagaagaga tcggtctggt cggtcagtcc    60
aacaacattg gcggcatgcg ggccatacgc cgcaatacgc aactgactgc ggtatgttc    120
ttgtgaatcc tcttcggagt tcccgtaact catcaccatc actgcgccat ctttggtatt   180
tagcgcctgg gtgaggcccg gagctttggt atccggcgca acaatctggc tggcgtgggc   240
gtgatcagcg gtgactatga ccagcgtgtt accctccttt ttagcgaatt ccagcgcccg   300
ttgtacggct tcatcgagat cgaccgtctc gccaatttgc ccacaaggat tcgcagcatg   360
atcctgttta tcgattgacg caccttcaac ttgcaggaaa aagcctttct cattttact    420
caacaattca atggctttgt cggtcatctg cgccagggtt ggtacactgt cattacgttg   480
cggatttggc gtacaggtga ctgcgggctt atcgatattg ccatggtacg ttgctttcgg   540
tcctagccag cgcactggca tattgccgtc agcaaacagg ccaagcaggg gttttttgctg  600
attcgcttcc gtcaccgaat tcagtgaggc agcatcgctc accaactgat aaccacgcgc   660
ctgtgcctgt tcacgcagcg ttttttccctg ccattcacca gcggttgccg tttcagcaaa  720
ggtttttgcg ccgccgccaa gcgtaacgtc ggcacgagcg ttaagcagct gttcggtaat   780
cgatcctttt ccgcctttt ccagagcgtt acccggacat ttttcactgg tcgcgctcgg   840
accgtagcat ttgcgcgagg tcacatgtgc caccagcgca gcgggcgtgg catcctgcaa   900
ctctgcggta gaaacgttac cggtcgccag acctgcggct tttgccattt ccagaatcgt   960
tgggtgatct ttttcgtgaa tatcgacgcc cagcgcgccg ttataggttt tgacaccggt  1020
tgaccaggcg gttgctgatg cagccgagtc ggtgacgtag tccggtttgc cggttttttt   1080
attcagcgca tagtgagtgt attgcccggt aagcggtaag gcatctatac ctttaaaaaa   1140
gccgcccgca ccttcggcat aattacgtgc ggcagtaatt tccgagtccc ccatcccatc  1200
gccaatcagc aaaataatat tttttgcagg tttatcgcta agagaatcac gcagagcggc   1260
agtctgatca cccgttaaac ggcgagcacc gccgggtgca gtaatatcgc cctgagcagc   1320
ccggttttcc agaacctcga ggctagcatg catagaaccg ccaccaccgt cgacagcggt   1380
accctgcaga ggcatttctg gtgtccgggc ttttgtcaca ggggtaaaca gtaacggtaa   1440
gagtgccagt gcaatagtgc tttgtttcac                                    1470
```

<210> SEQ ID NO 72
<211> LENGTH: 308
<212> TYPE: PRT
<213> ORGANISM: Artificial sequence
<220> FEATURE:
<223> OTHER INFORMATION: Horseradish peroxidase

<400> SEQUENCE: 72

```
Met Gln Leu Thr Pro Thr Phe Tyr Asp Asn Ser Cys Pro Asn Val Ser
1               5                   10                  15

Asn Ile Val Arg Asp Thr Ile Val Asn Glu Leu Arg Ser Asp Pro Arg
            20                  25                  30

Ile Ala Ala Ser Ile Leu Arg Leu His Phe His Asp Cys Phe Val Asn
        35                  40                  45

Gly Cys Asp Ala Ser Ile Leu Leu Asp Asn Thr Thr Ser Phe Arg Thr
    50                  55                  60

Glu Lys Asp Ala Phe Gly Asn Ala Asn Ser Ala Arg Gly Phe Pro Val
65                  70                  75                  80
```

Ile Asp Arg Met Lys Ala Ala Val Glu Ser Ala Cys Pro Arg Thr Val
            85                  90                  95

Ser Cys Ala Asp Leu Leu Thr Ile Ala Ala Gln Gln Ser Val Thr Leu
        100                 105                 110

Ala Gly Gly Pro Ser Trp Arg Val Pro Leu Gly Arg Arg Asp Ser Leu
        115                 120                 125

Gln Ala Phe Leu Asp Leu Ala Asn Ala Asn Leu Pro Ala Pro Phe Phe
    130                 135                 140

Thr Leu Pro Gln Leu Lys Asp Ser Phe Arg Asn Val Gly Leu Asn Arg
145                 150                 155                 160

Ser Ser Asp Leu Val Ala Leu Ser Gly Gly His Thr Phe Gly Lys Asn
                165                 170                 175

Gln Cys Arg Phe Ile Met Asp Arg Leu Tyr Asn Phe Ser Asn Thr Gly
            180                 185                 190

Leu Pro Asp Pro Thr Leu Asn Thr Thr Tyr Leu Gln Thr Leu Arg Gly
        195                 200                 205

Leu Cys Pro Leu Asn Gly Asn Leu Ser Ala Leu Val Asp Phe Asp Leu
    210                 215                 220

Arg Thr Pro Thr Ile Phe Asp Asn Lys Tyr Tyr Val Asn Leu Glu Glu
225                 230                 235                 240

Gln Lys Gly Leu Ile Gln Ser Asp Gln Glu Leu Phe Ser Ser Pro Asn
                245                 250                 255

Ala Thr Asp Thr Ile Pro Leu Val Arg Ser Phe Ala Asn Ser Thr Gln
            260                 265                 270

Thr Phe Phe Asn Ala Phe Val Glu Ala Met Asp Arg Met Gly Asn Ile
        275                 280                 285

Thr Pro Leu Thr Gly Thr Gln Gly Gln Ile Arg Leu Asn Cys Arg Val
    290                 295                 300

Val Asn Ser Asn
305

<210> SEQ ID NO 73
<211> LENGTH: 930
<212> TYPE: DNA
<213> ORGANISM: Artificial sequence
<220> FEATURE:
<223> OTHER INFORMATION: Horseradish peroxidase coding sequence

<400> SEQUENCE: 73
atgcagttaa cccctacatt ctacgacaat agctgtccca acgtgtccaa catcgttcgc      60
gacacaatcg tcaacgagct cagatccgat cccaggatcg ctgcttcaat attacgtctg    120
cacttccatg actgcttcgt gaatggttgc gacgctagca tattactgga caacaccacc    180
agtttccgca ctgaaaagga tgcattcggg aacgctaaca cgccaggggc ctttccagtg    240
atcgatcgca tgaaggctgc cgttgagtca gcatgcccac gaacagtcag ttgtgcagac    300
ctgctgacta gctgcgcaac agagcgtgta ctcttgcag gcggaccgtc ctggagagtg    360
ccgctcggtc gacgtgactc cctacaggca ttcctagatc tggccaacgc caacttgcct    420
gctccattct tcaccctgcc ccagctgaag gatagcttta aaacgtgggt ctgaatcgc     480 tcgagtgacc ttgtggctct gtccggagga cacacatttg aaagaaccag tgtaggttc    540 atcatggata ggctctacaa tttcagcaac actgggttac ctgaccccac gctgaacact    600
acgtatctcc agacactgag aggcttgtgc ccactgaatg caacctcag tgcactagtg    660 gactttgatc tgcggacccc aaccatcttc gataacaagt actatgtgaa tctagaggag    720

```
cagaaaggcc tgatacagag tgatcaagaa ctgtttagca gtccaaacgc cactgacacc    780
atcccactgg tgagaagttt tgctaactct actcaaacct tctttaacgc cttcgtggaa    840
gccatggacc gtatgggtaa cattacccct ctgacgggta cccaaggcca gattcgtctg    900
aactgcagag tggtcaacag caactcttaa                                     930
```

<210> SEQ ID NO 74
<211> LENGTH: 286
<212> TYPE: PRT
<213> ORGANISM: Artificial sequence
<220> FEATURE:
<223> OTHER INFORMATION: Synthetic construct fused to 6XHis and C-myc tags

<400> SEQUENCE: 74

```
Gln Ser Val Leu Thr Gln Pro Pro Ser Val Gly Ser Pro Gly Gln
1               5                   10                  15

Ser Ile Thr Ile Ser Cys Thr Gly Thr Ser Ser Asp Ile Gly Thr Tyr
            20                  25                  30

Lys Ile Val Ser Trp Tyr Gln Gln His Pro Gly Lys Ala Pro Lys Leu
        35                  40                  45

Met Ile Tyr Asp Val Asn Gln Arg Pro Ser Gly Val Ser Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Gly
                85                  90                  95

Ser Thr Leu Val Phe Gly Gly Gly Thr Lys Leu Thr Val Leu Gly Ser
            100                 105                 110

Ser Gly Gly Gly Gly Ser Gly Gly Gly Ser Gly Gly Ser Ala Leu
        115                 120                 125

Gln Val Gln Leu Gln Gln Ser Gly Ala Glu Val Lys Lys Pro Gly Glu
    130                 135                 140

Ser Leu Lys Ile Ser Cys Lys Gly Ser Gly Tyr Ser Phe Thr Ser Tyr
145                 150                 155                 160

Trp Ile Gly Trp Val Arg Gln Met Pro Gly Lys Gly Leu Glu Trp Met
                165                 170                 175

Gly Ile Ile Tyr Pro Gly Asp Ser Asp Thr Arg Tyr Ser Pro Ser Phe
            180                 185                 190

Gln Gly Gln Val Thr Ile Ser Ala Asp Lys Ser Ile Ser Thr Ala Tyr
        195                 200                 205

Leu Gln Trp Ser Ser Leu Lys Ala Ser Asp Thr Ala Met Tyr Tyr Cys
    210                 215                 220

Ala Arg His Arg Ala Ala Ser Gly Ser Pro Asp Ala Cys Asp Tyr Trp
225                 230                 235                 240

Gly Gln Gly Thr Leu Val Thr Val Ser Ser Gly Ser Ala Ser Ala Pro
                245                 250                 255

Thr Leu Phe Pro Ala Ala Ala His His His His His His Gly Ala Ala
            260                 265                 270

Glu Gln Lys Leu Ile Ser Glu Glu Asp Leu Asn Gly Ala Ala
        275                 280                 285
```

<210> SEQ ID NO 75
<211> LENGTH: 861
<212> TYPE: DNA
<213> ORGANISM: Artificial sequence
<220> FEATURE:

<223> OTHER INFORMATION: Synthetic construct fused to 6XHis and C-myc tags

<400> SEQUENCE: 75

```
cagtctgtgt tgacgcagcc gccctcagtg tctgggtctc ctggacagtc gatcaccatc    60
tcctgcactg gaaccagcag tgatattggg acttataaaa ttgtctcctg gtaccaacag   120
caccctggca agccccccaa actcatgatt tatgacgtca atcagcggcc ctcaggggtt   180
tctgatcgct tctctggctc caagtctggc aacacggcct ccctgacaat ctctgggctc   240
caggctgagg acgaggctga ttattactgc agctcatata caagcggcag cactctggta   300
ttcggcgggg gaccaagct gaccgtccta ggctcgagtg gtggaggcgg ttcaggcgga   360
ggtggctctg gcggtagtgc acttcaggta cagctgcagc agtcaggagc agaggtgaaa   420
aagcccgggg agtctctgaa gatctcctgt aagggttctg gatacagctt taccagctac   480
tggatcggct gggtgcgcca gatgcccggg aaaggcctgg agtggatggg gatcatctat   540
cctggtgact ctgataccag atacagcccg tccttccaag gccaggtcac catctcagcc   600
gacaagtcca tcagcaccgc ctacctgcag tggagcagcc tgaaggcctc ggacaccgcc   660
atgtattact gtgcgagaca tcgggccgct agtgggagcc cggacgcgtg tgactactgg   720
ggccagggaa ccctggtcac cgtctcctca gggagtgcat ccgccccaac cctttttccc   780
gcggccgcac atcatcatca ccatcacggg gccgcagaac aaaaactcat ctcagaagag   840
gatctgaatg gggccgcata g                                             861
```

<210> SEQ ID NO 76
<211> LENGTH: 345
<212> TYPE: PRT
<213> ORGANISM: Artificial sequence
<220> FEATURE:
<223> OTHER INFORMATION: PE38KDEL amino acid sequence

<400> SEQUENCE: 76

```
Glu Gly Gly Ser Leu Ala Ala Leu Thr Ala His Gln Ala Cys His Leu
1               5                   10                  15

Pro Leu Glu Thr Phe Thr Arg His Arg Gln Pro Arg Gly Trp Glu Gln
            20                  25                  30

Leu Glu Gln Cys Gly Tyr Pro Val Gln Arg Leu Val Ala Leu Tyr Leu
        35                  40                  45

Ala Ala Arg Leu Ser Trp Asn Gln Val Asp Gln Val Ile Arg Asn Ala
    50                  55                  60

Leu Ala Ser Pro Gly Ser Gly Gly Asp Leu Gly Glu Ala Ile Arg Glu
65                  70                  75                  80

Gln Pro Glu Gln Ala Arg Leu Ala Leu Thr Leu Ala Ala Ala Glu Ser
                85                  90                  95

Glu Arg Phe Val Arg Gln Gly Thr Gly Asn Asp Glu Ala Gly Ala Ala
            100                 105                 110

Asn Gly Pro Ala Asp Ser Gly Asp Ala Leu Leu Glu Arg Asn Tyr Pro
        115                 120                 125

Thr Gly Ala Glu Phe Leu Gly Asp Gly Gly Asp Val Ser Phe Ser Thr
    130                 135                 140

Arg Gly Thr Gln Asn Trp Thr Val Glu Arg Leu Leu Gln Ala His Arg
145                 150                 155                 160

Gln Leu Glu Glu Arg Gly Tyr Val Phe Val Gly Tyr His Gly Thr Phe
                165                 170                 175

Leu Glu Ala Ala Gln Ser Ile Val Phe Gly Gly Val Arg Ala Arg Ser
```

```
                180                 185                 190
Gln Asp Leu Asp Ala Ile Trp Arg Gly Phe Tyr Ile Ala Gly Asp Pro
            195                 200                 205

Ala Leu Ala Tyr Gly Tyr Ala Gln Asp Gln Glu Pro Asp Ala Arg Gly
        210                 215                 220

Arg Ile Arg Asn Gly Ala Leu Leu Arg Val Tyr Val Pro Arg Ser Ser
225                 230                 235                 240

Leu Pro Gly Phe Tyr Arg Thr Ser Leu Thr Leu Ala Ala Pro Glu Ala
                245                 250                 255

Ala Gly Glu Val Glu Arg Leu Ile Gly His Pro Leu Pro Leu Arg Leu
            260                 265                 270

Asp Ala Ile Thr Gly Pro Glu Glu Gly Gly Arg Leu Glu Thr Ile
        275                 280                 285

Leu Gly Trp Pro Leu Ala Glu Arg Thr Val Val Ile Pro Ser Ala Ile
        290                 295                 300

Pro Thr Asp Pro Arg Asn Val Gly Gly Asp Leu Asp Pro Ser Ser Ile
305                 310                 315                 320

Pro Asp Lys Glu Gln Ala Ile Ser Ala Leu Pro Asp Tyr Ala Ser Gln
                325                 330                 335

Pro Gly Lys Pro Pro Lys Asp Glu Leu
            340                 345

<210> SEQ ID NO 77
<211> LENGTH: 1035
<212> TYPE: DNA
<213> ORGANISM: Artificial sequence
<220> FEATURE:
<223> OTHER INFORMATION: PE38KDEL coding sequence

<400> SEQUENCE: 77
gagggcggca gcctggccgc gctgaccgcg caccaggctt gccacctgcc gctggagact      60
ttcacccgtc atcgccagcc gcgcggctgg gaacaactgg agcagtgcgg ctatccggtg     120
cagcggctgg tcgccctcta cctggcggcg cggctgtcgt ggaaccaggt cgaccaggtg     180
atccgcaacg ccctggccag ccccggcagc ggcggcgacc tgggcgaagc gatccgcgag     240
cagccggagc aggcccgtct ggccctgacc ctggccgccg ccgagagcga gcgcttcgtc     300
cggcagggca ccggcaacga cgaggccggc gcggccaacg ccccggcgga cagcggcgac     360
gccctgctgg agcgcaacta tcccactggc gcggagttcc tcggcgacgg cggcgacgtc     420
agcttcagca cccgcggcac gcagaactgg acggtggagc ggctgctcca ggcgcaccgc     480
caactggagg agcgcggcta tgtgttcgtc ggctaccacg gcaccttcct cgaagcggcg     540
caaagcatcg tcttcggcgg ggtgcgcgcg cgcagccagg acctgacgc gatctggcgc     600 ggtttctata tcgccggcga tccggcgctg gcctacggct acgcccagga ccaggaaccc     660
gacgcacgcg gccggatccg caacggtgcc ctgctgcggg tctatgtgcc gcgctcgagc     720
ctgccgggct tctaccgcac cagcctgacc ctggccgcgc cggaggcggc gggcgaggtc     780
gaacggctga tcggccatcc gctgccgctg cgcctggacg ccatcaccgg ccccgaggag     840
gaaggcgggc gcctggagac cattctcggc tggccgctgg ccgagcgcac cgtggtgatt     900
ccctcggcga tccccaccga cccgcgcaac gtcggcggcg acctcgaccc gtccagcatc     960
cccgacaagg aacaggcgat cagcgccctg ccggactacg ccagccagcc cggcaaaccg    1020
ccgaaagacg agctc                                                    1035
```

<210> SEQ ID NO 78
<211> LENGTH: 238
<212> TYPE: PRT
<213> ORGANISM: Artificial sequence
<220> FEATURE:
<223> OTHER INFORMATION: Orange fluorescent protein

<400> SEQUENCE: 78

```
Met Ser Lys Gly Glu Glu Leu Phe Thr Gly Val Val Pro Ile Leu Val
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Gly Tyr Gly Ile Leu Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Met Pro Asp Lys Ala Asn Asn Gly
145                 150                 155                 160

Leu Lys Val Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Tyr Gln Thr Ala Ile Ser
        195                 200                 205

Lys Asp Arg Asn Glu Thr Arg Asp His Met Val Phe Leu Glu Phe Phe
    210                 215                 220

Ser Ala Cys Gly His Thr His Gly Met Asp Glu Leu Tyr Lys
225                 230                 235
```

<210> SEQ ID NO 79
<211> LENGTH: 717
<212> TYPE: DNA
<213> ORGANISM: Artificial sequence
<220> FEATURE:
<223> OTHER INFORMATION: Orange fluorescent protein coding sequence

<400> SEQUENCE: 79

```
atgagtaaag gagaagaact tttcactgga gttgtcccaa ttcttgttga attagatggt    60
gatgtccatg gacataaatt ctctgtcaga ggagaagggg aaggcgatgc agattatgga   120
aaacttgaaa tcaaattcat ttgcactact ggaaagctac cagttccatg gccaacactt   180
gttactacac tgggctatgg catcctatgt ttcgcaagat acccagaaca catgaaaatg   240
aatgacttct tcaagagtgc catgcctgag ggttacattc aagaagaac catctttttc    300 caagatgatg gaaaatacaa gacacgtggt gaagtcaagt ttgaaggtga tactcttgtt   360
aacagaattg agctcaaagg tatggacttt aagaagatg gcaatatcct tggacacaag    420
ttggagtaca attttaactc acataatgta tacattatgc cggacaaagc caataatgga   480
```

```
ctcaaagtca atttcaaaat tagacacaat atcgaaggtg gtggtgtcca actcgctgat    540
cattaccaaa caaatgttcc ccttggagac ggtcctgtcc ttataccaat caatcactac    600
ctatcctatc aaacagccat ttcaaaagat cgaaatgaga cgagagatca tatggtgttt    660
ctggaatttt tctcagcttg tggacataca catggcatgg atgaactata caaataa      717
```

<210> SEQ ID NO 80
<211> LENGTH: 1019
<212> TYPE: PRT
<213> ORGANISM: Artificial sequence
<220> FEATURE:
<223> OTHER INFORMATION: Beta-galactosidase

<400> SEQUENCE: 80

```
Met Ala Asp Pro Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
            20                  25                  30

Arg Asn Ser Glu Glu Ala Arg Thr Asp Arg Pro Ser Gln Gln Leu Arg
        35                  40                  45

Ser Leu Asn Gly Glu Trp Arg Phe Ala Trp Phe Pro Ala Pro Glu Ala
    50                  55                  60

Val Pro Glu Ser Trp Leu Glu Cys Asp Leu Pro Glu Ala Asp Thr Val
65                  70                  75                  80

Val Val Pro Ser Asn Trp Gln Met His Gly Tyr Asp Ala Pro Ile Tyr
                85                  90                  95

Thr Asn Val Thr Tyr Pro Ile Thr Val Asn Pro Pro Phe Val Pro Thr
            100                 105                 110

Glu Asn Pro Thr Gly Cys Tyr Ser Leu Thr Phe Asn Val Asp Glu Ser
        115                 120                 125

Trp Leu Gln Glu Gly Gln Thr Arg Ile Ile Phe Asp Gly Val Asn Ser
    130                 135                 140

Ala Phe His Leu Trp Cys Asn Gly Arg Trp Val Gly Tyr Gly Gln Asp
145                 150                 155                 160

Ser Arg Leu Pro Ser Glu Phe Asp Leu Ser Ala Phe Leu Arg Ala Gly
                165                 170                 175

Glu Asn Arg Leu Ala Val Met Val Leu Arg Trp Ser Asp Gly Ser Tyr
            180                 185                 190

Leu Glu Asp Gln Asp Met Trp Arg Met Ser Gly Ile Phe Arg Asp Val
        195                 200                 205

Ser Leu Leu His Lys Pro Thr Thr Gln Ile Ser Asp Phe His Val Ala
    210                 215                 220

Thr Arg Phe Asn Asp Asp Phe Ser Arg Ala Val Leu Glu Ala Glu Val
225                 230                 235                 240

Gln Met Cys Gly Glu Leu Arg Asp Tyr Leu Arg Val Thr Val Ser Leu
                245                 250                 255

Trp Gln Gly Glu Thr Gln Val Ala Ser Gly Thr Ala Pro Phe Gly Gly
            260                 265                 270

Glu Ile Ile Asp Glu Arg Gly Gly Tyr Ala Asp Arg Val Thr Leu Arg
        275                 280                 285

Leu Asn Val Glu Asn Pro Lys Leu Trp Ser Ala Glu Ile Pro Asn Leu
    290                 295                 300

Tyr Arg Ala Val Val Glu Leu His Thr Ala Asp Gly Thr Leu Ile Glu
305                 310                 315                 320
```

```
Ala Glu Ala Cys Asp Val Gly Phe Arg Glu Val Arg Ile Glu Asn Gly
                325                 330                 335

Leu Leu Leu Leu Asn Gly Lys Pro Leu Leu Ile Arg Gly Val Asn Arg
            340                 345                 350

His Glu His His Pro Leu His Gly Gln Val Met Asp Glu Gln Thr Met
        355                 360                 365

Val Gln Asp Ile Leu Leu Met Lys Gln Asn Asn Phe Asn Ala Val Arg
    370                 375                 380

Cys Ser His Tyr Pro Asn His Pro Leu Trp Tyr Thr Leu Cys Asp Arg
385                 390                 395                 400

Tyr Gly Leu Tyr Val Val Asp Glu Ala Asn Ile Glu Thr His Gly Met
                405                 410                 415

Val Pro Met Asn Arg Leu Thr Asp Asp Pro Arg Trp Leu Pro Ala Met
            420                 425                 430

Ser Glu Arg Val Thr Arg Met Val Gln Arg Asp Arg Asn His Pro Ser
        435                 440                 445

Val Ile Ile Trp Ser Leu Gly Asn Glu Ser Gly His Gly Ala Asn His
    450                 455                 460

Asp Ala Leu Tyr Arg Trp Ile Lys Ser Val Asp Pro Ser Arg Pro Val
465                 470                 475                 480

Gln Tyr Glu Gly Gly Gly Ala Asp Thr Thr Ala Thr Asp Ile Ile Cys
                485                 490                 495

Pro Met Tyr Ala Arg Val Asp Glu Asp Gln Pro Phe Pro Ala Val Pro
            500                 505                 510

Lys Trp Ser Ile Lys Lys Trp Leu Ser Leu Pro Gly Glu Thr Arg Pro
        515                 520                 525

Leu Ile Leu Cys Glu Tyr Ala His Ala Met Gly Asn Ser Leu Gly Gly
    530                 535                 540

Phe Ala Lys Tyr Trp Gln Ala Phe Arg Gln Tyr Pro Arg Leu Gln Gly
545                 550                 555                 560

Gly Phe Val Trp Asp Trp Val Asp Gln Ser Leu Ile Lys Tyr Asp Glu
                565                 570                 575

Asn Gly Asn Pro Trp Ser Ala Tyr Gly Gly Asp Phe Gly Asp Thr Pro
            580                 585                 590

Asn Asp Arg Gln Phe Cys Met Asn Gly Leu Val Phe Ala Asp Arg Thr
        595                 600                 605

Pro His Pro Ala Leu Thr Glu Ala Lys His Gln Gln Gln Phe Phe Gln
    610                 615                 620

Phe Arg Leu Ser Gly Gln Thr Ile Glu Val Thr Ser Glu Tyr Leu Phe
625                 630                 635                 640

Arg His Ser Asp Asn Glu Leu Leu His Trp Met Val Ala Leu Asp Gly
                645                 650                 655

Lys Pro Leu Ala Ser Gly Glu Val Pro Leu Asp Val Ala Pro Gln Gly
            660                 665                 670

Lys Gln Leu Ile Glu Leu Pro Glu Leu Pro Gln Pro Glu Ser Ala Gly
        675                 680                 685

Gln Leu Trp Leu Thr Val Arg Val Val Gln Pro Asn Ala Thr Ala Trp
    690                 695                 700

Ser Glu Ala Gly His Ile Ser Ala Trp Gln Gln Trp Arg Leu Ala Glu
705                 710                 715                 720

Asn Leu Ser Val Thr Leu Pro Ala Ala Ser His Ala Ile Pro His Leu
                725                 730                 735

Thr Thr Ser Glu Met Asp Phe Cys Ile Glu Leu Gly Asn Lys Arg Trp
```

```
                    740                 745                 750
Gln Phe Asn Arg Gln Ser Gly Phe Leu Ser Gln Met Trp Ile Gly Asp
            755                 760                 765
Lys Lys Gln Leu Leu Thr Pro Leu Arg Asp Gln Phe Thr Arg Ala Pro
        770                 775                 780
Leu Asp Asn Asp Ile Gly Val Ser Glu Ala Thr Arg Ile Asp Pro Asn
785                 790                 795                 800
Ala Trp Val Glu Arg Trp Lys Ala Ala Gly His Tyr Gln Ala Glu Ala
                805                 810                 815
Ala Leu Leu Gln Cys Thr Ala Asp Thr Leu Ala Asp Ala Val Leu Ile
            820                 825                 830
Thr Thr Ala His Ala Trp Gln His Gln Gly Lys Thr Leu Phe Ile Ser
        835                 840                 845
Arg Lys Thr Tyr Arg Ile Asp Gly Ser Gly Gln Met Ala Ile Thr Val
    850                 855                 860
Asp Val Glu Val Ala Ser Asp Thr Pro His Pro Ala Arg Ile Gly Leu
865                 870                 875                 880
Asn Cys Gln Leu Ala Gln Val Ala Glu Arg Val Asn Trp Leu Gly Leu
                885                 890                 895
Gly Pro Gln Glu Asn Tyr Pro Asp Arg Leu Thr Ala Ala Cys Phe Asp
            900                 905                 910
Arg Trp Asp Leu Pro Leu Ser Asp Met Tyr Thr Pro Tyr Val Phe Pro
        915                 920                 925
Ser Glu Asn Gly Leu Arg Cys Gly Thr Arg Glu Leu Asn Tyr Gly Pro
    930                 935                 940
His Gln Trp Arg Gly Asp Phe Gln Phe Asn Ile Ser Arg Tyr Ser Gln
945                 950                 955                 960
Gln Gln Leu Met Glu Thr Ser His Arg His Leu Leu His Ala Glu Glu
                965                 970                 975
Gly Thr Trp Leu Asn Ile Asp Gly Phe His Met Gly Ile Gly Gly Asp
            980                 985                 990
Asp Ser Trp Ser Pro Ser Val Ser  Ala Asp Phe Gln Leu  Ser Ala Gly
        995                 1000                1005
Arg Tyr  His Tyr Gln Leu Val  Trp Cys Gln Lys
    1010                1015

<210> SEQ ID NO 81
<211> LENGTH: 3060
<212> TYPE: DNA
<213> ORGANISM: Artificial sequence
<220> FEATURE:
<223> OTHER INFORMATION: Beta-galactosidase coding sequence

<400> SEQUENCE: 81 ttattttga caccagacca actggtaatg gtagcgaccg gcgctcagct ggaaatccgc      60
cgatactgac gggctccagg agtcgtcgcc accaatcccc atatggaaac cgtcgatatt    120
cagccatgtg ccttcttccg cgtgcagcag atggcgatgg ctggtttcca tcagttgctg    180
ttgactgtag cggctgatgt tgaactggaa gtcgccgcgc cactggtgtg ggccataatt    240
caattcgcgc gtcccgcagc gcagaccgtt ttcgctcggg aagacgtacg gggtatacat    300
gtctgacaat ggcagatccc agcggtcaaa acaggcggca gtaaggcggt cgggatagtt    360
ttcttgcggc cctaatccga ccagtttac ccgtctctgct acctgcgcca gctggcagtt    420
caggccaatc gcgccggat gcggtgtatc gctcgccact tcaacatcaa cggtaatcgc      480
```

```
catttgacca ctaccatcaa tccggtaggt tttccggctg ataaataagg ttttcccctg    540
atgctgccac gcgtgagcgg tcgtaatcag caccgcatca gcaagtgtat ctgccgtgca    600
ctgcaacaac gctgcttcgg cctggtaatg gcccgccgcc ttccagcgtt cgacccaggc    660
gttagggtca atgcgggtcg cttcacttac gccaatgtcg ttatccagcg gtgcacgggt    720
gaactgatcg cgcagcggcg tcagcagttg tttttttatcg ccaatccaca tctgtgaaag    780
aaagcctgac tggcggttaa attgccaacg cttattaccc agctcgatgc aaaaatccat    840
ttcgctggtg gtcagatgcg ggatggcgtg ggacgcggcg gggagcgtca cactgaggtt    900
ttccgccaga cgccactgct gccaggcgct gatgtgcccg gcttctgacc atgcggtcgc    960
gttcggttgc actacgcgta ctgtgagcca gagttgcccg gcgctctccg gctgcggtag   1020
ttcaggcagt tcaatcaact gtttaccttg tggagcgaca tccagaggca cttcaccgct   1080
tgccagcggc ttaccatcca gcgccaccat ccagtgcagg agctcgttat cgctatgacg   1140
gaacaggtat tcgctggtca cttcgatggt ttgcccggat aaacggaact ggaaaaactg   1200
ctgctggtgt tttgcttccg tcagcgctgg atgcggcgtg cggtcggcaa agaccagacc   1260
gttcatacag aactggcgat cgttcggcgt atcgccaaaa tcaccgccgt aagccgacca   1320
cgggttgccg ttttcatcat atttaatcag cgactgatcc acccagtccc agacgaagcc   1380
gccctgtaaa cggggatact gacgaaacgc ctgccagtat ttagcgaaac cgccaagact   1440
gttacccatc gcgtgggcgt attcgcaaag gatcagcggg cgcgtctctc caggtagcga   1500
aagccatttt ttgatggacc atttcggcac agccgggaag ggctggtctt catccacgcg   1560
cgcgtacatc gggcaaataa tatcggtggc cgtggtgtcg gctccgccgc cttcatactg   1620
caccgggcgg gaaggatcga cagatttgat ccagcgatac agcgcgtcgt gattagcgcc   1680
gtggcctgat tcattcccca gcgaccagat gatcacactc gggtgattac gatcgcgctg   1740
caccattcgc gttacgcgtt cgctcatcgc cggtagccag cgcggatcat cggtcagacg   1800
attcattggc accatgccgt gggtttcaat attggcttca tccaccacat acaggccgta   1860
gcggtcgcac agcgtgtacc acagcggatg gttcggataa tgcgaacagc gcacggcgtt   1920
aaagttgttc tgcttcatca gcaggatatc ctgcaccatc gtctgctcat ccatgacctg   1980
accatgcaga ggatgatgct cgtgacggtt aacgcctcga atcagcaacg gcttgccgtt   2040
cagcagcagc agaccatttt caatccgcac ctcgcggaaa ccgacatcgc aggcttctgc   2100
ttcaatcagc gtgccgtcgg cggtgtgcag ttcaaccacc gcacgataga gattcgggat   2160
ttcggcgctc cacagtttcg ggttttcgac gttcagacgt agtgtgacgc gatcggcata   2220
accaccacgc tcatcgataa tttcaccgcc gaaaggcgcg gtgccgctgg cgacctgcgt   2280
ttcaccctgc cataaagaaa ctgttacccg taggtagtca cgcaactcgc cgcacatctg   2340
aacttcagcc tccagtacag cgcggctgaa atcatcatta aagcgagtgg caacatggaa   2400
atcgctgatt tgtgtagtcg gtttatgcag caacgagacg tcacggaaaa tgccgctcat   2460
ccgccacata tcctgatctt ccagataact gccgtcactc caacgcagca ccatcaccgc   2520
gaggcggttt tctccggcgc gtaaaaatgc gctcaggtca aattcagacg gcaaacgact   2580
gtcctggccg taaccgaccc agcgcccgtt gcaccacaga tgaaacgccg agttaacgcc   2640
atcaaaaata attcgcgtct ggccttcctg tagccagctt tcatcaacat aaatgtgag    2700 cgagtaacaa cccgtcggat tctccgtggg aacaaacggc ggattgaccg taatgggata   2760
ggttacgttg gtgtagatgg gcgcatcgta accgtgcatc tgccagtttg aggggacgac   2820
gacagtatcg gcctcaggaa gatcgcactc cagccagctt tccggcaccg cttctggtgc   2880
```

-continued

```
cggaaaccag gcaaagcgcc attcgccatt caggctgcgc aactgttggg aagggcgatc    2940
ggtgcgggcc tcttcgctat tacgccagct ggcgaaaggg ggatgtgctg caaggcgatt    3000
aagttgggta acgccagggt tttcccagtc acgacgttgt aaaacgacgg gatcagccat    3060
```

<210> SEQ ID NO 82
<211> LENGTH: 159
<212> TYPE: PRT
<213> ORGANISM: Artificial sequence
<220> FEATURE:
<223> OTHER INFORMATION: Streptavidin

<400> SEQUENCE: 82

```
Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155
```

<210> SEQ ID NO 83
<211> LENGTH: 480
<212> TYPE: DNA
<213> ORGANISM: Artificial sequence
<220> FEATURE:
<223> OTHER INFORMATION: Streptavidin coding sequence

<400> SEQUENCE: 83

```
gacccgagca agattctaa agcacaagta tctgctgcag aagcaggaat tacaggcaca     60
tggtataatc agctgggatc tacatttatt gttacagccg gcgcagatgg agctcttaca    120
ggaacatatg aatctgctgt tggaaatgca gaatctagat acgtgcttac aggaagatat    180
gattctgcac ctgcaacaga tggatccgga acagcacttg gatggacagt tgcatggaaa    240
aacaattata gaaacgcaca tagcgctaca acatggtctg gccaatatgt gggaggtgca    300
gaagcaagaa ttaacacaca atggctttta acatctggaa caacagaagc aaatgcatgg    360
aaaagtactc ttgttggaca tgatacattt acaaaagtta aacctagcgc agcatctatc    420
gatgcagcga aaaagcagg agttaacaat ggcaatcctt tagatgcagt tcaacaataa    480
```

<210> SEQ ID NO 84
<211> LENGTH: 216
<212> TYPE: PRT
<213> ORGANISM: Pseudomonas aeruginosa

<400> SEQUENCE: 84

```
Ala Glu Phe Leu Gly Asp Gly Asp Val Ser Phe Ser Thr Arg Gly
1               5                   10                  15

Thr Gln Asn Trp Thr Val Glu Arg Leu Leu Gln Ala His Arg Gln Leu
            20                  25                  30

Glu Glu Arg Gly Tyr Val Phe Val Gly Tyr His Gly Thr Phe Leu Glu
        35                  40                  45

Ala Ala Gln Ser Ile Val Phe Gly Gly Val Arg Ala Arg Ser Gln Asp
    50                  55                  60

Leu Asp Ala Ile Trp Arg Gly Phe Tyr Ile Ala Gly Asp Pro Ala Leu
65              70                  75                  80

Ala Tyr Gly Tyr Ala Gln Asp Gln Glu Pro Asp Ala Arg Gly Arg Ile
                85                  90                  95

Arg Asn Gly Ala Leu Leu Arg Val Tyr Val Pro Arg Ser Ser Leu Pro
            100                 105                 110

Gly Phe Tyr Arg Thr Gly Leu Thr Leu Ala Ala Pro Glu Ala Ala Gly
        115                 120                 125

Glu Val Glu Arg Leu Ile Gly His Pro Leu Pro Leu Arg Leu Asp Ala
    130                 135                 140

Ile Thr Gly Pro Glu Glu Gly Gly Arg Leu Glu Thr Ile Leu Gly
145                 150                 155                 160

Trp Pro Leu Ala Glu Arg Thr Val Val Ile Pro Ser Ala Ile Pro Thr
                165                 170                 175

Asp Pro Arg Asn Val Gly Gly Asp Leu Ala Pro Ser Ser Ile Pro Asp
            180                 185                 190

Gln Glu Gln Ala Ile Ser Ala Leu Pro Asp Tyr Ala Ser Gln Pro Gly
        195                 200                 205

Lys Pro Ser Arg Glu Asp Leu Lys
        210                 215
```

<210> SEQ ID NO 85
<211> LENGTH: 651
<212> TYPE: DNA
<213> ORGANISM: Pseudomonas aeruginosa

<400> SEQUENCE: 85

```
gcggagttcc tcggcgacgg cggcgacgtc agcttcagca cccgcggcac gcagaactgg     60
acggtggagc ggctgctcca ggcgcaccgc caactggagg agcgcggcta tgtgttcgtc    120
ggctaccacg gcaccttcct cgaagcggcg caaagcatcg tcttcggcgg ggtgcgcgcg    180
cgcagccagg accttgacgc gatctggcgc ggtttctata tcgccggcga tccggcgctg    240
gcctacggct acgcccagga ccaggaaccc gacgcgcgcg gccggatccg caacggtgcc    300
ctgctgcggg tctatgtgcc gcgctcgagt ctgccgggct ctaccgcac cggcctgacc    360
ctggccgcgc cggaggcggc gggcgaggtc gaacggctga tcggccatcc gctgccgctg    420
cgcctggacg ccatcaccgg ccccgaggag gaaggcgggc gctggagac cattctcggc    480
tggccgctgg ccgagcgcac cgtggtgatt ccctcggcga tccccaccga cccacgcaac    540
gtcggcggcg acctcgcccc gtccagcatc cccgaccagg aacaggcgat cagcgccctg    600
ccggactacg ccagccagcc cggcaaaccg tcgcgcgagg acctgaagta a              651
```

<210> SEQ ID NO 86
<211> LENGTH: 536
<212> TYPE: PRT
<213> ORGANISM: Corynebacterium diphtheriae

<400> SEQUENCE: 86

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Phe Leu His Asp Gly Tyr Ala Val Ser Trp Asn
385                 390                 395                 400

Thr Val Glu Asp Ser Ile Ile Arg Thr Gly Phe Gln Gly Glu Ser Gly
```

-continued

```
                405                 410                 415

His Asp Ile Lys Ile Thr Ala Glu Asn Thr Pro Leu Pro Ile Ala Gly
            420                 425                 430

Val Leu Leu Pro Thr Ile Pro Gly Lys Leu Asp Val Asn Lys Ser Lys
        435                 440                 445

Thr His Ile Ser Val Asn Gly Arg Lys Ile Arg Met Arg Cys Arg Ala
    450                 455                 460

Ile Asp Gly Asp Val Thr Phe Cys Arg Pro Lys Ser Pro Val Tyr Val
465                 470                 475                 480

Gly Asn Gly Val His Ala Asn Leu His Val Ala Phe His Arg Ser Ser
                485                 490                 495

Ser Glu Lys Ile His Ser Asn Glu Ile Ser Ser Asp Ser Ile Gly Val
            500                 505                 510

Leu Gly Tyr Gln Lys Thr Val Asp His Thr Lys Val Asn Ser Lys Leu
        515                 520                 525

Ser Leu Phe Phe Glu Ile Lys Ser
    530                 535

<210> SEQ ID NO 87
<211> LENGTH: 1611
<212> TYPE: DNA
<213> ORGANISM: Corynebacterium diphtheriae

<400> SEQUENCE: 87
atgggcgctg atgatgttgt tgattcttct aaatcttttg tgatggaaaa cttttcttcg     60
taccacggga ctaaacctgg ttatgtagat tccattcaaa aaggtataca aaagccaaaa    120
tctggtacac aaggaaatta tgacgatgat tggaaagggt tttatagtac cgacaataaa    180
tacgacgctg cgggatactc tgtagataat gaaaacccgc tctctggaaa agctggaggc    240
gtggtcaaag tgacgtatcc aggactgacg aaggttctcg cactaaaagt ggataatgcc    300
gaaactatta agaaagagtt aggtttaagt ctcactgaac cgttgatgga gcaagtcgga    360
acggaagagt ttatcaaaag gttcggtgat ggtgcttcgc gtgtagtgct cagccttccc    420
ttcgctgagg ggagttctag cgttgaatat attaataact gggaacaggc gaaagcgtta    480
agcgtagaac ttgagattaa ttttgaaacc cgtggaaaac gtggccaaga tgcgatgtat    540
gagtatatgg ctcaagcctg tgcaggaaat cgtgtcaggc gatcagtagg tagctcattg    600
tcatgcataa atcttgattg ggatgtcata agggataaaa ctaagacaaa gatagagtct    660
ttgaaagagc atggccctat caaaaataaa atgagcgaaa gtcccaataa aacagtatct    720
gaggaaaaag ctaaacaata cctagaagaa tttcatcaaa cggcattaga gcatcctgaa    780
ttgtcagaac ttaaaaccgt tactgggacc aatcctgtat tcgctggggc taactatgcg    840
gcgtgggcag taaacgttgc gcaagttatc gatagcgaaa cagctgataa tttggaaaag    900
acaactgctg ctctttcgat acttcctggt atcggtagcg taatgggcat tgcagacggt    960
gccgttcacc acaatacaga agagatagtg gcacaatcaa tagctttatc atctttaatg   1020
gttgctcaag ctattccatt ggtaggagag ctagttgata ttggtttcgc tgcatataat   1080
tttgtagaga gtattatcaa tttatttcaa gtagttcata attcgtataa tcgtcccgcg   1140
tattctccgg ggcataaaac gcaaccattt cttcatgacg ggtatgctgt cagttggaac   1200
actgttgaag attcgataat ccgaactggt tttcaagggg agagtgggca cgacataaaa   1260
attactgctg aaaatacccc gcttccaatc gcgggtgtcc tactaccgac tattcctgga   1320
aagctggacg ttaataagtc caagactcat atttccgtaa atggtcggaa aataaggatg   1380
```
cgttgcagag ctatagacgg tgatgtaact ttttgtcgcc ctaaatctcc tgttttatgtt    1440 ggtaatggtg tgcatgcgaa tcttcacgtg gcatttcaca gaagcagctc ggagaaaatt    1500
cattctaatg aaatttcatc ggattccata ggcgttcttg ggtaccagaa aacagtagat    1560
cacaccaagg ttaattctaa gctatcgcta ttttttgaaa tcaaaagctg a             1611

<210> SEQ ID NO 88
<211> LENGTH: 127
<212> TYPE: PRT
<213> ORGANISM: Artificial sequence
<220> FEATURE:
<223> OTHER INFORMATION: Interleukin 2 (IL-2)

<400> SEQUENCE: 88

Thr Lys Lys Thr Gln Leu Gln Leu Glu His Leu Leu Leu Asp Leu Gln
1               5                   10                  15

Met Ile Leu Asn Gly Ile Asn Asn Tyr Lys Asn Pro Lys Leu Thr Arg
            20                  25                  30

Met Leu Thr Phe Lys Phe Tyr Met Pro Lys Lys Ala Thr Glu Leu Lys
        35                  40                  45

His Leu Gln Cys Leu Glu Glu Glu Leu Lys Pro Leu Glu Glu Val Leu
    50                  55                  60

Asn Leu Ala Gln Ser Lys Asn Phe His Leu Arg Pro Arg Asp Leu Ile
65                  70                  75                  80

Ser Asn Ile Asn Val Ile Val Leu Glu Leu Lys Gly Ser Glu Thr Thr
                85                  90                  95

Phe Met Cys Glu Tyr Ala Asp Glu Thr Ala Thr Ile Val Glu Phe Leu
            100                 105                 110

Asn Arg Trp Ile Thr Phe Cys Gln Ser Ile Ile Ser Thr Leu Thr
        115                 120                 125

<210> SEQ ID NO 89
<211> LENGTH: 384
<212> TYPE: DNA
<213> ORGANISM: Artificial sequence
<220> FEATURE:
<223> OTHER INFORMATION: Interleukin 2 (IL-2)

<400> SEQUENCE: 89
acaaagaaaa cacagctaca actggagcat ttacttctgg atttacagat gattttgaat     60
ggaattaata attacaagaa tcccaaactc accaggatgc tcacatttaa gttttacatg    120
cccaagaagg ccacagaact gaaacatctt cagtgtctag aagaagaact caaacctctg    180
gaggaagtgc taaatttagc tcaaagcaaa aactttcact aagacccagg gacttaatc     240 agcaatatca acgtaatagt tctggaacta aagggatctg aaacaacatt catgtgtgaa    300
tatgctgatg agacagcaac cattgtagaa tttctgaaca gatggattac cttttgtcaa    360
agcatcatct caacactgac ttga                                           384

<210> SEQ ID NO 90
<211> LENGTH: 207
<212> TYPE: PRT
<213> ORGANISM: Artificial sequence
<220> FEATURE:
<223> OTHER INFORMATION: Human derived CD3 polypeptide

<400> SEQUENCE: 90

Met Gln Ser Gly Thr His Trp Arg Val Leu Gly Leu Cys Leu Leu Ser
1               5                   10                  15

```
Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
                195                 200                 205

<210> SEQ ID NO 91
<211> LENGTH: 624
<212> TYPE: DNA
<213> ORGANISM: Artificial sequence
<220> FEATURE:
<223> OTHER INFORMATION: Human derived CD3 polynucleotide

<400> SEQUENCE: 91
atgcagtcgg gcactcactg gagagttctg ggcctctgcc tcttatcagt tggcgtttgg      60
gggcaagatg gtaatgaaga atgggtggt attacacaga caccatataa agtctccatc     120
tctggaacca cagtaatatt gacatgccct cagtatcctg gatctgaaat actatggcaa     180
cacaatgata aaaacatagg cggtgatgag gatgataaaa acataggcag tgatgaggat     240
cacctgtcac tgaaggaatt ttcagaattg gagcaaagtg gttattatgt ctgctacccc     300
agaggaagca aaccagaaga tgcgaacttt tatctctacc tgagggcaag agtgtgtgag     360
aactgcatgg agatggatgt gatgtcggtg gccacaattg tcatagtgga catctgcatc     420
actgggggct gctgctgct ggtttactac tggagcaaga tagaaaggc caaggccaag     480 cctgtgacac gaggagcggg tgctggcggc aggcaaaggg gacaaaacaa ggagaggcca     540
ccacctgttc ccaacccaga ctatgagccc atccggaaag gccagcggga cctgtattct     600
ggcctgaatc agagacgcat ctga                                            624

<210> SEQ ID NO 92
<211> LENGTH: 290
<212> TYPE: PRT
<213> ORGANISM: Artificial sequence
<220> FEATURE:
<223> OTHER INFORMATION: CD16

<400> SEQUENCE: 92
```

Met Gly Gly Gly Ala Gly Glu Arg Leu Phe Thr Ser Ser Cys Leu Val
1               5                   10                  15
Gly Leu Val Pro Leu Gly Leu Arg Ile Ser Leu Val Thr Cys Pro Leu
            20                  25                  30
Gln Cys Gly Ile Met Trp Gln Leu Leu Leu Pro Thr Ala Leu Leu Leu
        35                  40                  45
Leu Val Ser Ala Gly Met Arg Thr Glu Asp Leu Pro Lys Ala Val Val
    50                  55                  60
Phe Leu Glu Pro Gln Trp Tyr Arg Val Leu Glu Lys Asp Ser Val Thr
65                  70                  75                  80
Leu Lys Cys Gln Gly Ala Tyr Ser Pro Glu Asp Asn Ser Thr Gln Trp
                85                  90                  95
Phe His Asn Glu Ser Leu Ile Ser Ser Gln Ala Ser Ser Tyr Phe Ile
            100                 105                 110
Asp Ala Ala Thr Val Asp Asp Ser Gly Glu Tyr Arg Cys Gln Thr Asn
            115                 120                 125
Leu Ser Thr Leu Ser Asp Pro Val Gln Leu Glu Val His Ile Gly Trp
    130                 135                 140
Leu Leu Leu Gln Ala Pro Arg Trp Val Phe Lys Glu Glu Asp Pro Ile
145                 150                 155                 160
His Leu Arg Cys His Ser Trp Lys Asn Thr Ala Leu His Lys Val Thr
                165                 170                 175
Tyr Leu Gln Asn Gly Lys Gly Arg Lys Tyr Phe His His Asn Ser Asp
            180                 185                 190
Phe Tyr Ile Pro Lys Ala Thr Leu Lys Asp Ser Gly Ser Tyr Phe Cys
            195                 200                 205
Arg Gly Leu Phe Gly Ser Lys Asn Val Ser Ser Glu Thr Val Asn Ile
        210                 215                 220
Thr Ile Thr Gln Gly Leu Ala Val Ser Thr Ile Ser Ser Phe Phe Pro
225                 230                 235                 240
Pro Gly Tyr Gln Val Ser Phe Cys Leu Val Met Val Leu Leu Phe Ala
            245                 250                 255
Val Asp Thr Gly Leu Tyr Phe Ser Val Lys Thr Asn Ile Arg Ser Ser
            260                 265                 270
Thr Arg Asp Trp Lys Asp His Lys Phe Lys Trp Arg Lys Asp Pro Gln
        275                 280                 285
Asp Lys
    290

<210> SEQ ID NO 93
<211> LENGTH: 873
<212> TYPE: DNA
<213> ORGANISM: Artificial sequence
<220> FEATURE:
<223> OTHER INFORMATION: CD16 coding region

<400> SEQUENCE: 93
atgggtggag gggctgggga aaggctgttt acttcctcct gtctagtcgg tttggtccct        60
ttagggctcc ggatatcttt ggtgacttgt ccactccagt gtggcatcat gtggcagctg       120
ctcctcccaa ctgctctgct acttctagtt tcagctggca tgcggactga agatctccca       180
aaggctgtgg tgttcctgga gcctcaatgg tacagggtgc tcgagaagga cagtgtgact       240
ctgaagtgcc agggagccta ctcccctgag gacaattcca cacagtggtt tcacaatgag       300
agcctcatct caagccaggc ctcgagctac ttcattgacg ctgccacagt cgacgacagt       360

-continued

```
ggagagtaca ggtgccagac aaacctctcc accctcagtg acccggtgca gctagaagtc    420
catatcggct ggctgttgct ccaggcccct cggtgggtgt tcaaggagga agaccctatt    480
cacctgaggt gtcacagctg aagaacact gctctgcata aggtcacata tttacagaat    540
ggcaaaggca ggaagtattt tcatcataat tctgacttct acattccaaa agccacactc    600
aaagacagcg gctcctactt ctgcaggggg cttttggga gtaaaatgt gtcttcagag     660 actgtgaaca tcaccatcac tcaaggtttg gcagtgtcaa ccatctcatc attctttcca    720
cctgggtacc aagtctcttt ctgcttggtg atggtactcc ttttgcagt ggacacagga    780 ctatatttct ctgtgaagac aaacattcga agctcaacaa gagactggaa ggaccataaa    840
tttaaatgga gaaggaccc tcaagacaaa tga                                  873
```

<210> SEQ ID NO 94
<211> LENGTH: 153
<212> TYPE: PRT
<213> ORGANISM: Artificial sequence
<220> FEATURE:
<223> OTHER INFORMATION: Interleukin 4

<400> SEQUENCE: 94

```
Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150
```

<210> SEQ ID NO 95
<211> LENGTH: 462
<212> TYPE: DNA
<213> ORGANISM: Artificial sequence
<220> FEATURE:
<223> OTHER INFORMATION: Interleukin 4 coding sequence

<400> SEQUENCE: 95

```
atgggtctca cctcccaact gcttcccct ctgttcttcc tgctagcatg tgccggcaac    60
tttgtccacg gacacaagtg cgatatcacc ttacaggaga tcatcaaaac tttgaacagc    120
ctcacagagc agaagactct gtgcaccgag ttgaccgtaa cagacatctt tgctgcctcc    180
aagaacacaa ctgagaagga aaccttctgc agggctgcga ctgtgctccg gcagttctac    240
agccaccatg agaaggacac tcgctgcctg ggtgcgactg cacagcagtt ccacaggcac    300
aagcagctga tccgattcct gaaacggctc gacaggaacc tctggggcct ggcgggcttg    360
```

```
aattcctgtc ctgtgaagga agccaaccag agtacgttgg aaaacttctt ggaaaggcta    420
aagacgatca tgagagagaa atattcaaag tgttcgagct ga                       462
```

<210> SEQ ID NO 96
<211> LENGTH: 365
<212> TYPE: PRT
<213> ORGANISM: Artificial sequence
<220> FEATURE:
<223> OTHER INFORMATION: Human derived HLA-A2

<400> SEQUENCE: 96

```
Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
```

```
                340                 345                 350
Ala Gln Gly Ser Asp Val Ser Leu Thr Ala Cys Lys Val
        355                 360                 365
```

<210> SEQ ID NO 97
<211> LENGTH: 1098
<212> TYPE: DNA
<213> ORGANISM: Artificial sequence
<220> FEATURE:
<223> OTHER INFORMATION: Human derived HLA-A2 coding sequence

<400> SEQUENCE: 97

```
atggccgtca tggcgccccg aaccctcgtc ctgctactct cgggggctct ggccctgacc      60
cagacctggg cgggctctca ctccatgagg tatttcttca catccgtgtc ccggcccggc     120
cgcggggagc cccgcttcat cgcagtgggc tacgtggacg acacgcagtt cgtgcgcttc     180
gacagcgacg ccgcgagcca gaggatggag ccgcgggcgc cgtggataga gcaggagggt     240
ccggagtatt gggacgggga gacacggaaa gtgaaggccc actcacagac tcaccgagtg     300
gacctgggga ccctgcgcgg ctactacaac cagagcgagg ccggttctca caccgtccag     360
aggatgtatg gctgcgacgt ggggtcggac tggcgcttcc tccgcgggta ccaccagtac     420
gcctacgacg gcaaggatta catcgccctg aaagaggacc tgcgctcttg gaccgcggcg     480
gacatggcag ctcagaccac caagcacaag tgggaggcgg cccatgtggc ggagcagttg     540
agagcctacc tggagggcac gtgcgtggag tggctccgca gatacctgga gaacgggaag     600
gagacgctgc agcgcacgga cgcccccaaa acgcatatga ctcaccacgc tgtctctgac     660
catgaagcca ccctgaggtg ctgggccctg agcttctacc ctgcggagat cacactgacc     720
tggcagcggg atggggagga ccagacccag gacacggagc tcgtggagac caggcctgca     780
ggggatggaa ccttccagaa gtgggcggct gtggtggtgc cttctggaca ggagcagaga     840
tacacctgcc atgtgcagca tgagggtttg cccaagcccc tcaccctgag atgggagccg     900
tcttcccagc ccaccatccc catcgtgggc atcattgctg gcctggttct ctttggagct     960
gtgatcactg gagctgtggt cgctgctgtg atgtggagga ggaagagctc agatagaaaa    1020
ggagggagct actctcaggc tgcaagcagt gacagtgccc agggctctga tgtgtctctc    1080
acagcttgta aagtgtga                                                 1098
```

<210> SEQ ID NO 98
<211> LENGTH: 178
<212> TYPE: PRT
<213> ORGANISM: Artificial sequence
<220> FEATURE:
<223> OTHER INFORMATION: Human derived interleukine 10

<400> SEQUENCE: 98

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
```

```
                    85                  90                  95
Gln Ala Glu Asn Gln Asp Pro Asp Ile Lys Ala His Val Asn Ser Leu
                100                 105                 110
Gly Glu Asn Leu Lys Thr Leu Arg Leu Arg Leu Arg Arg Cys His Arg
            115                 120                 125
Phe Leu Pro Cys Glu Asn Lys Ser Lys Ala Val Glu Gln Val Lys Asn
        130                 135                 140
Ala Phe Asn Lys Leu Gln Glu Lys Gly Ile Tyr Lys Ala Met Ser Glu
145                 150                 155                 160
Phe Asp Ile Phe Ile Asn Tyr Ile Glu Ala Tyr Met Thr Met Lys Ile
                165                 170                 175
Arg Asn

<210> SEQ ID NO 99
<211> LENGTH: 537
<212> TYPE: DNA
<213> ORGANISM: Artificial sequence
<220> FEATURE:
<223> OTHER INFORMATION: Human derived interleukine 10 coding sequence

<400> SEQUENCE: 99
atgcacagct cagcactgct ctgttgcctg gtcctcctga ctggggtgag ggccagccca      60
ggccagggca cccagtctga aacagctgc acccacttcc aggcaacct gcctaacatg      120 cttcgagatc tccgagatgc cttcagcaga gtgaagactt tctttcaaat gaaggatcag      180
ctggacaact gcttgttaaa ggagtccttg ctggaggact taagggtta cctgggttgc      240 caagccttgt ctgagatgat ccagttttac ctggaggagg tgatgcccca agctgagaac      300
caagacccag acatcaaggc gcatgtgaac tccctggggg agaacctgaa gaccctcagg      360
ctgaggctac ggcgctgtca tcgatttctt ccctgtgaaa acaagagcaa ggccgtggag      420
caggtgaaga tgcctttaa taagctccaa gagaaaggca tctacaaagc catgagtgag      480
tttgacatct tcatcaacta catagaagcc tacatgacaa tgaagatacg aaactga       537

<210> SEQ ID NO 100
<211> LENGTH: 576
<212> TYPE: PRT
<213> ORGANISM: Artificial sequence
<220> FEATURE:
<223> OTHER INFORMATION: Ricin toxin

<400> SEQUENCE: 100

Met Lys Pro Gly Gly Asn Thr Ile Val Ile Trp Met Tyr Ala Val Ala
1               5                   10                  15
Thr Trp Leu Cys Phe Gly Ser Thr Ser Gly Trp Ser Phe Thr Leu Glu
            20                  25                  30
Asp Asn Asn Ile Phe Pro Lys Gln Tyr Pro Ile Ile Asn Phe Thr Thr
        35                  40                  45
Ala Gly Ala Thr Val Gln Ser Tyr Thr Asn Phe Ile Arg Ala Val Arg
    50                  55                  60
Gly Arg Leu Thr Thr Gly Ala Asp Val Arg His Glu Ile Pro Val Leu
65                  70                  75                  80
Pro Asn Arg Val Gly Leu Pro Ile Asn Gln Arg Phe Ile Leu Val Glu
                85                  90                  95
Leu Ser Asn His Ala Glu Leu Ser Val Thr Leu Ala Leu Asp Val Thr
                100                 105                 110
Asn Ala Tyr Val Val Gly Tyr Arg Ala Gly Asn Ser Ala Tyr Phe Phe
```

```
            115                 120                 125
His Pro Asp Asn Gln Glu Asp Ala Glu Ala Ile Thr His Leu Phe Thr
130                 135                 140

Asp Val Gln Asn Arg Tyr Thr Phe Ala Phe Gly Gly Asn Tyr Asp Arg
145                 150                 155                 160

Leu Glu Gln Leu Ala Gly Asn Leu Arg Glu Asn Ile Glu Leu Gly Asn
                165                 170                 175

Gly Pro Leu Glu Glu Ala Ile Ser Ala Leu Tyr Tyr Ser Thr Gly
                180                 185                 190

Gly Thr Gln Leu Pro Thr Leu Ala Arg Ser Phe Ile Ile Cys Ile Gln
                195                 200                 205

Met Ile Ser Glu Ala Ala Arg Phe Gln Tyr Ile Glu Gly Glu Met Arg
210                 215                 220

Thr Arg Ile Arg Tyr Asn Arg Arg Ser Ala Pro Asp Pro Ser Val Ile
225                 230                 235                 240

Thr Leu Glu Asn Ser Trp Gly Arg Leu Ser Thr Ala Ile Gln Glu Ser
                245                 250                 255

Asn Gln Gly Ala Phe Ala Ser Pro Ile Gln Leu Gln Arg Arg Asn Gly
                260                 265                 270

Ser Lys Phe Ser Val Tyr Asp Val Ser Ile Leu Ile Pro Ile Ile Ala
                275                 280                 285

Leu Met Val Tyr Arg Cys Ala Pro Pro Ser Ser Gln Phe Ser Leu
290                 295                 300

Leu Ile Arg Pro Val Val Pro Asn Phe Asn Ala Asp Val Cys Met Asp
305                 310                 315                 320

Pro Glu Pro Ile Val Arg Ile Val Gly Arg Asn Gly Leu Cys Val Asp
                325                 330                 335

Val Arg Asp Gly Arg Phe His Asn Gly Asn Ala Ile Gln Leu Trp Pro
                340                 345                 350

Cys Lys Ser Asn Thr Asp Ala Asn Gln Leu Trp Thr Leu Lys Arg Asp
                355                 360                 365

Asn Thr Ile Arg Ser Asn Gly Lys Cys Leu Thr Thr Tyr Gly Tyr Ser
                370                 375                 380

Pro Gly Val Tyr Val Met Ile Tyr Asp Cys Asn Thr Ala Ala Thr Asp
385                 390                 395                 400

Ala Thr Arg Trp Gln Ile Trp Asp Asn Gly Thr Ile Ile Asn Pro Arg
                405                 410                 415

Ser Ser Leu Val Leu Ala Ala Thr Ser Gly Asn Ser Gly Thr Thr Leu
                420                 425                 430

Thr Val Gln Thr Asn Ile Tyr Ala Val Ser Gln Gly Trp Leu Pro Thr
                435                 440                 445

Asn Asn Thr Gln Pro Phe Val Thr Thr Ile Val Gly Leu Tyr Gly Leu
                450                 455                 460

Cys Leu Gln Ala Asn Ser Gly Gln Val Trp Ile Glu Asp Cys Ser Ser
465                 470                 475                 480

Glu Lys Ala Glu Gln Gln Trp Ala Leu Tyr Ala Asp Gly Ser Ile Arg
                485                 490                 495

Pro Gln Gln Asn Arg Asp Asn Cys Leu Thr Ser Asp Ser Asn Ile Arg
                500                 505                 510

Glu Thr Val Val Lys Ile Leu Ser Cys Gly Pro Ala Ser Ser Gly Gln
                515                 520                 525

Arg Trp Met Phe Lys Asn Asp Gly Thr Ile Leu Asn Leu Tyr Ser Gly
                530                 535                 540
```

Leu Val Leu Asp Val Arg Ala Ser Asp Pro Ser Leu Lys Gln Ile Ile
545                 550                 555                 560

Leu Tyr Pro Leu His Gly Asp Pro Asn Gln Ile Trp Leu Pro Leu Phe
                565                 570                 575

<210> SEQ ID NO 101
<211> LENGTH: 1731
<212> TYPE: DNA
<213> ORGANISM: Artificial sequence
<220> FEATURE:
<223> OTHER INFORMATION: Ricin toxin coding sequence

<400> SEQUENCE: 101

| | | | | | | |
|---|---|---|---|---|---|---|
| atgaaaccgg | aggaaatac | tattgtaata | tggatgtatg | cagtggcaac | atggctttgt | 60 |
| tttggatcca | cctcagggtg | gtctttcaca | ttagaggata | caacatatt | ccccaaacaa | 120 |
| tacccaatta | taaactttac | cacagcgggt | gccactgtgc | aaagctacac | aaactttatc | 180 |
| agagctgttc | gcggtcgttt | aacaactgga | gctgatgtga | acatgaaat | accagtgttg | 240 |
| ccaaacagag | ttggtttgcc | tataaaccaa | cggtttattt | tagttgaact | ctcaaatcat | 300 |
| gcagagcttt | ctgttacatt | agcgctggat | gtcaccaatg | catatgtggt | cggctaccgt | 360 |
| gctggaaata | gcgcatattt | ctttcatcct | gacaatcagg | aagatgcaga | agcaatcact | 420 |
| catcttttca | ctgatgttca | aaatcgatat | acattcgcct | tggtggtaa | ttatgataga | 480 |
| cttgaacaac | ttgctggtaa | tctgagagaa | aatatcgagt | gggaaatgg | tccactagag | 540 |
| gaggctatct | cagcgcttta | ttattacagt | actggtggca | ctcagcttcc | aactctggct | 600 |
| cgttccttta | taatttgcat | ccaaatgatt | tcagaagcag | caagattcca | atatattgag | 660 |
| ggagaaatgc | gcacgagaat | taggtacaac | cggagatctg | caccagatcc | tagcgtaatt | 720 |
| acacttgaga | atagttgggg | gagactttcc | actgcaattc | aagagtctaa | ccaaggagcc | 780 |
| tttgctagtc | caattcaact | gcaaagacgt | aatggttcca | aattcagtgt | gtacgatgtg | 840 |
| agtatattaa | tccctatcat | agctctcatg | gtgtatagat | gcgcacctcc | accatcgtca | 900 |
| cagttttctt | tgcttataag | gccagtggta | ccaaatttta | atgctgatgt | ttgtatggat | 960 |
| cctgagccca | tagtgcgtat | cgtaggtcga | atggtctat | gtgttgatgt | tagggatgga | 1020 |
| agattccaca | acggaaacgc | aatacagttg | tggccatgca | agtctaatac | agatgcaaat | 1080 |
| cagctctgga | ctttgaaaag | agacaatact | attcgatcta | atggaaagtg | tttaactact | 1140 |
| tacgggtaca | gtccgggagt | ctatgtgatg | atctatgatt | gcaatactgc | tgcaactgat | 1200 |
| gccacccgct | ggcaaatatg | ggataatgga | accatcataa | atcccagatc | tagtctagtt | 1260 |
| ttagcagcga | catcagggaa | cagtggtacc | acacttacag | tgcaaaccaa | catttatgcc | 1320 |
| gttagtcaag | gttggcttcc | tactaataat | acacaacctt | ttgtgacaac | cattgttggg | 1380 |
| ctatatggtc | tgtgcttgca | agcaaatagt | ggacaagtat | ggatagagga | ctgtagcagt | 1440 |
| gaaaaggctg | aacaacagtg | ggctctttat | gcagatggt | caatacgtcc | tcagcaaaac | 1500 |
| cgagataatt | gccttacaag | tgattctaat | atacgggaaa | cagttgtcaa | gatcctctct | 1560 |
| tgtggccctg | catcctctgg | ccaacgatgg | atgttcaaga | tgatggaac | catttttaaat | 1620 |
| ttgtatagtg | ggttggtgtt | agatgtgagg | gcatcggatc | cgagccttaa | acaaatcatt | 1680 |
| ctttacccctc | tccatggtga | cccaaaccaa | atatggttac | cattattttg | a | 1731 |

<210> SEQ ID NO 102
<211> LENGTH: 15
<212> TYPE: PRT

```
<213> ORGANISM: Artificial sequence
<220> FEATURE:
<223> OTHER INFORMATION: Biotin lygase tag

<400> SEQUENCE: 102

Leu His His Ile Leu Asp Ala Gln Lys Met Val Trp Asn His Arg
1               5                   10                  15
```

ISOLATED HIGH AFFINITY ENTITIES WITH T-CELL RECEPTOR LIKE SPECIFICITY TOWARDS NATIVE COMPLEXES OF MHC CLASS II AND GLUTAMIC ACID DECARBOXYLASE (GAD) AUTOANTIGENIC PEPTIDES

RELATED APPLICATIONS

This application is a National Phase of PCT Patent Application No. PCT/IL2011/000564 having International filing date of Jul. 14, 2011, which claims the benefit of priority under 35 USC §119(e) of U.S. Provisional Patent Application No. 61/364,443 filed on Jul. 15, 2010. The contents of the above applications are all incorporated by reference as if fully set forth herein in their entirety.

FIELD AND BACKGROUND OF THE INVENTION

The present invention, in some embodiments thereof, relates to isolated complexes of MHC class II and glutamic acid decarboxylase (GAD) autoantigenic peptides, isolated high affinity entities such as antibodies which specifically bind to same and, more particularly, but not exclusively, to uses thereof for diagnosing and treating type I diabetes.

Major histocompatibility complex (MHC) class II molecules are expressed in professional antigen presenting cells (APCs) such as macrophages, dendritic cells and B cells. Each MHC class II molecule is a heterodimer composed of two homologous subunits, alpha chain (with α1 and α2 domains) and beta chain (with β1 and β2 domains). Peptides, which are derived from extracellular proteins, enter the cells via endocytosis, are digested in the lysosomes and further bind to MHC class II molecules for presentation on the membrane.

Antigen-specific activation or regulation of CD4+ T cells is a multistep process in which co-ligation of the T cell receptor (TCR) with complexes of MHC II/peptide on the surface of APCs plays a central role.

MHC class II molecules with bound self peptides presented by professional APCs play a central role in activating specific CD4+ T cells involved in autoimmune diseases such as type 1 diabetes (T1D).

T1D (also known as juvenile diabetes) occurs when the autoimmune destruction of pancreatic beta-islet cells prevents production of the hormone insulin. This causes an inability to regulate glucose metabolism, which results in dangerously raised blood glucose concentrations. It is generally accepted that thymus-derived lymphocytes (T cells) are critically involved in the onset and progression of type 1 diabetes, but the antigens that initiate and drive this destructive process remain poorly characterized—although several candidates have been considered such as insulin, insulin derivatives, islet-specific glucose-6-phosphatase catalytic subunit related peptide (IGRP), carboxypeptidase H, insulinoma-associated antigen (IA-2), glutamic acid decarboxylase (GAD65), carboxypeptidase E and heat shock protein 60.

Genetic factors affecting susceptibility to T1D include the insulin-dependent diabetes mellitus 1 (IDDM1) gene (GeneID 7924) which is located in the MHC class II region on chromosome 6p21 and which is likely to be responsible for the histocompatibility disorder characteristic of type 1 diabetes in which pancreatic beta cells display improper antigens to T cells. Linkage analysis shows that 96% of diabetic patients express HLA-DR3 and/or HLA-DR4, including over-representation of the HLA-DR3/DR4 heterozygosity in diabetics as compared with non-diabetic controls. These alleles are tightly linked to HLA-DQ alleles that confer susceptibility to IDDM. Other non-genetic factors which might affect susceptibility to type 1 diabetes include diet, which affects gut flora, intestinal permeability, and immune function in the gut.

Glutamate decarboxylase (GAD) enzyme in mammals exists in two isoforms-GAD 65 kDa (GAD2; GeneID 2572) and GAD 67 kDa (GAD1; GeneID 2571). While both isoforms are expressed in brain, GAD 65 kDa is also expressed in the pancreas. Importance of GAD as an islet autoantigen initially highlighted because of the high frequency of auto-antibodies in patient sera directed against this molecule. Subsequent studies led to a large accumulation of data, which support the notion that a dominant CD4+ T-cell response to GAD 65 kDa is a relevant marker for cellular autoimmunity in T1D (Nepom G T. 2003. Conversations with GAD. J Autoimmun. 20:195-8).

Based on the high association of the HLA-DR4 gene to T1D, many epitope identification studies were done, revealing a limited number of GAD peptides presented by the DR4 molecule (Nepom, G. T., et al., 2001). Human CD4+ T cell responses to the DR4/GAD peptides were obtained both among T1D patients and controls (Masewicz, S. A., et al., 2002; Bach, J. M. et al., 1997; Ou, D., et al., 1999; Roep, B. O., et al., 1999; Lohmann, T. et al., 1996; Rharbaoui, et al., 1999), suggesting that the potential for autoreactivity is present in many individuals.

$GAD_{555-567}$ peptide in the context of HLA-DR4 has been shown to be an efficiently processed immunodominant epitope in patients with type 1 diabetes and DR401 transgenic mice (Reijonen, H., et al., 2002; Patel, S. D., et al., 1997). DR4/$GAD_{555-567}$ tetramer detection of autoreactive CD4+ T-cells were observed in the peripheral blood of T1D and at risk subjects but not in healthy controls (Oling, V., et al., 2005).

Additional background art includes U.S. Patent Application Publication No. 20020114816 (ENDL, JOSEF; et al.); U.S. Patent Application Publication No. 20090155292; U.S. Patent Application No. 20030166277; and Krogsgaard M., et al., 2000, Journal of Experimental Medicine, Pages 1395-1412).

SUMMARY OF THE INVENTION

According to an aspect of some embodiments of the present invention there is provided an isolated complex comprising a major histocompatibility complex (MHC) class II and a glutamic acid decarboxylase (GAD) autoantigenic peptide, wherein the GAD autoantigenic peptide comprises a core amino acid sequence set forth by SEQ ID NO:14 (GAD556-565, FFRMVISNPA), wherein the GAD autoantigenic peptide is covalently attached to a beta chain of the MHC class II.

According to an aspect of some embodiments of the present invention there is provided an isolated antibody comprising an antigen binding domain capable of specifically binding a complex composed of a major histocompatibility complex (MHC) class II and a Glutamic acid decarboxylase (GAD) autoantigenic peptide, wherein the isolated antibody does not bind to the MHC class II in an absence of the GAD autoantigenic peptide, wherein the isolated antibody does not bind to the GAD autoantigenic peptide in an absence of the MHC class II.

According to an aspect of some embodiments of the present invention there is provided an isolated antibody comprising complementarity determining regions (CDRs) set forth by SEQ ID NOs: 37-39 and 43-459 (CDRs 1-3 of heavy chain and light chain of G3H8), or SEQ ID NOs: 49-51 and 55-57 (CDRs 1-3 of heavy chain and light chain of G1H12).

According to an aspect of some embodiments of the present invention there is provided an isolated high affinity entity comprising an antigen binding domain capable of specifically binding a complex composed of a major histocompatibility complex (MHC) class II and a glutamic acid decarboxylase (GAD) autoantigenic peptide, wherein the isolated antibody does not bind to the MHC class II in an absence of the GAD autoantigenic peptide, wherein the isolated high affinity entity does not bind to the GAD autoantigenic peptide in an absence of the MCH class II.

According to an aspect of some embodiments of the present invention there is provided an isolated high affinity entity comprising an antigen binding domain being isolatable by the complex of some embodiments of the invention.

According to an aspect of some embodiments of the present invention there is provided an isolated high affinity entity comprising an antigen binding domain being isolatable by the complex of some embodiments of the invention.

According to an aspect of some embodiments of the present invention there is provided an isolated high affinity entity comprising an antigen binding domain capable of specifically binding to the isolated complex of some embodiments of the invention. provided An isolated high affinity entity comprising complementarity determining regions (CDRs) set forth by SEQ ID NOs:37-39 and 43-45 (CDRs 1-3 of heavy chain and light chain of G3H8), or SEQ ID NOs:49-51 and 55-57 (CDRs 1-3 of heavy chain and light chain of G1H12).

According to an aspect of some embodiments of the present invention there is provided A method of isolating an high affinity entity which specifically binds to a complex composed of a major histocompatibility complex (MHC) class II and a glutamic acid decarboxylase (GAD) autoantigenic peptide, comprising:

(a) screening a library comprising a plurality of high affinity entities with the isolated complex; and (b) isolating at least one high affinity entity which specifically binds to the isolated complex of some embodiments of the invention and not to the MHC class II in the absence of the GAD autoantigenic peptide or to the GAD autoantigenic peptide in an absence of the MHC class II, thereby isolating the high affinity entity which specifically binds to the complex of the MHC class II and the GAD autoantigenic peptide.

According to an aspect of some embodiments of the present invention there is provided a molecule comprising the isolated antibody of any of some embodiments of the invention or the high affinity entity of any of some embodiments of the invention, being conjugated to a detectable moiety.

According to some embodiments of the invention, an isolated antibody comprising a multivalent form of the antibody or of the antibody fragment of some embodiments of the invention.

According to an aspect of some embodiments of the present invention there is provided a molecule comprising the isolated antibody of any of some embodiments of the invention or the high affinity entity of any of some embodiments of the invention, being conjugated to a therapeutic moiety.

According to an aspect of some embodiments of the present invention there is provided a pharmaceutical composition comprising as an active ingredient the isolated antibody of some embodiments of the invention, the high affinity entity of some embodiments of the invention, or the molecule of some embodiments of the invention, and a pharmaceutically acceptable carrier.

According to an aspect of some embodiments of the present invention there is provided a method of detecting presentation of a glutamic acid decarboxylase (GAD) autoantigenic peptide on a cell, comprising contacting the cell with the antibody of any of some embodiments of the invention, the high affinity entity of some embodiments of the invention, or the molecule of some embodiments of the invention, under conditions which allow immunocomplex formation, wherein a presence or a level above a predetermined threshold of the immunocomplex is indicative of presentation of the GAD autoantigenic peptide on the cell.

According to an aspect of some embodiments of the present invention there is provided a method of diagnosing type 1 diabetes (T1D) in a subject, comprising contacting a cell of the subject with the antibody of some embodiments of the invention, the high affinity entity of some embodiments of the invention, or the molecule of some embodiments of the invention, under conditions which allow immunocomplex formation, wherein a presence or a level above a pre-determined threshold of the immunocomplex in or on the cell is indicative of the type 1 diabetes in the subject.

According to an aspect of some embodiments of the present invention there is provided a method of treating type 1 diabetes (T1D), comprising administering to a subject in need thereof a therapeutically effective amount of the antibody of some embodiments of the invention, the high affinity entity of some embodiments of the invention, or the molecule of some embodiments of the invention, or the pharmaceutical composition of some embodiments of the invention, thereby treating the type 1 diabetes.

According to an aspect of some embodiments of the present invention there is provided a kit for detecting presence and/or level of a complex which comprises major histocompatibility complex (MHC) class II and a GAD autoantigenic peptide, the kit comprising the antibody of some embodiments of the invention, the high affinity entity of some embodiments of the invention, or the molecule of some embodiments of the invention.

According to an aspect of some embodiments of the present invention there is provided an isolated polynucleotide comprising a first nucleic acid sequence encoding an extracellular domain of an MHC class II beta chain and a second nucleic acid sequence encoding a glutamic acid decarboxylase (GAD) autoantigenic peptide, wherein the second nucleic acid sequence being translationally fused upstream of the first nucleic acid sequence or between the nucleic acid sequence encoding amino acids 1-6 of the extracellular domain.

According to an aspect of some embodiments of the present invention there is provided a nucleic acid system comprising:

(i) a first polynucleotide comprising the isolated polynucleotide of some embodiments of the invention; and (ii) a second polynucleotide which comprises a forth nucleic acid sequence encoding an MHC class II alpha chain.

According to an aspect of some embodiments of the present invention there is provided a composition of matter comprising the isolated complex of some embodiments of the invention and a functional moiety conjugated thereto.

According to an aspect of some embodiments of the present invention there is provided a pharmaceutical composition comprising the composition of matter of some embodiments of the invention and a therapeutically acceptable carrier.

According to some embodiments of the invention, the GAD autoantigenic peptide is covalently bound at a C terminus thereof to an N-terminus of an extracellular domain of a beta chain of the MHC class II.

According to some embodiments of the invention, the GAD autoantigenic peptide is covalently embedded between amino acids 1-6 of an extracellular domain of a beta chain of the MHC class II.

According to some embodiments of the invention, the GAD autoantigenic peptide is covalently attached to the beta chain between the third and fourth amino acid of a mature polypeptide of the MHC class II beta chain.

According to some embodiments of the invention, the antigen binding domain is capable of specifically binding to a native conformation of the complex composed of the MHC class II and the GAD autoantigenic peptide.

According to some embodiments of the invention, the antigen binding domain is capable of specifically binding to a native conformation of a complex composed of the MHC class II and the GAD autoantigenic peptide.

According to some embodiments of the invention, the antigen binding domain is further capable of specifically binding to the isolated complex of some embodiments of the invention.

According to some embodiments of the invention, the antibody further specifically binds to a native conformation of the complex of the MHC class II and the GAD autoantigenic peptide.

According to some embodiments of the invention, the GAD autoantigenic peptide is flanked at a C-terminus thereof by a linker peptide.

According to some embodiments of the invention, the GAD autoantigenic peptide being translationally fused to the extracellular domain.

According to some embodiments of the invention, the beta chain of the MHC class II comprises a first member of a binding pair which upon expression in eukaryotic cells binds to a second member of the binding pair, wherein the second member is comprised in an alpha chain of the MHC class II, wherein the beta chain and the alpha chain form the MHC class II.

According to some embodiments of the invention, the isolated complex having a structural conformation which enables isolation of an antibody which comprises an antigen binding domain capable of specifically binding to a native conformation of a complex composed of the MHC class II and the GAD autoantigenic peptide.

According to some embodiments of the invention, the native conformation comprises the structural conformation of the complex of the GAD autoantigenic peptide and the MHC class II when presented on an antigen presenting cell (APC).

According to some embodiments of the invention, the GAD autoantigen comprises no more than 30 amino acids.

According to some embodiments of the invention, the GAD autoantigen is set forth by SEQ ID NO: 22 (NFFRM-VISNPAAT, $GAD_{555-567}$).

According to some embodiments of the invention, the beta chain of the MHC class II comprises a first member of a binding pair which upon expression in eukaryotic cells binds to a second member of the binding pair, wherein the second member is comprised in an alpha chain of the MHC class II, wherein the beta chain and the alpha chain form the MHC class II.

According to some embodiments of the invention, the MHC class II is selected from the group consisting of HLA-DM, HLA-DO, HLA-DP, HLA-DQ, and HLA-DR.

According to some embodiments of the invention, the beta chain of the MHC class II is DR-B1*0401.

According to some embodiments of the invention, the alpha chain of the MHC class II is DR-A1*0101.

According to some embodiments of the invention, the antigen binding domain comprises complementarity determining regions (CDRs) set forth by SEQ ID NOs:37-39 and 43-45 (CDRs 1-3 of heavy chain and light chain of G3H8), or 49-51 and 55-57 (CDRs 1-3 of heavy chain and light chain of G1H12).

According to some embodiments of the invention, the multivalent form is an IgG antibody.

According to some embodiments of the invention, the antibody is capable of blocking presentation of the complex comprising the MHC class II and the GAD autoantigenic peptide on antigen presenting cells.

According to some embodiments of the invention, the antibody is capable of killing antigen presenting cells which display the complex comprising the MHC class II and the GAD autoantigenic peptide.

According to some embodiments of the invention, the kit further comprising instructions for use in diagnosing type 1 diabetes.

According to some embodiments of the invention, the antibody does not bind to the MHC class II in an absence of the GAD autoantigenic peptide, wherein the antibody does not bind to the GAD autoantigenic peptide in an absence of the MHC class II.

According to some embodiments of the invention, the isolated complex does not include a heterologous immunoglobulin attached thereto.

According to some embodiments of the invention, the isolated polynucleotide further comprises a nucleic acid sequence encoding a linker peptide being translationally fused downstream of the second nucleic acid sequence.

According to some embodiments of the invention, the isolated polynucleotide further comprises a third nucleic acid sequence encoding a first member of a binding pair which upon expression in eukaryotic cells binds to a second member of the binding pair.

According to some embodiments of the invention, the second polynucleotide further comprises a fifth nucleic acid construct encoding the second member of the binding pair.

According to some embodiments of the invention, the high affinity entity is selected from the group consisting of an antibody, an antibody fragment, a phage displaying an antibody, a peptibody, a bacteria displaying an antibody, a yeast displaying an antibody, and a ribosome displaying an antibody.

According to some embodiments of the invention, the high affinity entity is an antibody or an antibody fragment.

According to some embodiments of the invention, the functional moiety comprises an antibody or a fragment specific for a cell surface marker.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 1A, 1B, 1C, 1D:
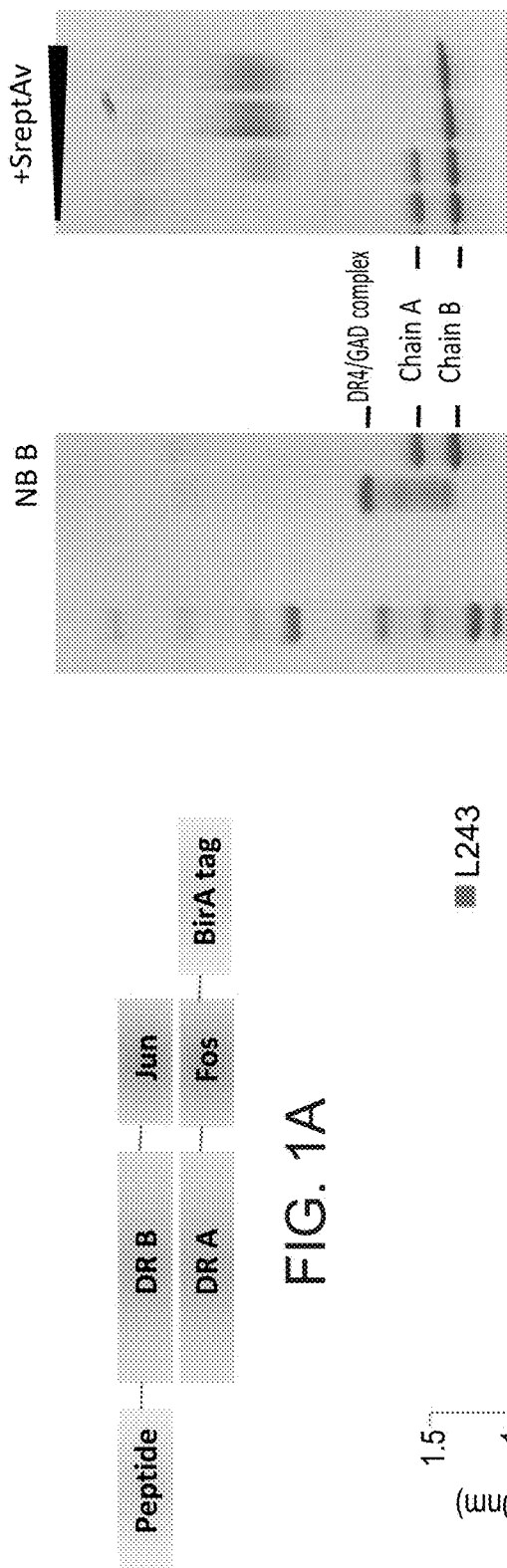

FIGS. 1A-D depict the production of recombinant DR4/GAD$_{555-567}$ complex. FIG. 1A-A schematic presentation of the DR-A and DR-B constructs for production in S2 cells. FIGS. 1B-C—SDS-PAGE analyses of purified DR4/GAD complex. The DR4 complex is highly purified and forms SDS-stable heterodimer. Boiling of the sample disassociates the DR-A and DR-B chains (FIG. 1B; "B"—boiled, "NB"—not boiled). High biotinylation levels were verified by incubation of purified DR4-GAD complexes with increasing concentrations of streptavidin prior to SDS-PAGE analysis (FIG. 1C). All detectable DR-A chains were biotinylated and therefore bound to the streptavidin. FIG. 1D—DR4/GAD complex is folded in the right native conformation. ELISA binding assay of immobilized DR4/GAD-555-567 complex with diluted concentrations of anti-DR conformation sensitive mAb (L243) and anti-DR mAb TU39.

FIGS. 2A-E depict characterization of G3H8 and G1H12 TCRL Fabs directed at DR4/GAD$_{555-567}$. FIG. 2A—ELISA of purified TCRL Fabs with immobilized DR4/GAD$_{555-567}$, control complex DR4/HA$_{307-319}$, GAD$_{555-567}$ peptide, and HA$_{307-319}$ peptide. Anti-DR mAb L243 was used to determine the correct conformation and stability of the bound complexes during the binding assay. Note the specific binding of Fab antibodies G1A1, G1A2 and G3H8 (clone G3H8) and G1H12 (clone G1H12) to the DR4/GAD$_{555-567}$ complex as compared to absence of binding to the other control peptide complexes. FIG. 2B—Flow cytometry analysis of Fab G3H8 binding to Preiss APCs pulsed with GAD$_{555-567}$ peptide or the control peptides: InsA$_{1-15}$, CII$_{261-273}$, Ha$_{307-319}$. FIG. 2C—Flow cytometry analysis of Fab G3H8 to the naturally processed peptide GAD$_{552-572}$. FIG. 2D—binding intensity of the Fab G3H8 antibody at various antibody's concentrations (20, 50 and 100 µg/ml). FIG. 2E—binding intensity of the Fab G3H8 to various loaded GAD$_{555-567}$ peptide concentrations (0, 50, 75, 150, 300 and 400 µg/ml). Note that the binding intensity is dose-dependent on antibody's concentration (FIG. 2D) and peptide concentration (FIG. 2E).

Figure 3A:
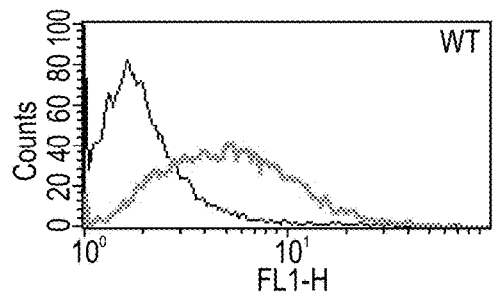
Figure 3B:
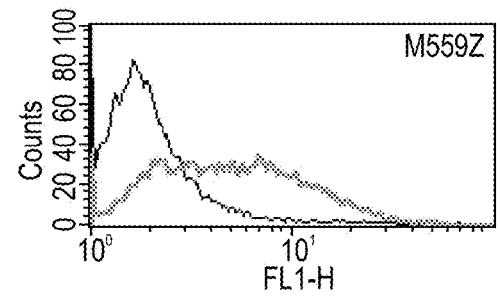
Figure 3C:
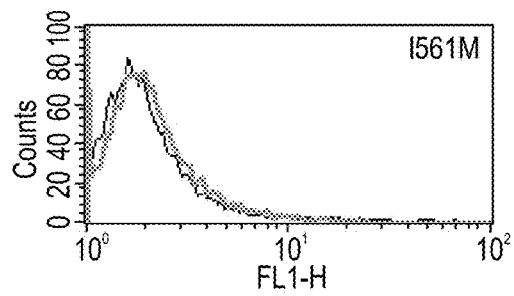
Figure 3D:
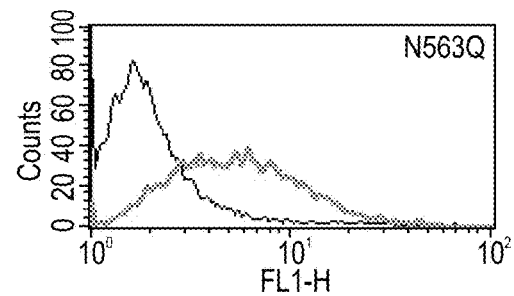
Figure 3E:
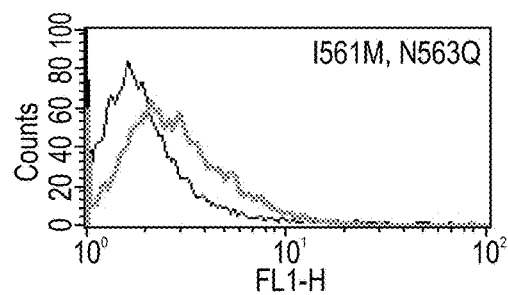
Figure 3F:
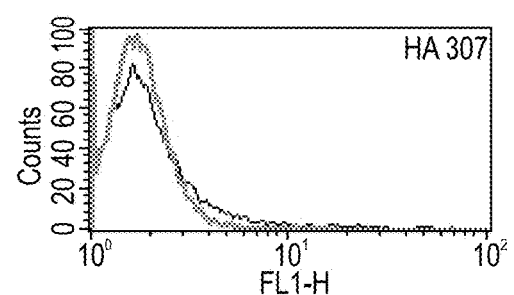

FIGS. 3A-F are flow cytometry analyses depicting the mapping of the recognition epitope of DR4/GAD TCRLs. Flow cytometry analysis of Fab G3H8 binding to Preiss APCs pulsed with wild type (WT) GAD$_{555-567}$ peptide (FIG. 3A), GAD altered peptide ligand (APL): M559Z (FIG. 3B), I561M (FIG. 3C), N563Q (FIG. 3D), I561M+N563Q (FIG. 3E), and the control HA307-319 peptide (FIG. 3F).

Figure 4A:
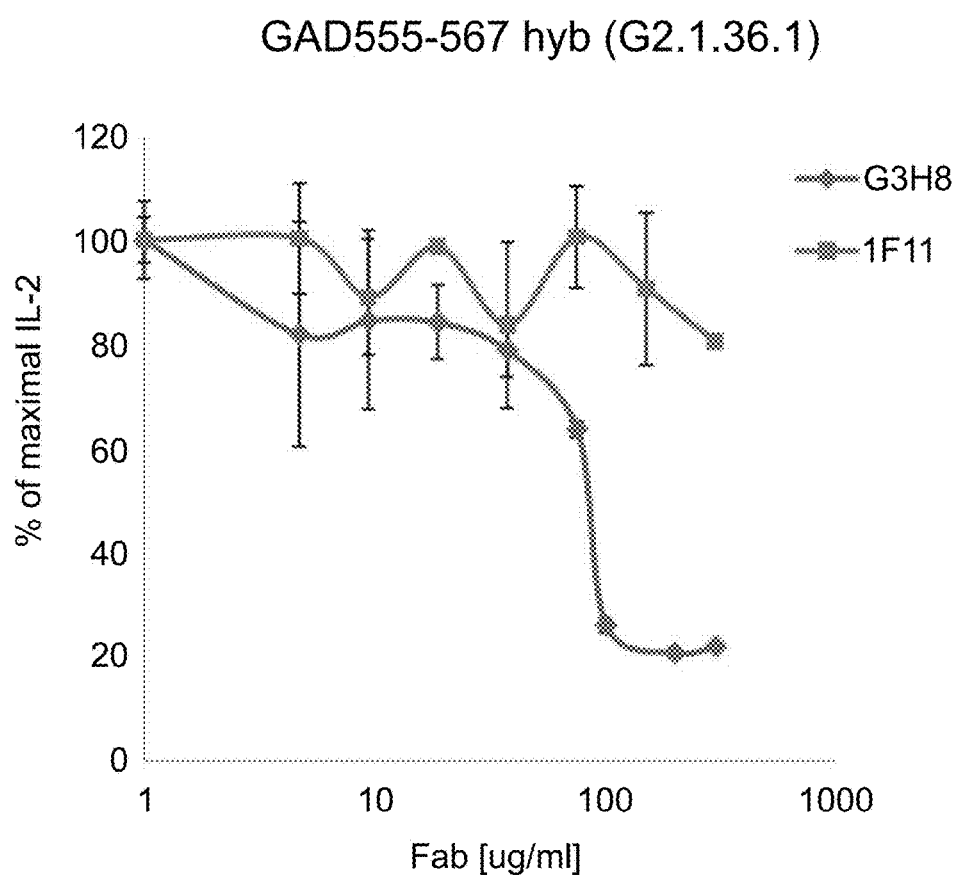
Figure 4B:
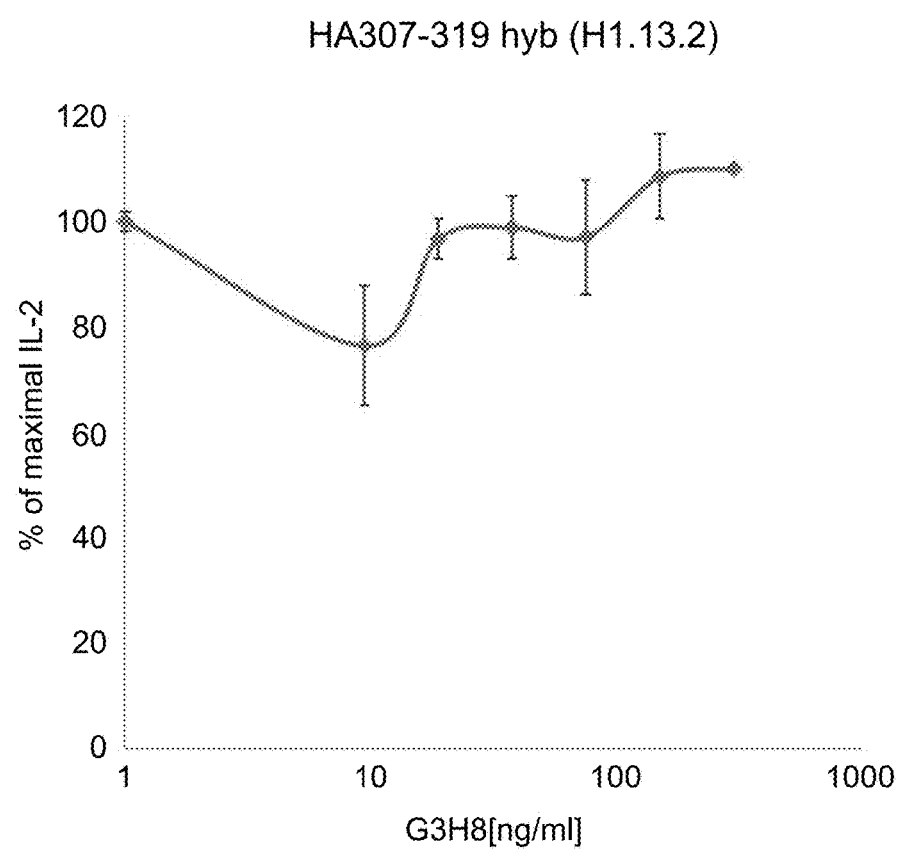

FIGS. 4A-B are graphs depicting G3H8 Fab ability to inhibit DR4-restricted GAD-specific T cell response to GAD$_{555-567}$ peptide. T cell hybridomas were Ag-specific activated by peptide-pulsed DR0401-Tg splenocytes in the presence of increasing Fab concentrations. FIG. 4A—G2.1.38.1 hybridoma specific to the DR4/GAD$_{555-567}$ epitope was inhibited in a dose-depended manner by G3H8 Fab and not by control 1F11 TCRL Fab. FIG. 4B—H1.13.2 hybridoma specific to the DR4/Ha$_{307-319}$ epitope was not inhibited by G3H8 TCRL Fab. These results demonstrate that G3H8 can inhibit GAD$_{555-567}$ specific DR0401 restricted T cell hybridoma response.

FIGS. 5A-E are photographs depicting immunofluorescence analysis using G3H8 Fab antibody demonstrating GAD$_{555-567}$ presentation by DR4 in islets of Langerhans of diabetic mice. Frozen sections from diabetic B7/0401 (FIGS. 5A-C) and C57BL/6 (FIGS. 5D-E) mice were subjected to immunostaining analysis using the G3H8 antibody followed by staining with an anti-human IgG-Alexa-488 (green) and 4',6-diamidino-2-phenylindole (DAPI; blue). Sections were visualized by Cell Observer—Zeiss Fluorescent Microscope. Note the green labeling in islets of Langerhans in B7/041 diabetic mice (FIGS. 5A-C) and the absence of labeling in control C57BL/6 mice (FIGS. 5D-E).

FIGS. 6A-D depict the amino acid [FIGS. 6A (SEQ ID NO:1) and 6C (SEQ ID NO:3)] and nucleic acid [FIGS. 6B (SEQ ID NO:2) and 6D (SEQ ID NO:4)] sequence of the G3H8 Fab antibody (Anti HLA-DR4/GAD555-567 Fab) light chain (FIGS. 6A-B) and heavy chain (FIGS. 6C-D). CDRs (by Kabat definition) are underlined (SEQ ID NOs: 37-39 CDRs 1-3 for light chain; SEQ ID NOs:43-45 CDRs 1-3 for heavy chain; SEQ ID NOs:40-42 nucleic acid sequence encoding CDRs 1-3 of light chain; SEQ ID NOs: 46-48 nucleic acid sequence encoding CDRs 1-3 of heavy chain). For heavy chains: Black letter—VH (variable domain) Blue letters—constant 1 domain (CH1); Red letters—Connector; Purple letters—His tag; Green letters—Myc tag.

FIGS. 7A-D depict the amino acid [FIGS. 7A (SEQ ID NO:5) and 7C (SEQ ID NO:7)] and the nucleic acid [FIGS. 7B (SEQ ID NO:6) and 7D (SEQ ID NO:8)] sequence of the G1H12 (Anti HLA-DR4/GAD555-567 Fab) antibody light chain (FIGS. 7A-B) and heavy chain (FIGS. 7C-D). CDRs (by Kabat definition) are underlined (SEQ ID NOs: 49-51 CDRs 1-3 for light chain; SEQ ID NOs:55-57 CDRs 1-3 for heavy chain; SEQ ID NOs:52-54 nucleic acid sequence encoding CDRs 1-3 of light chain; SEQ ID NOs:58-60 nucleic acid sequence encoding CDRs 1-3 of heavy chain). For heavy chains: Black letter—VH (variable domain) Blue letters—CH1 (constant 1 domain); Red letters—Connector; Purple letters—His tag; Green letters—Myc tag.

FIGS. 8A-B depict the amino acid sequence of the recombinant beta (DRB1*0401, SEQ ID NO:9; FIG. 8A) and alpha (DRA1*0101, SEQ ID NO:10; FIG. 8B) chains according to some embodiments of the invention. FIG. 8A—leader peptide—highlighted in yellow, beta chain (red), GAD-555-567 peptide (blue), linker (black and underlined), Jun dimerization domain (Green); FIG. 8B—leader peptide—highlighted in yellow, alpha chain (red), GAD-555-567 peptide (blue), linker (black and underlined), Jun dimerization domain (Green) BirA tag (purple).

FIGS. 9A-B depict the nucleic acid sequence of the recombinant beta (DRB1*0401, SEQ ID NO:11; FIG. 9A) and alpha (DRA1*0101, SEQ ID NO:12; FIG. 9B) chains according to some embodiments of the invention. FIG. 9A—leader peptide—highlighted in yellow, beta chain (red), GAD-555-567 peptide (blue), linker (black and underlined), Jun dimerization domain (Green); FIG. 9B—leader peptide—highlighted in yellow, alpha chain (red), GAD-555-567 peptide (blue), linker (black and underlined), Jun dimerization domain (Green) BirA tag (purple).

Figures 10A, 10B:
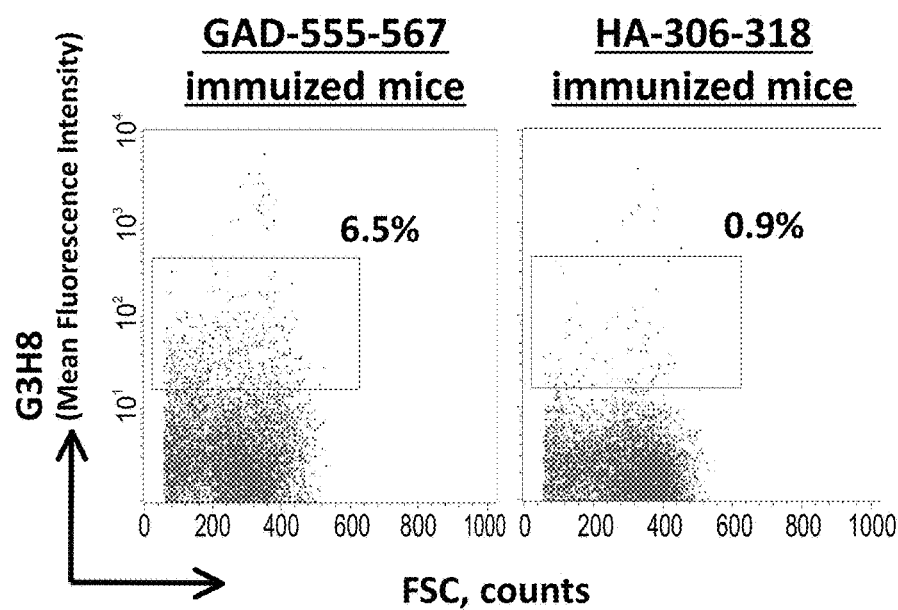

FIGS. 10A-B are histograms depicting flow cytometry analyses depicting binding of G3H8 to murine lymph node cells. Flow cytometry analysis of G3H8 IgG binding to cell suspensions derived from inguinal (draining) lymph nodes (LN) of HLA-DR4 Transgenic (Tg) mice immunized with GAD-555-567 (FIG. 10A) or HA-306-318 (FIG. 10B). Y-axis depicts mean fluorescence intensity of positive cells. X-axis depicts forward side scatter (FCS) counts. Note that while the G3H8 antibody detects APCs presenting the HLA-DR4-GAD-555-567 complexes (6.5% positive cells) from HLA-DR4 Transgenic mice immunized with GAD-555-567 (FIG. 10A), this antibody does not detect cells expressing the HLA-DR4-HA-306-318 (background level of 0.9%) from HLA-DR4 Transgenic mice immunized with HA-306-318 (FIG. 10B). Non-draining para-aortic LN and spleen cell suspensions from GAD-immunized mice did not show staining above background levels obtained from the HA-immunized mice (data not shown). These results demonstrate specific detection of GAD-555-567 presenting APCs from inguinal lymph node of GAD-immunized DR4 mice.

Figure 11B:
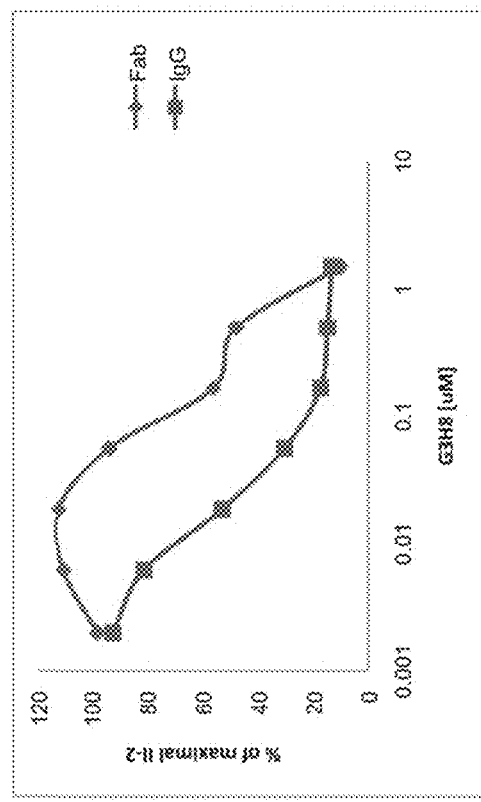
Figure 11A:
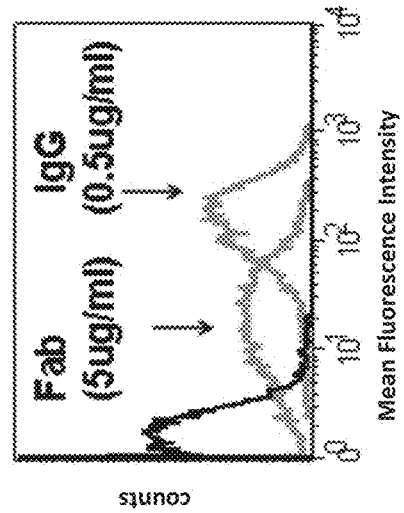
Figure 11C:
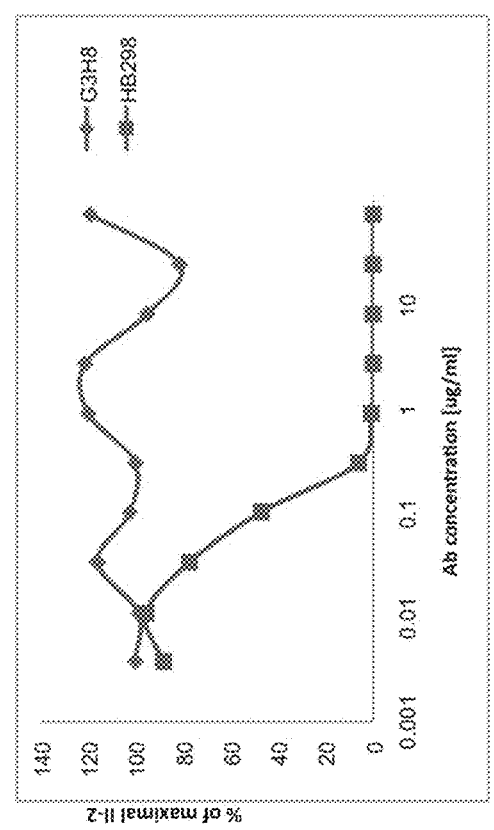

FIGS. 11A-C are histograms depicting the increased binding and T-cell blocking capacity of the G3H8 IgG1 antibody compared to that of the G3H8 Fab. FIG. 11A—A histogram depicting binding of Fab or IgG G3H8 antibodies to DR4+ Priess cells loaded with the GAD555-567 peptide. Note that the fully human G3H8 IgG1 Ab maintains specificity to DR4/GAD and binds at much higher intensity to cells with 10-fold lower concentration compared to the Fab. FIG. 11B—A histogram depicting blocking of GAD555-567 specific, DR4 restricted T cell response. The G3H8 Fab and IgG compete with the autoreactive TCR on the GAD555-567 hybridoma and inhibit the GAD-specific response in a dose-dependent manner. IgG inhibition is >10 fold more efficient compared to the Fab inhibition. FIG. 11C—A histogram depicting blocking of HA-306-318 specific, DR4 restricted T cell response by HB298 but not with G3H8. G3H8 IgG Ab did not inhibit other T cell specificity against a flu peptide (HA-306-318). This is compared to the inhibition obtained by control anti-DR mAb (HB298). These results demonstrate the specificity of the G3H8 antibody towards the DR4/GAD-555-567 and not to unrelated complexes (e.g., of flu).

DESCRIPTION OF SPECIFIC EMBODIMENTS OF THE INVENTION

The present invention, in some embodiments thereof, relates to isolated complexes of MHC class II and GAD autoantigenic peptides, isolated high affinity entities such as antibodies which specifically bind to same and, more particularly, but not exclusively, to uses thereof for diagnosing and treating type I diabetes.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have generated MHC class II-GAD autoantigenic peptides complexes which were used for the isolation of T-cell receptor like antibodies useful for studying antigen presentation during progression of type I diabetes as well as for diagnosing and treating type I diabetes.

As described in the Examples section which follows, the present inventors generated an isolated complex of MHC class II and a $GAD_{555-567}$ antigenic peptide in which the antigenic peptide is covalently linked to the N-terminus of the MHC class II beta chain (FIG. 1A, Example 1). The MHC class II/GAD peptide complex was used for isolating specific soluble antibodies (e.g., Fabs) which specifically bind the MHC class II (e.g., DR4) when bound to the $GAD_{555-567}$ antigenic peptide both in vitro and in the native conformation (e.g., when presented on cells), but not to MHC class II in the absence of the specific antigenic peptide (FIGS. 2A-B). In addition, these antibodies were found capable of binding to cells loaded with the naturally T1D-associated epitope $GAD_{552-572}$ (SEQ ID NO:13) (FIG. 2C, Example 1 and data not shown); exhibit T-cell receptor like specificity at various antibody's concentrations (FIG. 2D, Example 1) and various antigenic-peptide concentrations (FIG. 2E, Example 1), with increasing antibody's staining in correlation with increases in the total MHC class II/antigenic peptide complexes on the cells. These results show that the isolated antibodies can be used in quantifying antigen presentation of antigen-presenting cells-of-interest. In addition, as described in Example 2, the isolated antibodies of the invention exhibit fine specificity to their targeted complex and differentially bind to complexes including a wild type peptide, but not to complexes with a mutated amino acid at position P5 of the MHC class II-GAD restricted antigenic peptide (FIGS. 3A-E). Furthermore, as shown in Example 3, G3H8 Fab was found to inhibit ~80% response of G2.1.36.1 T cell hybridoma specific to GAD-555-567 restricted by HLA-DR*0401 (FIG. 4A) but not the H1.13.2 hybridoma response to HA307-319 peptide restricted by HLA-DR*0401 (FIG. 4B), thus demonstrating an antigen-specific blocking of autoreactive T cells response to the autoreactive GAD-epitope by G3H8 Fab. In addition, as described in Example 4, the G3H8 Fab specifically bound to the MHC class II-$GAD_{555-567}$ complexes in islets of B7/DR4 diabetic mice (FIGS. 5A-C) and in infiltrated islets of B7/DR4 pre-diabetic mice (data not shown) but not to islets of C57B6 control mice (FIGS. 5D-E). Moreover, as described in Example 6, a whole IgG G3H8 antibody was generated and was shown to be specific towards cells presenting the HLA-DR4-GAD555-567 complexes ex vivo (FIGS. 10A-

B), with enhanced binding as compared to the G3H8 Fab (FIG. 11A), with higher potency (FIG. 11B) while maintaining the unique TCR-like specificity (FIG. 11C). Altogether, these results demonstrate the specificity of the antibodies, their use in diagnosing diabetes at early stages and the accessibility of the antibodies to the islets infiltrating APC, which is essential for therapeutic purposes, for blocking specific MHC class II/peptide events associated with the progression of the disease.

Thus, according to an aspect of some embodiments of the invention, there is provided an isolated complex comprising a major histocompatibility complex (MHC) class II and glutamic acid decarboxylase (GAD) autoantigenic peptide, wherein the GAD autoantigenic peptide comprises a core amino acid sequence set forth by SEQ ID NO:13 (GAD556-565, FFRMVISNPA), wherein the GAD autoantigenic peptide is covalently attached to a beta chain of the MHC class II. As used herein the term "isolated" refers to at least partially separated from the natural environment e.g., the human body.

According to some embodiments the isolated complex is soluble.

As used herein the phrase "major histocompatibility complex (MHC)" refers to a complex of antigens encoded by a group of linked loci, which are collectively termed H-2 in the mouse and human leukocyte antigen (HLA) in humans. The two principal classes of the MHC antigens, class I and class II, each comprise a set of cell surface glycoproteins which play a role in determining tissue type and transplant compatibility. In transplantation reactions, cytotoxic T-cells (CTLs) respond mainly against foreign class I glycoproteins, while helper T-cells respond mainly against foreign class II glycoproteins.

MHC class II molecules are expressed in professional antigen presenting cells (APCs) such as macrophages, dendritic cells and B cells. Each MHC class II molecule is a heterodimer composed of two homologous subunits, alpha chain (with α1 and α2 extracellular domains, transmembrane domain and short cytoplasmic tail) and beta chain (with β1 and β2 extracellular domains, transmembrane domain and short cytoplasmic tail). Peptides, which are derived from extracellular proteins, enter the cells via endocytosis, are digested in the lysosomes and further bind to MHC class II molecules for presentation on the membrane.

Various MHC class II molecules are found in humans. Examples include, but are not limited to HLA-DM, HLA-DO, HLA-DP, HLA-DQ (e.g., DQ2, DQ4, DQ5, DQ6, DQ7, DQ8, DQ9), HLA-DR (e.g., DR1, DR2, DR3, DR4, DR5, DR7, DRB, DR9, DR10, DR11, DR12, DR13, DR14, DR15, and DR16).

Non-limiting examples of DQ A1 alleles include 0501, 0201, 0302, 0301, 0401, 0101, 0102, 0104, 0102, 0103, 0104, 0103, 0102, 0303, 0505 and 0601.

Non-limiting examples of DQ B1 alleles include 0201, 0202, 0402, 0501, 0502, 0503, 0504, 0601, 0602, 0603, 0604, 0609, 0301, 0304, 0302 and 0303.

Non-limiting examples of DPA1 alleles include 01, e.g., 0103, 0104, 0105, 0106, 0107, 0108, 0109; 02, e.g., 0201, 0202, 0203; 03 e.g., 0301, 0302, 0303, 0401.

Non-limiting examples of DPB1 alleles include 01, e.g., 0101, 0102; 02 e.g., 0201, 0202, 0203; 03; 04, e.g., 0401, 0402, 0403; 05, e.g., 0501, 0502; 06; 08, e.g., 0801, 0802; 09, e.g., 0901, 0902; 10, e.g., 1001, 1002; 11 e.g., 1101, 1102; 13, e.g., 1301, 1302; 14, e.g., 1401, 1402; 15, e.g., 1501, 1502; 16, e.g., 1601, 1602; 17, e.g., 1701, 1702; 18, e.g., 1801, 1802; 19, e.g., 1901, 1902; 20, e.g., 2001, 2002; 21; 22; 23; 24; 25; 26, e.g., 2601, 2602; and 27.

Non-limiting examples of DP haplotypes include HLA-DPA1*0103/DPB1*0401 (DP401); and HLA-DPA1*0103/DPB1*0402 (DP402).

Non-limiting examples of DR B1 alleles include 0101, 0102, 0103, 0301, 0401, 0407, 0402, 0403, 0404, 0405, 0701, 0701, 0801, 0803, 0901, 1001, 1101, 1103, 1104, 1201, 1301, 1302, 1302, 1303, 1401, 1501, 1502, 1601 alleles.

Non-limiting examples of DR-DQ haplotypes include DR1-DQ5, DR3-DQ2, DR4-DQ7, DR4-DQ8, DR7-DQ2, DR7-DQ9, DR8-DQ4, DR8-DQ7, DR9-DQ9, DR10-DQ5, DR11-DQ7, DR12-DQ7, DR13-DQ6, DR13-DQ7, DR14-DQ5, DR15-DQ6, and DR16-DQ5.

According to some embodiments of the invention, the beta chain of the MHC class II complex is DR-B1*0401 (SEQ ID NO:15; native DR-B1*0401 molecule)

According to some embodiments of the invention, the alpha chain of the MHC class II is DR-A1*0101 (SEQ ID NO:16; native DR-A1*0101 molecule).

As used herein the phrase "glutamic acid decarboxylase (GAD)" refers to a family of proteins which are responsible for catalyzing the production of gamma-aminobutyric acid from L-glutamic acid. There are two major GAD enzymes in humans, GAD 65 kDa which is expressed in both brain and pancreas (GeneID 2572; encoded by GenBank accession No. NM_000818.2 (SEQ ID NO:17); NM_001134366.1 (SEQ ID NO:18); NP_000809.1 (SEQ ID NO:19)] and GAD 67 kDa which is expressed in brain [GeneID 2571; encoded by GenBank accession No. NM_000817.2 (SEQ ID NO:20); NP_000808.2 (SEQ ID NO:21)]. GAD 65 kDa has been identified as an autoantibody and an autoreactive T cell target in insulin-dependent diabetes.

As used herein the phrase "GAD autoantigenic peptide" refers to an antigen derived from a self GAD protein (i.e., an endogenous protein), which is expressed in pancreatic cells such as beta cells of the pancreas, and against which an inflammatory response is elicited as part of an autoimmune inflammatory response.

It should be noted that a GAD autoantigenic peptide is an MHC class II-restricted peptide, which when presented on antigen presenting cells (APCs) is recognized by specific T cells. Such a presentation by APCs generates an inflammatory response that can activate and recruit T cell and B cell responses against beta cells, including the generation of cytotoxic T cells and antibodies which kill and destroy beta cells and thus lead to a decreased insulin production.

The GAD autoantigenic peptide according to some embodiments of the invention comprises the core amino acid sequence set forth by SEQ ID NO:14 (GAD556-565, FFRMVISNPA).

Since the amino acid sequence of the autoantigen may vary in length between the same or different MHC class II alleles, the length of the autoantigenic peptides according to some embodiments of the invention may vary from at least 10 amino acids, to autoantigenic peptides having at least 10, 25, or up to 30 amino acids.

According to some embodiments of the invention, the GAD autoantigenic peptide includes a core amino acids of 10.

According to some embodiments of the invention, the length of the GAD autoantigenic peptide does not exceed about 100 amino acids, e.g., does not exceed about 50 amino acids, e.g., does not exceed about 30 amino acids.

According to some embodiments of the invention, the GAD autoantigenic peptide comprises the amino acid sequence selected from the group consisting of SEQ ID NOs: 61, 62 and 22 and no more than 30 amino acids in length.

According to some embodiments of the invention, the GAD autoantigenic peptide is selected from the group consisting of SEQ ID NOs:61, 62 and 22.

According to some embodiments of the invention, the GAD autoantigenic peptide is $GAD_{555-567}$ (NFFRMVISN-PAAT; SEQ ID NO:22).

According to some embodiments of the invention, the length of the GAD autoantigenic peptide includes at least 10 and no more than 30 amino acids.

In addition, it should be noted that although some amino acids in each autoantigenic peptide are conserved between various alleles of MHC class II and cannot be substituted, other amino acids can be substituted with amino acids having essentially equivalent specificity and/or affinity of binding to MHC molecules and resulting in equivalent T cell epitope as the amino acid sequences shown in the exemplary autoantigens described above and in Table 3 (Example 5 of the Examples section). Thus, the core amino acids are required for recognition with the respective MHC class II molecule. Identification of the core amino acids for each autoantigenic peptide can be done experimentally, e.g., by mutagenesis of the amino acids constituting the autoantigenic peptide and detection of: (i) binding to the restricted MHC class II molecules; (ii) Stimulating the restricted T cell response. For example, for the $GAD_{555-567}$ the core amino acids are the amino acids at positions 556-565. The core amino acid sequence consists of anchor residues and the T-cell receptor (TCR) contact residues. Anchor residues in the sequence NFFRMVISNPAAT (SEQ ID NO: 22) are the P1 (F557), P4 (V560), P6 (S562), and P9 (A565) MHC pocket-binding residues. TCR contact residues in the sequence NFFRMVISNPAAT (SEQ ID NO: 22) are at positions F556, R558, M559, I561, N563. Accordingly, the core amino acids of the GAD555-567 autoantigenic peptide are GAD556-565 (FFRMVISNPA, SEQ ID NO:14).

The invention according to some embodiments thereof also concerns peptide variants whose sequences do not completely correspond with the aforementioned amino acid sequences but which only have identical or closely related "anchor positions". The term "anchor position" in this connection denotes an essential amino acid residue for binding to a MHC class II complex (e.g., DR1, DR2, DR3, DR4 or DQ).

The anchor position for the DRB1*0401 binding motif are for example stated in Hammer et al., Cell 74 (1993), 197-203. Such anchor positions are conserved in the GAD autoantigenic peptide or are optionally replaced by amino acid residues with chemically very closely related side chains (e.g. alanine by valine, leucine by isoleucine and vice versa). The anchor position in the peptides according to some embodiments of the invention can be determined in a simple manner by testing variants of the aforementioned specific peptides for their binding ability to MHC molecules. Peptides according to some embodiments of the invention are characterized in that they have an essentially equivalent specificity or/and affinity of binding to MHC molecules as the aforementioned peptides. Homologous peptides having at least 50%, e.g., at least 60%, 70%, 80%, 90%, 95% or more identity to the diabetes-associated autoantigenic peptides described herein are also contemplated by some embodiments of the invention.

It should be noted that each of the above described GAD autoantigenic peptides can be complexed with an MHC class II allele. Such MHC class II specific alleles are known in the art. Non-limiting examples of MHC class II alleles and their restricted autoantigenic peptides are illustrated in Table 3 in Example 5 of the Examples section which follows.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH$_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time. According to some embodiments of the invention, but not in all cases necessary, these modifications should exclude anchor amino acids.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The peptides of the invention are preferably utilized in a linear form, although it will be appreciated that in cases where cyclicization does not severely interfere with peptide characteristics, cyclic forms of the peptide can also be utilized.

The peptides of the invention may include one or more non-natural or natural polar amino acids, including but not limited to serine and threonine which are capable of increasing peptide solubility due to their hydroxyl-containing side chain.

The peptides of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965. Large scale peptide synthesis is described by Andersson Biopolymers 2000; 55(3):227-50.

According to some embodiments of the invention, the isolated complex which comprises the MHC class II and the GAD autoantigenic peptide has a structural conformation which enables isolation of a high affinity entity which comprises an antigen binding domain capable of specifically binding to a native conformation of a complex composed of the MHC class II and the diabetes type I GAD autoantigenic peptide.

According to some embodiments of the invention, the high affinity entity (e.g., the antibody) does not bind to the MHC class II in an absence of the GAD autoantigenic peptide, wherein the isolated high affinity entity does not bind to the GAD autoantigenic peptide in an absence of the MHC class II.

The phrase "MHC class II in the absence of the GAD autoantigenic peptide" as used herein encompasses an empty MHC class II complex (i.e., devoid of any antigenic peptide) as well as an MHC class II complex which is bound to another antigen peptide which is not the GAD autoantigenic peptide of some embodiments of the invention, e.g., a different MHC class II-restricted antigenic peptide.

The phrase "GAD autoantigenic peptide in an absence of the MHC class II" as used herein encompasses the GAD autoantigenic peptide of some embodiments of the invention when not bound to the MHC class II complex as well as to the GAD autoantigenic peptide of some embodiments of the invention when bound to another MHC class II complex, e.g., a different allele of an MHC class II beta or alpha chain than the chain(s) used for forming the complex of some embodiments of the invention.

According to some embodiments of the invention, the isolated complex which comprises the MHC class II and the GAD autoantigenic peptide does not include an heterologous immunoglobulin (e.g., an Fc, Fab and/or a single chain Fv antibody) attached thereto (either a covalent or a non-covalent attachment to the MHC class II molecules, e.g., via the C'-terminus of the MHC class II molecules).

According to some embodiments of the invention, the isolated complex has a structural conformation which enables isolation of an high affinity entity (e.g., an antibody) which comprises an antigen binding domain capable of specifically binding to a native conformation of a complex composed of the MHC class II and the GAD autoantigenic peptide.

In order to isolate high affinity entities (e.g., antibodies) which can specifically bind to MHC class II/GAD autoantigenic peptides having a native structural conformation, the isolated MHC/peptide complexes should be generated such that a correct folding of the MHC class II alpha and beta chains with the antigenic peptide occurs. It should be noted that for preparation of a recombinant complex of MHC class II and a restricted antigen peptide the extracellular domains of the alpha and beta chains are required.

When expressed in eukaryotic cells, the signal peptide of the MHC class II molecules is cleaved post translationally, thus obtaining a mature protein. To enable correct folding of the antigenic peptide within the MHC class II molecules, the antigenic peptide should be covalently attached close to the N-terminus of the extracellular domain of the mature MHC class II beta chain.

According to some embodiments of the invention, the structural conformation is obtainable or obtained when the GAD autoantigenic peptide is covalently conjugated or bound to the extracellular domain of the mature beta chain of the MHC class II.

According to some embodiments of the invention, the GAD autoantigenic peptide is covalently bound at a C terminus thereof to an N-terminus of an extracellular domain of the MHC class II.

As used herein the phrase "covalently bound" (or conjugated) refers to being part of the polypeptide chain of the mature beta chain. Such a covalent conjugation can be achieved by translationally fusing the coding sequence of the GAD autoantigenic peptide to the coding sequence of the extracellular domain of the beta chain MHC class II molecule.

According to some embodiments of the invention, the GAD autoantigenic peptide is covalently embedded between amino acids 1-6 of an extracellular domain of the beta chain of the MHC class II.

As used herein the phrase "covalently embedded between" refers to being covalently bound within an amino acid sequence (a polypeptide).

According to some embodiments of the invention, the GAD autoantigenic peptide is covalently embedded between amino acids 1-2, 2-3, 3-4, 4-5, or 5-6 of the extracellular domain of the beta chain of the MHC class II.

Thus, the GAD autoantigenic peptide can be embedded after the first, second, third, fourth or fifth amino acid position of the mature extracellular domain of the beta chain of the MHC class II.

According to some embodiments of the invention, the GAD autoantigenic peptide is covalently attached after the third amino acid of the mature MHC class II beta chain (i.e., between the third and fourth amino acids of the mature MHC class II beta chain).

According to some embodiments of the invention, the GAD autoantigenic peptide is flanked at a C-terminus thereof by a linker peptide.

The linker peptide can be selected according to the expression system used for preparing the recombinant MHC class II-antigenic peptide.

Usually, the linker peptide confers flexibility to the mature beta chain and enables the folding of the conjugated antigenic peptide within the peptide-binding grooves within the MHC class II molecules.

In some embodiments of the invention, the linker peptide comprises a site for an enzymatic cleavage of the recombinant protein. Cleavage can be done in vivo (i.e., within a living organism), ex vivo (when cell of an organism are cultured) or in vitro.

According to some embodiments of the invention, the linker peptide may include a thrombin cleavage site. For example, a linker peptide may comprise a thrombin cleavage site (e.g., the sequence LVPRGS) flanked by two sequences which increase flexibility of the recombinant protein such as GGGGS.

Following are non-limiting examples of linker peptides which can be covalently conjugated to the GAD autoantigenic peptide complexes:

(1) A linker peptide comprising the Glycine (G)-Serine (S) pair of amino acids being repeated between one to 30 times [GS]n (wherein n=1-30) (SEQ ID NO:23).

(2) A linker peptide comprising the GGGGS sequence being repeated between one to 6 times [GGGGS]n (wherein n=1-6) (SEQ ID NO:261);

(3) A linker peptide GGGSLVPRGSGGGGS (SEQ ID NO:25);

(4) A linker peptide GGGGSLVPRGSGGGGS (SEQ ID NO:26).

The linker peptide can be translationally fused to the GAD autoantigenic peptide and to the extracellular domain of the mature beta chain MHC class II. For example, the C-terminus of the GAD autoantigenic peptide is fused directly to the N-terminus of the linker peptide; and the C-terminus of the linker peptide is fused directly to the N-terminus or to an amino acid position between 1-6 of the N-terminal end of the mature beta chain extracellular domain.

In addition, in order to form a non-covalent complex between the alpha and beta chains of the MHC class II, each of the extracellular domains of the alpha and beta chains comprises a member of a binding pair, which upon interaction with the other member forms a binding pair.

Non-limiting examples of such binding pairs include the leucine-zipper dimerization domains of Jun-Fos binding pairs and the acidic (AZ) and basic (BZ) leucine zipper motives which form a stable protein complex.

According to some embodiments of the invention, the beta chain of the MHC class II comprises a first member of a binding pair which upon expression in eukaryotic cells binds to a second member of the binding pair, wherein the second member is comprised in an alpha chain of the MHC class II, wherein the beta chain and the alpha chain form the MHC class II.

For example, as described in the Examples section which follows, the MHC class II complex of some embodiments of the invention was generated by expressing in a host cell (e.g., S2 cells) a polynucleotide which comprises a nucleic acid sequence encoding a GAD autoantigenic peptide (e.g., GAD peptide) which is translationally fused to a nucleic acid sequence encoding an MHC class II beta chain (e.g., DR-B1*0401; SEQ ID NO:15) such that the encoded antigenic peptide is fused between the third and fourth amino acid positions of the beta chain (of the mature extracellular domain of the beta chain). As further shown in FIGS. 8A-B, the antigenic peptide is covalently fused to a linker peptide which is bound directly to the forth amino acid sequence of the mature extracellular domain of the beta chain.

The phrases "translationally fused" and "in frame" are interchangeably used herein to refer to polynucleotides which are covalently linked to form a single continuous open reading frame spanning the length of the coding sequences of the linked polynucleotides. Such polynucleotides can be covalently linked directly or preferably indirectly through a spacer or linker region.

According to an aspect of some embodiments of the invention, there is provided an isolated polynucleotide comprising a first nucleic acid sequence encoding an extracellular domain of an MHC class II beta chain [e.g., DR-B1*0401; SEQ ID NO:27 for the amino acid sequence; and SEQ ID NO: 28 for the nucleic acid sequence] and a second nucleic acid construct encoding a GAD autoantigenic peptide [e.g., GAD-peptide NFFRMVISNPAAT (SEQ ID NO: 22), AACTTCTTTCGTATGGTTATCAGCAATC-CAGCTGCGACT (SEQ ID NO:29) for the nucleic acid sequence encoding the GAD-peptide], wherein the second nucleic acid construct being translationally fused upstream of the first nucleic acid construct or between the nucleic acid sequence encoding amino acids 1-6 of the extracellular domain.

According to some embodiments of the invention, the second nucleic acid construct being translationally fused between the nucleic acid sequence encoding amino acids 3 and 4 of the extracellular domain.

According to some embodiments of the invention, the isolated polynucleotide further comprises a nucleic acid sequence encoding a linker peptide being translationally fused downstream of the second nucleic acid sequence.

According to some embodiments of the invention, the first nucleic acid sequence and the second nucleic acid sequence are connected via a nucleic acid sequence encoding a linker peptide (GGGSLVPRGSGGGGS; SEQ ID NO:63).

According to some embodiments of the invention, the isolated polynucleotide further comprises a third nucleic acid sequence encoding a first member of a binding pair [(e.g., Jun, the amino acid sequence set forth in SEQ ID NO:64 (RIARLEEKVKTLKAQNSELASTANML-REQVAQLKQKVMNH)] which upon expression in eukaryotic cells binds to a second member of the binding pair.

According to some embodiments of the invention, the third nucleic acid sequence encoding a first member of a binding pair is translationally fused downstream of the first nucleic acid sequence encoding an MHC class II beta chain.

According to some embodiments of the invention, the first member of binding pair (e.g., Jun amino acid sequence) is connected via a short peptide linker to the MHC class II beta chain. A non-limiting example of such a linker is set forth in SEQ ID NO:65 (VDGGGGG).

According to an aspect of some embodiments of the invention, there is provided a nucleic acid system comprising:

(i) a first polynucleotide comprising a first nucleic acid sequence encoding an MHC class II beta chain and a second nucleic acid construct encoding a GAD autoantigenic peptide, wherein the second nucleic acid construct being translationally fused upstream of the first nucleic acid construct; and a third nucleic acid sequence encoding a first member of a binding pair which upon expression in eukaryotic cells binds to a second member of the binding pair; and (ii) a second polynucleotide which comprises a forth nucleic acid sequence encoding an MHC class II alpha chain [e.g., DR-A1*0101; amino acids 1-217 of SEQ ID NO:10 (of the recombinant molecule); and nucleic acids 1-651 of SEQ ID NO:12].

According to some embodiments of the invention, the second polynucleotide further comprises a fifth nucleic acid sequence encoding the second member of the binding pair [e.g., Fos, the amino acid sequence set forth in SEQ ID NO:66 (LTDTLQAETDQLEDEKSALQTEIAN-LLKEKEKLEFILAAH)].

According to some embodiments of the invention, the fifth nucleic acid sequence encoding the second member of the binding pair is translationally fused downstream of the forth nucleic acid sequence encoding the MHC class II alpha chain.

According to some embodiments of the invention, the Fos amino acid sequence is connected via a short peptide linker to the MHC class II alpha chain. A non-limiting example of such a linker is set forth in SEQ ID NO:65 (VDGGGGG).

According to some embodiments of the invention, the fifth nucleic acid sequence encoding the second member of the binding pair and the forth nucleic acid sequence encoding an MHC class II alpha chain are connected via a nucleic acid sequence encoding a linker peptide (e.g., VDGGGGG; SEQ ID NO:65).

Non-limiting examples of recombinant beta chain and alpha chain molecules are illustrated in FIGS. 8A-B and 9A-B, and exemplary sequences thereof are provided in SEQ ID NOs: 9-10 and 11-12, respectively.

According to some embodiments of the invention, at least one molecule of the MHC class II complex (i.e., an alpha or beta chain) further comprises an in-frame tag, i.e., a nucleic acid sequence which encodes a peptide capable of being enzymatically modified to include a binding entity. For example, such a peptide can be used for site specific biotinylation using e.g., a biotin protein ligase-Bir A enzyme (AVIDITY). Non-limiting examples of such tags includes the Bir A recognition sequence is set forth by SEQ ID NO:67 (Leu Gly Gly Ile Phe Glu Ala Met Lys Met Glu Leu Arg Asp).

According to some embodiments of the invention, the Bir A recognition sequence for biotinylation is covalently conjugated at the carboxy terminal ($C^r$) of the recombinant alpha chain.

It should be noted that an in-frame tag can be used for isolation of antibodies which specifically bind to the specific MHC-peptide complex, such as using streptavidin.

According to some embodiments of the invention, the MHC class II-peptide complexes forms multimers which are bound by a common binding entity.

For example, multimers (e.g., tetramers) of MHC class II-peptide complexes can be formed using a streptavidin which binds to the biotinylated complexes.

According to an aspect of some embodiments of the invention, there is provided an isolated antibody comprising an antigen binding domain capable of specifically binding a complex composed of a major histocompatibility complex (MHC) class II and a GAD autoantigenic peptide, wherein the isolated antibody does not bind to the MHC class II in an absence of the GAD autoantigenic peptide, wherein the isolated antibody does not bind to the GAD autoantigenic peptide in an absence of the MHC class II.

According to an aspect of some embodiments of the invention, there is provided an isolated high affinity entity comprising an antigen binding domain capable of specifically binding a complex composed of a major histocompatibility complex (MHC) class II and a type I diabetes GAD autoantigenic peptide, wherein the isolated high affinity entity does not bind to the MHC class II in an absence of the GAD autoantigenic peptide, wherein the isolated high affinity entity does not bind to the GAD autoantigenic peptide in an absence of the MHC class II.

According to some embodiments of the invention, the antigen binding domain is capable of specifically binding to a native conformation of the complex composed of the MHC class II and the GAD autoantigenic peptide.

As used herein the phrase "native conformation" refers to the conformation of the complex when naturally presented on cells, e.g., cells of a mammal, e.g., human cells.

According to some embodiments of the invention, the native conformation comprises the structural conformation of the complex of the GAD autoantigenic peptide and the MHC class II when presented on an antigen presenting cell (APC).

Non-limiting examples of antigen presenting cells which display or present the complex of the MHC class II and the GAD autoantigenic peptide include macrophages, dendritic cells (DCs) and B-cells.

According to an aspect of some embodiments of the invention, there is provided an isolated high affinity entity comprising an antigen binding domain, the high affinity entity being isolatable by the isolated complex of some embodiments of the invention.

According to an aspect of some embodiments of the invention, there is provided an isolated high affinity entity comprising an antigen binding domain capable of specifically binding to the isolated complex of some embodiments of the invention.

According to some embodiments of the invention, the antigen binding domain of the isolated high affinity entity is capable of specifically binding to a native conformation of a complex composed of the MHC class II and the GAD autoantigenic peptide.

According to some embodiments of the invention, the antigen binding domain of the isolated high affinity entity is further capable of specifically binding to the isolated complex of some embodiments of the invention.

According to an aspect of some embodiments of the invention, there is provided an isolated high affinity entity comprising an antigen binding domain, the antigen binding domain being capable of specifically binding:

(i) a complex composed of a major histocompatibility complex (MHC) class II and a GAD autoantigenic peptide, wherein the isolated high affinity entity does not bind to the MHC class II in an absence of the GAD autoantigenic peptide, wherein the isolated high affinity entity does not bind to the GAD autoantigenic peptide in an absence of the MHC class II; and (ii) a native conformation of a complex composed of an MHC class II and a GAD autoantigenic peptide.

According to an aspect of some embodiments of the invention, there is provided an isolated high affinity entity comprising an antigen binding domain capable of specifically binding to an isolated complex comprising an MHC class II and a GAD autoantigenic peptide, wherein the GAD autoantigenic peptide being covalently conjugated to the amino terminal ($N^r$) end of a recombinant beta chain of the MHC class II.

According to an aspect of some embodiments of the invention, there is provided an isolated high affinity entity being isolatable by an isolated complex which comprises an MHC class II and a GAD autoantigenic peptide, wherein the GAD autoantigenic peptide being covalently conjugated at the amino terminal ($N^r$) end of a recombinant beta chain of the MHC class II, wherein an antigen binding domain of the isolated high affinity entity is capable of specifically binding to a native conformation of a complex composed of the MHC class II and the GAD autoantigenic peptide.

According to an aspect of some embodiments of the invention, there is provided an isolated high affinity entity being isolatable by an isolated complex which comprises an MHC class II and a GAD autoantigenic peptide, wherein the GAD autoantigenic peptide being covalently conjugated at the amino terminal ($N^r$) end of a recombinant beta chain of the MHC class II, wherein an antigen binding domain of the isolated high affinity entity is capable of specifically binding to:

(i) an isolated complex which comprises an MHC class II and a GAD autoantigenic peptide, wherein the GAD autoantigenic peptide being covalently conjugated at the amino terminal ($N^r$) end of a recombinant beta chain of the MHC class II; and (ii) a native conformation of a complex composed of the MHC class II and the GAD autoantigenic peptide.

According to an aspect of some embodiments of the invention, there is provided an isolated high affinity entity comprising a complementarity determining regions (CDRs) set forth by SEQ ID NOs: 43-45 and 37-39 (CDRs 1-3 of heavy chain and light chain of G3H8, respectively).

According to an aspect of some embodiments of the invention, there is provided an isolated high affinity entity comprising a complementarity determining regions (CDRs) set forth by SEQ ID NOs:55-57 and 49-51 (CDRs 1-3 of heavy chain and light chain of G1H12, respectively).

The phrase "high affinity entity" refers to any naturally occurring or artificially produced molecule, composition, or organism which binds to a specific antigen with a higher affinity than to a non-specific antigen.

It should be noted that the affinity can be quantified using known methods such as, surface plasmon resonance (SPR) (described in Scarano S, Mascini M, Turner A P, Minunni M. Surface plasmon resonance imaging for affinity-based biosensors. Biosens Bioelectron. 2010, 25: 957-66), and can be calculated using, e.g., a dissociation constant, Kd, such that a lower Kd reflects a higher affinity.

As described, the high affinity entity binds to a complex comprising an MHC class II and an MHC class II-restricted autoantigen (a GAD autoantigenic peptide).

According to some embodiments of the invention, the high affinity entity binds to a certain specific complex with a higher affinity as compared to the affinity of the same entity to a similar complex in which at least one of the complex components, i.e., the MHC class II alpha chain, the MHC class II beta chain, and/or the MHC class II-restricted autoantigen being replaced with a component having at least one mutation (substitution, deletion or insertion) with respect to the component of the specific complex.

According to some embodiments of the invention, the mutation is in an amino acid position which is conserved between restricted antigens of various MHC class II alleles.

According to some embodiments of the invention, the high affinity entity exhibits an affinity to a specific antigen which is higher in at least about one order of magnitude as compared to the affinity of the same entity to a non-specific antigen, e.g., at least about 2, at least about 3, at least about 4, at least about 5, at least about 6, at least about 7, at least about 8, at least about 9, at least about 10 orders of magnitudes higher.

According to some embodiments of the invention, the dissociation constant of the high affinity entity to the specific antigen is about $10^{-4}$ M or less, e.g., about $10^{-5}$ M or less, e.g., about $10^{-6}$ M or less, e.g., about $10^{-7}$ or less, e.g., about $10^{-8}$ or less, e.g., about $10^{-9}$ M or less, e.g., about $10^{-10}$ M or less.

Non-limiting examples of high affinity entities include an antibody, an antibody fragment, a phage displaying an antibody, a peptibody, a cell-based display entity (e.g., a bacterium or yeast displaying an antibody), and cell-free displaying entity (e.g., a ribosome displaying a peptide or antibody).

Bacteriophages which display antibodies and which can be used according to some embodiments of the invention include M13 and fd filamentous phage, T4, T7, and λ phages.

The techniques of using bacteria (e.g., *E. Coli*) and yeast for displaying antibodies are well (See e.g., Daugherty P S., et al., 1998. Antibody affinity maturation using bacterial surface display. Protein Engineering 11:825-832; Johan Rockberg et al., Epitope mapping of antibodies using bacterial surface display. Nature Methods 5, 1039-1045 (2008); Sachdev S Sidhu, Full-length antibodies on display, Nature Biotechnology 25, 537-538 (2007); each of which is fully incorporated herein by reference).

Cell-free displaying entities include a ribosome displaying a protein (described in Mingyue He and Michael J. Taussig, 2002. Ribosome display: Cell-free protein display technology. Briefings in functional genomics and proteomics. Vol 1: 204-212; Patrick Dufner et al., 2006. Harnessing phage and ribosome display for antibody optimization. Trends in Biotechnology, Vol. 24: 523-529; each of which is fully incorporated herein by reference).

Peptibodies are isolated polypeptide comprising at least one peptide capable of binding to an antigen (e.g., a CDR) attached to an Fc domain of an antibody (e.g., IgG, IgA, IgD, IgE, IgM antibodies) or a fragment of an Fc domain. A peptibody can include more than one peptide capable of binding an antigen (e.g., 2, 3, 4 or 5 peptides) which may be the same as one another or may be different from one another.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; (5) Single chain antibody ("SCA"), a genetically engineered molecule containing the variable region of the light chain and the variable region of the heavy chain, linked by a suitable polypeptide linker as a genetically fused single chain molecule; (6) CDR peptide is a peptide coding for a single complementarity-determining region (CDR); and (7) Single domain antibodies (also called nanobodies), a genetically engineered single monomeric antibody domain which selectively binds to a specific antigen. Nanobodies have a molecular weight of only 12-15 kDa, which is much smaller than a common antibody (150-160 kDa).

According to some embodiments of the invention, the antigen binding domain comprises complementarity determining region (CDR) selected from the group of the CDRs set forth by SEQ ID NOs: 43-45 and 37-39 (CDRs 1-3 of heavy chain and CDRs 1-3 of light chain of G3H8, respectively), and 55-57 and 49-51 (CDRs 1-3 of heavy chain and CDRs 1-3 of light chain of G1H12, respectively).

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

According to some embodiments of the invention, the antibodies are multivalent forms such as tetrameric Fabs, IgM or IgG1 antibodies, thus forming a multivalent composition with higher avidity to the target.

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including screening of phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

For in vivo use (for administering in a subject, e.g., human), the human or humanized antibody will generally tend to be better tolerated immunologically than one of non human origin since non variable portions of non human antibodies will tend to trigger xenogeneic immune responses more potent than the allogeneic immune responses triggered by human antibodies which will typically be allogeneic with the individual. It will be preferable to minimize such immune responses since these will tend to shorten the half-life, and hence the effectiveness, of the antibody in the individual. Furthermore, such immune responses may be pathogenic to the individual, for example by triggering harmful inflammatory reactions.

Alternately, an antibody of a human origin, or a humanized antibody, will also be advantageous for applications (such as targeted cell killing) in which a functional physiological effect, for example an immune response against a target cell, activated by a constant region of the antibody in the individual is desired. In these cases, an optimal functional interaction occurs when the functional portion of the antibody, such as the Fc region, and the molecule interacting therewith such as the Fc receptor or the Fc-binding complement component are of a similar origin (e.g., human origin).

Depending on the application and purpose, the antibody of the invention, which includes a constant region, or a portion thereof of any of various isotypes, may be employed. According to some embodiments of the invention, the isotype is selected so as to enable or inhibit a desired physiological effect, or to inhibit an undesired specific binding of the antibody via the constant region or portion thereof. For example, for inducing antibody-dependent cell mediated cytotoxicity (ADCC) by a natural killer (NK) cell, the isotype can be IgG; for inducing ADCC by a mast cell/basophil, the isotype can be IgE; and for inducing ADCC by an eosinophil, the isotype can be IgE or IgA. For inducing a complement cascade the antibody may comprise a constant region or portion thereof capable of initiating the cascade. For example, the antibody may advantageously comprise a Cgamma2 domain of IgG or Cmu3 domain of IgM to trigger a C1q-mediated complement cascade.

Conversely, for avoiding an immune response, such as the aforementioned one, or for avoiding a specific binding via the constant region or portion thereof, the antibody of the invention may not comprise a constant region (be devoid of a constant region), a portion thereof or specific glycosylation moieties (required for complement activation) of the relevant isotype.

According to an aspect of some embodiments of the invention, there is provided an isolated antibody comprising an antigen binding domain capable of specifically binding the isolated complex of MHC class II-GAD antigenic peptide of some embodiments of the invention. The isolated antibody does not bind to the MHC class II in an absence of the antigenic peptide, wherein the isolated antibody does not bind the antigenic peptide in an absence of the MHC class II.

According to some embodiments of the invention the antibody of some embodiments of the invention binds to the target complex (MHC class II-GAD autoantigen) with an affinity characterized by a dissociation constant which is lower than about 100 nanomolar, e.g., lower than about 50 nanomolar, e.g., lower than about 20 nanomolar, e.g., about 10 nanomolar or lower.

Once the CDRs of an antibody are identified, using conventional genetic engineering techniques, expressible polynucleotides encoding any of the forms or fragments of antibodies described herein can be synthesized and modified in one of many ways in order to produce a spectrum of related-products.

For example, to generate the high affinity entity of the invention (e.g., the antibody of the invention), an isolated polynucleotide sequence [e.g., SEQ ID NOs:40 (CDR1 of the G3H8 Ab light chain), 41 (CDR2 of the G3H8 Ab light chain), 42 (CDR3 of the G3H8 Ab light chain), 46 (CDR1 of the G3H8 Ab heavy chain), 47 (CDR2 of the G3H8 Ab heavy chain), 48 (CDR3 of the G3H8 Ab heavy chain), 2 (nucleic acid sequence encoding the G3H8 Ab light chain, FIG. 6B) or 4 (nucleic acid sequence encoding the G3H8 Ab heavy chain, FIG. 6D] encoding the amino acid sequence of the antibody of the invention [e.g., SEQ ID NOs:37 (CDR1 of the G3H8 Ab light chain), 38 (CDR2 of the G3H8 Ab light chain), 39 (CDR3 of the G3H8 Ab light chain), 43 (CDR1 of the G3H8 Ab heavy chain), 44 (CDR2 of the G3H8 Ab heavy chain), 45 (CDR3 of the G3H8 Ab heavy chain), 1 (amino acid sequence of the G3H8 Ab light chain, FIG. 6A) or 3 (amino acid sequence of the G3H8 Ab heavy chain, FIG. 6C)] is preferably ligated into a nucleic acid construct (expression vector) suitable for expression in a host cell. Such a nucleic acid construct includes a promoter sequence for directing transcription of the polynucleotide sequence in the cell in a constitutive or inducible manner.

The nucleic acid construct of the invention may also include an enhancer, a transcription and translation initiation sequence, transcription and translation terminator and a polyadenylation signal, a 5' LTR, a tRNA binding site, a packaging signal, an origin of second-strand DNA synthesis, and a 3' LTR or a portion thereof; a signal sequence for secretion of the antibody polypeptide from a host cell; additional polynucleotide sequences that allow, for example, the translation of several proteins from a single mRNA such as an internal ribosome entry site (IRES) and sequences for genomic integration of the promoter-chimeric polypeptide; sequences engineered to enhance stability, production, purification, yield or toxicity of the expressed peptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMT010/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Various methods can be used to introduce the nucleic acid construct of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Recombinant viral vectors are useful for in vivo expression since they offer advantages such as lateral infection and targeting specificity. Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses.

As mentioned hereinabove, a variety of prokaryotic or eukaryotic cells can be used as host-expression systems to express the antibody of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the antibody of the invention.

Recovery of the recombinant antibody polypeptide is effected following an appropriate time in culture. The phrase "recovering the recombinant polypeptide" refers to collecting the whole fermentation medium containing the polypeptide and need not imply additional steps of separation or purification. Notwithstanding the above, antibody polypeptides of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

According to an aspect of some embodiments of the invention, there is provided a molecule comprising the high affinity entity (e.g., the antibody) of the invention being conjugated to a functional moiety (also referred to as an "immunoconjugate") such as a detectable or a therapeutic moiety. The immunoconjugate molecule can be an isolated molecule such as a soluble or synthetic molecule.

Various types of detectable or reporter moieties may be conjugated to the high affinity entity of the invention (e.g., the antibody of the invention). These include, but are not limited to, a radioactive isotope (such as $^{125}$iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomography (PET) or Magnetic Resonance Imaging (MRI).

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.]. Fluorescence detection methods which can be used to detect the high affinity entity (e.g., antibody) when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the high affinity entity (e.g., the antibody) of some embodiments of the invention [e.g., horseradish peroxidase (HPR), beta-galactosidase, and alkaline phosphatase (AP)] and detection of enzyme-conjugated antibodies can be performed using ELISA (e.g., in solution), enzyme-linked immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. J Immunoassay 20:151-83; Wisdom G B., 1994. Methods Mol. Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

The affinity tag (or a member of a binding pair) can be an antigen identifiable by a corresponding antibody [e.g., digoxigenin (DIG) which is identified by an anti-DIG antibody) or a molecule having a high affinity towards the tag [e.g., streptavidin and biotin]. The antibody or the molecule which binds the affinity tag can be fluorescently labeled or conjugated to enzyme as described above.

Various methods, widely practiced in the art, may be employed to attach a streptavidin or biotin molecule to the antibody of the invention. For example, a biotin molecule may be attached to the antibody of the invention via the recognition sequence of a biotin protein ligase (e.g., BirA) as described in the Examples section which follows and in Denkberg, G. et al., 2000. Eur. J. Immunol. 30:3522-3532. Alternatively, a streptavidin molecule may be attached to an antibody fragment, such as a single chain Fv, essentially as described in Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996. Protein Engineering 9:203; Pearce L A. et al., 1997. Biochem Molec Biol Intl 42:1179-1188).

Functional moieties, such as fluorophores, conjugated to streptavidin are commercially available from essentially all major suppliers of immunofluorescence flow cytometry reagents (for example, Pharmingen or Becton-Dickinson).

According to some embodiments of the invention, biotin conjugated antibodies are bound to a streptavidin molecule to form a multivalent composition (e.g., a dimer or tetramer form of the antibody).

Table 1 provides non-limiting examples of identifiable moieties which can be conjugated to the antibody of the invention.

TABLE 1

| Identifiable Moiety | Amino Acid sequence (GenBank Accession No.)/ SEQ ID NO: | Nucleic Acid sequence (GenBank Accession No.)/ SEQ ID NO: |
|---|---|---|
| Green Fluorescent protein | AAL33912/68 | AF435427/69 |
| Alkaline phosphatase | AAK73766/70 | AY042185/71 |
| Peroxidase | CAA00083/72 | A00740/73 |
| Histidine tag | Amino acids 264-269 of GenBank Accession No. AAK09208/74 | Nucleotides 790-807 of GenBank Accession No. AF329457/75 |
| Myc tag | Amino acids 273-283 of GenBank Accession No. AAK09208/74 | Nucleotides 817-849 of GenBank Accession No. AF329457/75 |
| Biotin lygase tag | LHHILDAQKMVWNHR/102 | |
| orange fluorescent protein | AAL33917/78 | AF435432/79 |
| Beta galactosidase | ACH42114/80 | EU626139/81 |
| Streptavidin | AAM49066/82 | AF283893/83 |

Table 1.

As mentioned, the high affinity entity (e.g., the antibody) may be conjugated to a therapeutic moiety. The therapeutic moiety can be, for example, a cytotoxic moiety, a toxic moiety, a cytokine moiety and a second antibody moiety comprising a different specificity to the antibodies of the invention.

Non-limiting examples of therapeutic moieties which can be conjugated to the high affinity entity (e.g., the antibody) of the invention are provided in Table 2, hereinbelow.

TABLE 2

| Therapeutic moiety | Amino acid sequence (GenBank Accession No.)/SEQ ID NO: | Nucleic acid sequence (GenBank Accession No.)/SEQ ID NO: |
|---|---|---|
| Pseudomonas exotoxin | ABU63124/84 | EU090068/85 |
| Diphtheria toxin | AAV70486/86 | AY820132.1/87 |
| interleukin 2 | CAA00227/88 | A02159/89 |
| CD3 | P07766/90 | X03884/91 |
| CD16 | NP_000560.5/92 | NM_000569.6/93 |
| interleukin 4 | NP_000580.1/94 | NM_000589.2/95 |
| HLA-A2 | P01892/96 | K02883/97 |
| interleukin 10 | P22301/98 | M57627/99 |
| Ricin toxin | EEF27734/100 | EQ975183/101 |

According to some embodiments of the invention, the toxic moiety is PE38 KDEL [(SEQ ID NO:76 for protein) and SEQ ID NO:77 for nucleic acid).

The functional moiety (the detectable or therapeutic moiety of the invention) may be attached or conjugated to the high affinity entity (e.g., the antibody) of the invention in various ways, depending on the context, application and purpose.

When the functional moiety is a polypeptide, the immunoconjugate may be produced by recombinant means. For example, the nucleic acid sequence encoding a toxin (e.g., PE38 KDEL) or a fluorescent protein [e.g., green fluorescent protein (GFP), red fluorescent protein (RFP) or yellow fluorescent protein (YFP)] may be ligated in-frame with the nucleic acid sequence encoding the high affinity entity (e.g., the antibody) of the invention and be expressed in a host cell to produce a recombinant conjugated antibody. Alternatively, the functional moiety may be chemically synthesized by, for example, the stepwise addition of one or more amino acid residues in defined order such as solid phase peptide synthetic techniques.

A functional moiety may also be attached to the high affinity entity (e.g., the antibody) of the invention using standard chemical synthesis techniques widely practiced in the art [see e.g., hypertexttransferprotocol://worldwideweb (dot) chemistry (dot) org/portal/Chemistry)], such as using any suitable chemical linkage, direct or indirect, as via a peptide bond (when the functional moiety is a polypeptide), or via covalent bonding to an intervening linker element, such as a linker peptide or other chemical moiety, such as an organic polymer. Chimeric peptides may be linked via bonding at the carboxy (C) or amino (N) termini of the peptides, or via bonding to internal chemical groups such as straight, branched or cyclic side chains, internal carbon or nitrogen atoms, and the like. Description of fluorescent labeling of antibodies is provided in details in U.S. Pat. Nos. 3,940,475, 4,289,747, and 4,376,110.

Exemplary methods for conjugating peptide moieties (therapeutic or detectable moieties) to the high affinity entity (e.g., the antibody) of the invention are described herein below:

SPDP Conjugation

A non-limiting example of a method of SPDP conjugation is described in Cumber et al. (1985, Methods of Enzymology 112: 207-224). Briefly, a peptide, such as a detectable or therapeutic moiety (e.g., 1.7 mg/ml) is mixed with a 10-fold excess of SPDP (50 mM in ethanol); the antibody is mixed with a 25-fold excess of SPDP in 20 mM sodium phosphate, 0.10 M NaCl pH 7.2 and each of the reactions is incubated for about 3 hours at room temperature. The reactions are then dialyzed against PBS. The peptide is reduced, e.g., with 50 mM DTT for 1 hour at room temperature. The reduced peptide is desalted by equilibration on G-25 column (up to 5% sample/column volume) with 50 mM $KH_2PO_4$ pH 6.5. The reduced peptide is combined with the SPDP-antibody in a molar ratio of 1:10 antibody:peptide and incubated at 4° C. overnight to form a peptide-antibody conjugate.

Glutaraldehyde Conjugation

A non-limiting example of a method of glutaraldehyde conjugation is described in G. T. Hermanson (1996, "Antibody Modification and Conjugation, in Bioconjugate Techniques, Academic Press, San Diego). Briefly, the antibody and the peptide (1.1 mg/ml) are mixed at a 10-fold excess with 0.05% glutaraldehyde in 0.1 M phosphate, 0.15 M NaCl pH 6.8, and allowed to react for 2 hours at room temperature. 0.01 M lysine can be added to block excess sites. After the reaction, the excess glutaraldehyde is removed using a G-25 column equilibrated with PBS (10% v/v sample/column volumes)

Carbodiimide Conjugation

Conjugation of a peptide with an antibody can be accomplished using a dehydrating agent such as a carbodiimide, e.g., in the presence of 4-dimethyl aminopyridine. Carbodiimide conjugation can be used to form a covalent bond between a carboxyl group of peptide and an hydroxyl group of an antibody (resulting in the formation of an ester bond), or an amino group of an antibody (resulting in the formation of an amide bond) or a sulfhydryl group of an antibody (resulting in the formation of a thioester bond). Likewise, carbodiimide coupling can be used to form analogous covalent bonds between a carbon group of an antibody and an hydroxyl, amino or sulfhydryl group of the peptide [see, J. March, *Advanced Organic Chemistry: Reaction's, Mechanism, and Structure, pp.* 349-50 & 372-74 (3d ed.), 1985]. For example, the peptide can be conjugated to an antibody via a covalent bond using a carbodiimide, such as dicyclohexylcarbodiimide [B. Neises et al. (1978), Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561)].

As mentioned above and further illustrated in the Examples section which follows, the isolated high affinity entity (e.g., the antibody) according to some embodiments of the invention can be used to detect the complex of MHC class II and a diabetes associate autoantigen (e.g., the GAD autoantigenic peptide) on the surface antigen presenting cells (APC) such as dendritic cells, macrophages and B-cells.

Thus, according to an aspect of some embodiments of the invention, there is provided a method of detecting presentation of a GAD autoantigenic peptide on a cell. The method is effected by contacting the cell with the high affinity entity of some embodiments of the invention, the molecule of some embodiments of the invention, or the antibody of some embodiments of the invention, under conditions which allow immunocomplex formation, wherein a presence or a level above a predetermined threshold of the immunocomplex is indicative of presentation of the diabetes-associated autoantigenic peptide on the cell.

The cell presenting the GAD autoantigenic peptide (e.g., GAD antigen) can be any nucleated cell such as an antigen presenting cell (APC) in the blood, pancreas and lymphoid organs such as thymus, bone marrow, lymph node and lymphoid follicles.

Contacting the cell with the high affinity entity (e.g., the antibody)/molecule or multivalent composition of the invention may be effected in vitro (e.g., in a cell line), ex vivo or in vivo.

As mentioned, the method of the invention is effected under conditions sufficient to form an immunocomplex; such conditions (e.g., appropriate concentrations, buffers, temperatures, reaction times) as well as methods to optimize such conditions are known to those skilled in the art, and examples are disclosed herein.

As used herein the phrase "immunocomplex" refers to a complex which comprises the high affinity entity of some embodiments of the invention (e.g., the antibody) and the MHC-class II-GAD autoantigenic peptide (e.g., GAD peptide).

Determining a presence or level of the immunocomplex of the invention is performed using the detectable moiety to which the high affinity entity (e.g., antibody) is attached, and can be performed using various methods are known in the art and described hereinabove.

The level of the immunocomplex in the tested cell (e.g., a cell of a subject in need thereof) is compared to a predetermined threshold. The threshold may be determined based on a known reference level and/or a level in a control cell. The control cell can be obtained from a control, healthy subject (e.g., a subject not diagnosed with diabetes or not being at-risk for diabetes, or from a subject devoid of the specific MHC molecule forming the MHC-peptide complex (e.g., DR4). According to some embodiments of the invention, the control subject is of the same species e.g. human, preferably matched with the same age, weight, sex etc. as the subject in need thereof.

Thus, the teachings of the invention can be used to detect cells which present GAD autoantigenic peptideic peptides (e.g., GAD presenting cell(s)) in a biological sample of the subject.

As used herein the phrase "cells which present GAD autoantigenic peptides" refers to any cell or a portion thereof of the subject which displays the complex of MHC class II and MHC-restricted GAD autoantigenic peptide.

The biological sample can be any sample which contains cells or a portion thereof (e.g., cell debris, membrane vesicles) which putatively present the MHC class II-GAD autoantigenic peptide complex.

According to some embodiments of the invention, the subject is at risk of developing type 1 diabetes. Non-limiting examples of subjects who are at risk to develop type 1 diabetes include subjects carrying the HLA DRB1*03,*04; DQB1*0302 genotype and the DR3-DQ2 and DR4-DQ8 haplotypes.

Type 1 diabetes results from autoimmune destruction of insulin-producing beta cells of the pancreas, which lead to lack of insulin and subsequently increased blood and urine glucose. Classical symptoms include polyuria (frequent urination), polydipsia (increased thirst), polyphagia (increased hunger), and weight loss.

To date, the diagnosis of type 1 diabetes is made by demonstrating any one of the following: Fasting plasma glucose level at or above 7.0 mmol/L (126 mg/dL); Plasma glucose at or above 11.1 mmol/L (200 mg/dL) two hours after a 75 g oral glucose load as in a glucose tolerance test; Symptoms of hyperglycemia and casual plasma glucose at or above 11.1 mmol/L (200 mg/dL); Glycated hemoglobin (hemoglobin A1C) at or above 6.5. Thus, in most cases, when type 1 diabetes is diagnosed most of the beta cells in the pancreas are destroyed.

Early signs of type 1 diabetes include the development of islets autoantibodies. Autoantibodies to four islet antigen groups have so far been identified: insulin or proinsulin, GAD65 or GAD67, IA-2 (PHOGRIN), and ZnT8. The number of islets autoantibodies, greater titer, affinity, and broadness of epitope reactivity are features of—autoantibodies that affect the risk for T1D. Combination of family history information, genetic factors, autoantibodies, age and beta cells function markers provides a disease risk determination that can be calculated empirically.

As shown in Example 4 of the Examples section, the isolated antibodies of some embodiments of the invention were shown capable of detecting APC (which present the MHC class II-GAD antigenic peptide) in the infiltrated islets of diabetic B7/DR4 mice. Moreover, the isolated antibodies of some embodiments of the invention were shown capable of detecting APC in the infiltrated islets of pre-diabetic young B7/DR4 mice, thus diagnosing early signs of beta cell destruction leading to type 1 diabetes.

Using the currently available diagnostic tools, at the time a diagnosis of type I diabetes is made in a subject about 90% of the insulin producing cells are destroyed (Gepts W. Pathologic anatomy of pancreas in juvenile diabetes mellitus. Diabetes 1965; 14: 619-633).

It should be noted that diagnosing type 1 diabetes at the early stages of the disease is of significant importance since not all of the beta cells in the pancreas are destroyed. Thus, early detection of type 1 diabetes, before a complete diagnosis is made, is of great significance, since it enables clinical intervention and treatment which will prevent the complete destruction of beta cells.

Antigen-specific tolerance approaches are desirable treatment of T1D. The focus of these developing treatment strategies is to safely inactivate pathogenic autoreactive T cells in an autoantigen-specific manner while leaving the remainder of immune system unperturbed. Identification of the antigen-specificity nature of the immune response prior to antigen-specific intervention will allow the adjustment of the suitable treatment for the current auto-immune response of the subject. The isolated antibodies of some embodiments of the invention were shown capable of detecting specific auto-antigens presentation, and therefore identifying the specific-antigenic nature of the auto-immune process. Thus, the teachings of the invention can be used to select an accurate and most suitable antigen-specific intervention strategy.

Thus, according to an aspect of some embodiments of the invention, there is provided a method of diagnosing type 1 diabetes (T1D) in a subject. The method is effected by contacting a cell of the subject with the high affinity entity (e.g., antibody) of some embodiments of the invention, the molecule of some embodiments of the invention, or the multivalent antibody of some embodiments of the invention under conditions which allow immunocomplex formation, wherein a presence or a level above a pre-determined threshold of the immunocomplex in the cell is indicative of the type 1 diabetes in the subject.

As used herein the term "diagnosing" refers to determining presence or absence of a pathology, classifying a pathology or a symptom, determining a severity of the pathology, monitoring pathology progression, forecasting an outcome of a pathology and/or prospects of recovery.

According to some embodiments of the invention, diagnosis of type 1 diabetes relates to detecting early signs of the disease, even before the destruction of beta cells has began and the beta cells are still functional (i.e., produce insulin in response to elevation in glucose levels).

To facilitate diagnosis, the above teachings can be combined with other methods of diagnosing type 1 diabetes which are well known in the art.

Since as shown by the present inventors presentation of the MHC class II-GAD antigenic peptide complex by APCs (dendritic cells, macrophages etc.) in the infiltrated islets begins at early stages of the disease, antibodies which specifically bind to cells presenting the complex of MHC class II and a GAD autoantigenic peptide can be used to treat type 1 diabetes.

Thus, according to an aspect of some embodiments of the invention, there is provided a method of treating type 1 diabetes (T1D), comprising administering to a subject in need thereof a therapeutically effective amount of the isolated high affinity entity (e.g., antibody) of some embodiments of the invention, the molecule of some embodiments of the invention (e.g., which includes the high affinity entity conjugated to a therapeutic moiety such as toxin), the multivalent composition comprising same of some embodiments of the invention, the isolated polynucleotide or the nucleic acid construct encoding same, thereby treating the treating type 1 diabetes (T1D).

The term "treating" refers to inhibiting or arresting the development of a disease, disorder or condition and/or causing the reduction, remission, or regression of a disease, disorder or condition. Those of skill in the art will understand that various methodologies and assays can be used to assess the development of a disease, disorder or condition, and similarly, various methodologies and assays may be used to assess the reduction, remission or regression of a disease, disorder or condition.

According to some embodiments of the invention, treatment of type 1 diabetes is achieved by blocking presentation of the MHC class II/GAD autoantigenic peptide on APCs, and thus preventing or avoiding recognition of the antigen presenting cells by the specific T cells.

It should be noted that by blocking the presentation of the MHC class II-antigenic peptide complex by APCs, the inflammatory process and reactions that are induced by these APCs are also blocked, thereby reducing and eliminating the destruction of the beta cells in the islets that produce insulin.

According to some embodiments of the invention, treatment with the isolated antibodies of the invention is performed at an early stage of disease, before the onset of diabetic symptoms.

According to some embodiments of the invention, treatment with the isolated high affinity entity (e.g., the antibody) of some embodiments of the invention prevents the symptoms of glucose blood level increase and the subsequent need for insulin administration (e.g., by injections) because the beta cell own insulin production is spared.

According to some embodiments of the invention, for the inhibition approach, i.e., inhibition of MHC class II-type I diabetes-associate autoantigen presentation on APC (e.g., MHC class II-GAD antigen presentation on APCs) the effector functions of the high affinity entity (e.g., antibody) are manipulated such that the high affinity entity (e.g., antibody) is devoid of an Antibody-Dependent Cell-Mediated Cytotoxicity (ADCC) activity or devoid of a Complement-Dependent Cytotoxicity (CDC) activity. For example, the antibody of some embodiments of the invention is devoid of a constant region, a portion thereof or specific glycosylation moieties (required for complement activation) of the relevant isotype.

Additionally or alternatively, the high affinity entity (e.g., antibody) of the invention can be used to directly kill the APCs which display the GAD autoantigenic peptide in a complex with the MHC class II.

According to some embodiments of the invention, for the killing approach (i.e., killing of APCs which present the complex of MHC class II and GAD autoantigenic peptide), the isolated high affinity entity (e.g., antibody) is a naked high affinity entity that is capable of mediating ADCC or CDC.

As used herein the term "naked" refers to being devoid of a conjugated moiety such as a detectable or a therapeutic moiety.

According to some embodiments of the naked antibody comprises the constant region, a portion thereof or specific glycosylation moieties which mediate ADCC or CDC.

According to some embodiments of the invention, for the killing approach (i.e., killing of APCs which present the MHC class II-GAD autoantigenic peptide, the isolated high affinity entity (e.g., the antibody) is conjugated to a therapeutic moiety (e.g., drug, toxic moiety) that will kill the APCs presenting the MHC class II-GAD antigenic complex.

According to some embodiments of the invention, for the drug is an anti-inflammatory drugs or a cytokine that will reduce or inhibit the local inflammation in the islets and thus will rescue and inhibit the damage to the insulin producing beta cells.

According to some embodiments of the invention, the isolated high affinity entity (e.g., the antibody), molecule comprising same, multivalent antibody composition, polynucleotide, and/or nucleic acid construct of the invention is capable of killing MHC class II-GAD autoantigenic peptides (e.g., GAD) presenting cells in the subject in need thereof.

The high affinity entity (e.g., the antibody) of the invention, the molecule of the invention (which comprise the high affinity entity, e.g., antibody, conjugated to a therapeutic or detectable moiety), the multivalent composition of the invention, the isolated polynucleotide or the nucleic acid construct of the invention may be provided per se or may be administered as a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the high affinity entity (e.g., the antibody) of the invention, the molecule of the invention (which comprise the high affinity entity, e.g., an antibody, conjugated to a therapeutic or detectable moiety, or a polynucleotide encoding same), the multivalent composition of the invention, the isolated polynucleotide or the nucleic acid construct of the invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the invention may also be formulated in rectal compositions such as suppositories or retention enemas, using, e.g., conventional suppository bases such as cocoa butter or other glycerides.

Pharmaceutical compositions suitable for use in context of the invention include compositions wherein the active ingredients are contained in an amount effective to achieve the intended purpose. More specifically, a therapeutically effective amount means an amount of active ingredients [e.g., the high affinity entity of the invention, e.g., the antibody of the invention, the molecule of the invention (e.g., which comprise the antibody conjugated to a therapeutic or detectable moiety), the multivalent composition of the invention, the isolated polynucleotide or the nucleic acid construct of the invention] effective to prevent, alleviate or ameliorate symptoms of a disorder (type 1 diabetes) or prolong the survival of the subject being treated.

Determination of a therapeutically effective amount is well within the capability of those skilled in the art, especially in light of the detailed disclosure provided herein.

For example, the effect of the active ingredients (e.g., the high affinity entity, e.g., the antibody of the invention, or the polynucleotide encoding same) on type 1 diabetes treatment can be evaluated by monitoring the level of glucose in the blood of the treated subject, and/or measuring the level of hemoglobin A1c using well known methods.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

According to some embodiments of the invention, the therapeutic agent of the invention (e.g., the high affinity entity of the invention, e.g., the antibody, molecule and/or multivalent composition of the invention) can be provided to the subject in combination with other drug(s) designed for treating type 1 diabetes (combination therapy). Non-limiting examples of such drugs include insulin (e.g., a recombinant human insulin, pig derived insulin) and Anti-CD3 mAb. Methods of administering insulin including injection, insulin pumps and inhaled insulin have been available at various times. Pancreas transplants have been also used to treat type 1 diabetes. The combination therapy may increase the therapeutic effect of the agent of the invention in the treated subject.

Compositions of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The agents of some embodiments of the invention which are described hereinabove for detecting the complexes of MHC class II/GAD autoantigenic peptides (e.g., GAD antigenic peptide) (either in an isolated form or when displayed on cells) may be included in a diagnostic kit/article of manufacture preferably along with appropriate instructions for use and labels indicating FDA approval for use in diagnosing, determining predisposition to, and/or assessing type 1 diabetes.

Such a kit can include, for example, at least one container including at least one of the above described diagnostic agents (e.g., the high affinity entity, e.g., the antibody) and an imaging reagent packed in another container (e.g., enzymes, secondary antibodies, buffers, chromogenic substrates, fluorogenic material). The kit may also include appropriate buffers and preservatives for improving the shelf-life of the kit.

According to an aspect of some embodiments of the invention, there is provided a method of isolating a high affinity entity which specifically binds to a complex composed of a major histocompatibility complex (MHC) class II and a GAD autoantigenic peptide, comprising:

(a) screening a library comprising a plurality of high affinity entities with the isolated complex of some embodiments of the invention; and (b) isolating at least one high affinity entity which specifically binds to the isolated complex of some embodiments of the invention and not to the MHC class II in the absence of the GAD autoantigenic peptide or to the GAD autoantigenic peptide in an absence of the MHC class II, thereby isolating the high affinity entities which specifically bind to the complex of the MHC class II and the GAD autoantigenic peptide.

According to some embodiments of the invention, the high affinity entity further specifically binds to a native conformation of the complex of the MHC class II and the GAD autoantigenic peptide.

According to an aspect of some embodiments of the invention there is provided a composition of matter comprising the isolated MHC class II and GAD autoantigenic peptide complex of some embodiments of the invention and a conjugated functional moiety.

The conjugated functional moiety can be a therapeutic or a detectable moiety as described above. Conjugation of the functional moiety can be performed as described above and/or in U.S. Patent Application No. 20030166277 which is fully incorporated herein by reference.

According to some embodiments of the invention, the functional moiety comprises an antibody or a fragment specific for a cell surface marker. The cell surface marker can be expressed on an antigen presenting cell.

Examples of cell surface markers include, but are not limited to cell surface markers of tumor cells, epithelial cells, fibroblast, and T cells (e.g., CD28, CTLA-4 and CD25).

According to some embodiments of the invention, the functional moiety comprises a therapeutic moiety such as a cytokine or lymphokine. The cytokine or lymphokine may be linked to the MHC class II and GAD autoantigenic peptide complex either directly or via, e.g., formation of a multivalent compound (using streptavidin or avidin for example, and a biotinylated cytokine or lymphokine.

Non-limiting examples of cytokines or lymphokines include interleukins (e.g., IL-2, IL-3, IL-4, IL-5, IL-6, IL-10, IL-12, IL-15, and IL-18), alpha interferons (e.g., IFN.alpha.), beta interferons (e.g., IFN.beta.), gamma interferons (e.g., IFN.gamma.), granulocyte-macrophage colony stimulating factor (GM-CSF), and transforming growth factor (TGF, e.g., TGF-alpha. and TGF-beta).

According to an aspect of some embodiments of the invention there is provided a pharmaceutical composition comprising the composition of matter of some embodiments of the invention and a therapeutically acceptable carrier as described above.

The composition of matter of some embodiments of the invention (e.g., which comprise the MHC class II/peptide complex conjugated to the functional moiety) is useful for modulating, i.e., either inhibiting or stimulating, an immune response; for stimulating desirable immune responses, for example, immune responses against infectious agents or cancer; for inhibiting undesirable immune responses, such as allergic responses, allograft rejections, and autoimmune diseases; by directing the MHC class II/GAD autoantigenic peptide complex to professional antigen presenting cells, such as dendritic cells, B cells, or macrophages; tumor cells; epithelial cells; fibroblasts; T cells; or other cells. Depending on the targeted cell type, this will lead to either very efficient stimulation or inhibition of antigen specific T cell activity.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Production of DR4 Molecules in S2 Cells

DES TOPO DR-A1*0101/DR-B1*0401(HA-307-319) plasmids for inducible expression in Schneider S2 cell were used for cloning of DR-B1*0401(GAD$_{555-567}$) construct, transfection and expression of recombinant four-domain MHC class II as previously reported (Svendsen, P., et al., 2004). Briefly, in these constructs the intracellular domains of the DR-A and DR-B chains were replaced by leucine-zipper dimerization domains of Fos and Jun transcription factors, respectively, for heterodimer assembly. The antigenic peptide was introduced to the N-terminus of the DR-B chain through a flexible linker. Bir A recognition sequence for biotinylation was introduced to the C-terminus of the DR-A chain. DR-A and DR-B plasmids were co-transfected with pCoBlast selection vector to S2 cells using cellfectin reagent (invitrogen). Stable single-cell line clones were verified for protein expression. Upon induction with $CuSO_4$, cells supernatant were collected and DR4 complexes were affinity purified by anti-DR LB3.1 (ATCC number HB-298) monoclonal antibody (mAb). The purified DR4 complexes were biotinylated by Bir-A ligase (Avidity) and characterized by SDS-PAGE. The right folding of the complexes was verified by recognition of anti-DR conformation sensitive mAb (L243) in ELISA binding assay.

Selection of Phage Abs on Biotinylated Complexes

Selection of phage Abs on biotinylated complexes was performed as described (Cohen C J et al., 2003, J Mol Recognit. 2003, 16: 324-32). Briefly, a large human Fab library containing $3.7 \times 10^{10}$ different Fab clones was used for the selection (de Haard H. J., et al., 1999). Phages were first preincubated with streptavidin-coated paramagnetic beads (200 µl; Dynal) to deplete the streptavidin binders. The remaining phages were subsequently used for panning with decreasing amounts of biotinylated MHC-peptide complexes. The streptavidin-depleted library was incubated in solution with soluble biotinylated DR4/GAD (500 nM for the first round, and 100 nM for the following rounds) for 30 minutes at room temperature. Streptavidin-coated magnetic beads (200 µl for the first round of selection and 100 µl for the following rounds) were added to the mixture and incubated for 10-15 minutes at room temperature. The beads were washed extensively 12 times with PBS/0.1% Tween 20 and an additional two washes were with PBS. Bound phages were eluted with triethylamine (100 mM, 5 minutes at room temperature), followed by neutralization with Tris-HCl (1 M, pH 7.4), and used to infect E. coli TG1 cells (OD=0.5) for 30 minutes at 37° C. The diversity of the selected Abs was determined by DNA fingerprinting using a restriction endonuclease (BstNI), which is a frequent cutter of Ab V gene sequences.

Expression and Purification of Soluble Recombinant Fab Abs

TG1 or BL21 cells were grown to $OD_{600}$=0.8-1.0 and induced to express the recombinant Fab Ab by the addition of IPTG for 3-4 hours at 30° C. Periplasmic content was released using the B-PER solution (Pierce), which was applied onto a prewashed TALON column (Clontech). Bound Fabs were eluted using 0.5 ml of 100 mM in PBS. The eluted Fabs were dialyzed twice against PBS (overnight, 4° C.) to remove residual imidazole.

ELISA with Purified Fab Antibodies

Binding specificity of individual soluble Fab fragments were determined by ELISA using biotinylated MHC/peptide complexes. ELISA plates (Falcon) were coated overnight with BSA-biotin (1 μg/well). After being washed, the plates were incubated (1 hour at room temperature) with streptavidin (10 μg/ml), washed extensively, and further incubated (1 hour at room temperature) with 5 μg/ml of MHC/peptide complexes. The plates were blocked for 30 minutes at room temperature with PBS/2% skim milk and subsequently were incubated for 1 hour at room temperature with 5 μg/ml soluble purified Fab. After washing, plates were incubated with horseradish peroxidase-conjugated/anti-human-Fab antibody. Detection was performed using TMB reagent (Sigma).

Flow Cytometry

DR4—EBV-transformed B lymphoblast Preisscells were incubated overnight with medium containing 70 μM with $GAD_{555-567}$ (NFFRMVISNPAAT; SEQ ID NO:22) or control peptide: $GAD_{552-572}$ (SEQ ID NO:13), $HA_{307-319}$ (PKYVKQNTLKLAT; SEQ ID NO:30), $InsA_{1-15}$ (GIVEQCCTSICSLYQ; SEQ ID NO: 31), and $CII_{261-273}$ (AGFKGEQGPKGEP; SEQ ID NO:32). GAD65 Altered Peptide Ligand (APL) that were loaded to Preiss were: M559Z (NFFRZVISNPAAT; SEQ ID NO:33), I561M (NFFRMVMSNPAAT; SEQ ID NO:34), N563Q (NFFRMVISQPAAT; SEQ ID NO:35), I561M-N563Q (NFFRMVMSQPAAT; SEQ ID NO:36). Cells ($10^6$) were incubated with 1-5 μg of specific Fab for 1 hour at 4° C., followed by incubation with mouse-anti-myc Ab and FITC-labeled anti-mouse Ab for 45 minutes at 4° C. Cells were finally washed and analyzed by a FACSCalibur flow cytometer (BD).

IL-2 Bioassay for T Cell Hybridoma

Hybridoma cells ($10^5$/well in a 96-well plate) in 50 μl of 10% FBS-containing medium were combined with 50 μl $10^5$ irradiated (3000 rad) splenocytes of HLA-DRB1*0401-Tg mice and with 50 μl of 25 μg/ml individual peptides and various Fabs concentrations. The cells were incubated at 37° C. and 7% $CO_2$ for 24 hours. Supernatants were collected from the top of the culture for IL-2 capture ELISA.

Histology

Fresh tissues were frozen in Tissue-Tek OTC compound (Sakura Finetek, Torrance, Calif. 9050) for immunofluorescence on frozen sections. Frozen sections (8 μm) were dried and blocked with 0.1% BSA/PBS for 30 minutes. G3H8 was added at 50 μg/ml for 1 hour at room temperature. Alexa-488-anti-human (A11013, Molecule probes, Eugene, Oreg., USA) was used as secondary Ab at 1:200 dilution. Fluorescence images were taken on Cell Observer—Zeiss Microscope.

Example 1

Isolation of Antibodies Specific to $DR4/GAD_{555-567}$ Complex

For the isolation of TCRLs directed to the native MHC/peptide complexes the present inventors generated a recombinant $DR4/GAD_{555-567}$ complex which was used for screening of a phage display antibody library.

Recombinant DR4 Complexes

Four-domain DR4 molecules were generated from a DR4 construct previously reported for expression in insect cells (Svendsen, P., et al., 2004) in which the intracellular domains of the DR-A1*0101 and DR-B1*0401 chains were replaced by leucine-zipper dimerization domains for heterodimer assembly (Svendsen, P., et al., 2004). The antigenic peptide was introduced to the N-terminus of the DR-B chain through a flexible linker. The Bir A recognition sequence for biotinylation was introduced to the C-terminus of the DR-A chain (FIG. 1A).

Screening of Ab Phage Display Library:

For selection of Fabs directed to DR4/GAD555-567 complex the present inventors screened a large Ab phage library, consisting of a repertoire of $3.7 \times 10^{10}$ human recombinant Fab fragments (de Haard H. J., et al., 1999). For panning, biotinylated soluble $DR4/GAD_{555-567}$ complexes were used. Fab clones with peptide-dependent, MHC class II restricted specificity were of interest and were picked for further characterization. DNA fingerprinting by BstNI restriction reaction revealed 13 different restriction patterns of GAD peptide-dependent DR4 specific Fabs, indicating the selection of several different Fabs with such a unique specificity.

Specificity of TCR-Like Fabs Toward $DR4/GAD_{555-567}$ Complexes:

The present inventors used *E. coli* cells to produce a soluble Fab form of a representative clone of each DNA restriction pattern. The specificity of the selected clones was characterized in ELISA binding assay (FIG. 2A). Four different TCRL Fab Abs (G1A1, G1H12, G3H8, G1A2) were isolated and found to bind solely to recombinant full length $DR4/GAD_{555-567}$ complexes and not to DR4 complexes with control peptides (i.e., the DR4 molecule without the $GAD_{555-567}$ peptide), or to the $GAD_{555-567}$ peptide alone. Additionally, these TCRLs successfully detect native DR4/$GAD_{555-567}$ complexes presented by EBV transformed DR4+ Priess B cell (FIG. 2B for representative G3H8 Fab). In addition, the Fabs do not bind Preiss cells loaded with control DR4-associated peptides such as $HA_{307-316}$, $InsA_{1-15}$, $CII_{261-273}$ (FIG. 2B). $GAD_{555-567}$ is the minimal stimulating peptide within the $GAD_{552-572}$ naturally processed T cell epitope of the hGAD65 in the context of DR4 (Nepom G T, et al., 2001). Therefore, the present inventors tested the ability of the isolated TCRLs to recognize this naturally T1D-associated epitope. As seen in FIG. 2C, G3H8 binds Preiss cells loaded with $GAD_{552-572}$ with the same intensity as for the cells loaded with equal molar quantity of $GAD_{555-567}$ peptide. Same binding pattern obtained for all the selected DR4/GAD TCRL Fabs (data not shown). Further support for the TCR-like specificity characteristic of G3H8 came from the dose-depended binding to the DR4/GAD complexes on APCs as obtained from titrations of Fab concentrations (FIG. 2D) and loaded $GAD_{555-567}$ peptide concentration (FIG. 2E). Increasing in the percentages of DR4/GAD complexes within the total DR4/peptide complexes on the APCs found to be correlated with increased G3H8 staining intensity. In addition, this characterization of G3H8 and other TCRLs makes them suitable for quantification studies of specific MHC/peptide complexes presented by APC of interest.

Example 2

Fine Specificity of the G3H8 Antibody

Fine Specificity of G3H8 TCRL Fabs

In order to localize the binding residues of the isolated TCRLs within the GAD peptide the present inventors tested the recognition of Preiss cells loaded with a set of hGAD65 altered peptide ligands (APL). A panel of peptides containing substitutions in the $GAD65_{555-567}$ sequence at TCR contact sites was used. Binding assays of G3H8 to DR4 complexes presenting GAD-555-567 peptides with amino acid substitutions M559Z (P3), I561M (P5), N563Q (P7), or I561M(P5)+N563Q(P7), located P5 as essential contact residue for G3H8-DR4/GAD555-567 interaction. TcR contact P5 position has been shown to be important for TcR5 interactions with this hGAD65 epitope (John A. et al., 2004), emphasizing the TCR-like nature of G3H8 Fab. As shown in FIGS. 3A-F, Preiss cells loaded with GAD555-567 containing the single amino acid substitutions M559Z (FIG. 3B) and N563Q (FIG. 3D) obtained similar binding intensity of G3H8 Fab as for Preiss cells loaded with the wild-type sequence of the GAD555-567 peptide (FIG. 3A). Contrary, Preiss cells loaded with GAD555-567 containing the single amino acid substitution I561M (FIG. 3C) and the double amino acids substitution I561M, N563Q (FIG. 3E) obtained significant decrease in the binding intensity of Fab G3H8 compared to the wild-type peptide. Thus, I561M substitution abolished the recognition of DR4/GAD555-567 complex by Fab G3H8 and highlighted position P5 as essential contact residue of G3H8 in the DR4/GAD555-567 complex. Since P5 is essential T-cell Receptor contact position of many known T cell clones specific to the DR4/GAD epitope, G3H8 potentially will able the inhibition of poly-clonal GAD-specific T cell response.

Example 3

The Isolated Antibodies of Some Embodiments of the Invention are Capable of Inhibiting GAD-Specific MHC Restricted T Cell Response Blocking of GAD-Specific DR0401 Restricted T Cell Response The present inventors further tested the ability of G3H8 Fab to compete with the cognate TcR interaction with DR4/GAD complexes presented by APCs and by that to block this activating signal leading to T cells autoreactivity. The present inventors tested if G3H8 can inhibit Ag-specific activation of T cell hybridoma in a peptide-specific HLA-restricted manner. G3H8 Fab found to inhibit ~80% response of G2.1.36.1 T cell hybridoma specific to GAD-555-567 restricted by HLA-DR*0401 (FIG. 4A). Of important, G3H8 do not inhibit H1.13.2 hybridoma response to HA307-319 peptide restricted by HLA-DR*0401 (FIG. 4B). Thus, antigen-specific immunologic tolerance to the autoreactive GAD-epitope was in-vitro demonstrated by G3H8 Fab.

Example 4

Identification of Antigen Presenting Cells which Present the GAD555-567 Peptide in Islets of Diabetic Transgenic Mice Detection of DR4/GAD555-567 Complexes in Pancreas of Diabetic B7/0401 Tg-Mice RIP-B7 mice transgenic for the DR4 subtype DRA1*0101/B1*0401 were reported to develop spontaneous diabetes (Gebe J A, et al., 2006). Age-depended loss of cellular tolerance to the $GAD_{555-567}$ epitope (identical in all mouse and human isoforms) was identified in these mice, emphasizing their utility as humanized mice model mimicking the MHC-antigen interactions of the human disease. The present inventors used the G3H8 Fab to test whether APC in the infiltrated islets of diabetic B7/DR0401 mice present the $GAD_{555-567}$ peptide on their MHC molecules. Positive staining of the G3H8 identified such complexes in islets of B7/DR4 diabetic mice (FIGS. 5A-C) and in infiltrated islets of B7/DR4 pre-diabetic mice (data not shown) as compared to islets from C57B6 control mice (FIGS. 5D-E). These results demonstrate the ability of G3H8 Fab to detect and bind infiltrating APC presenting the beta cell-derived GAD555-567 autoantigen. G3H8 Fab found to bind in a peptide-specific manner APC presenting GAD-autoantigen at the islets of langerhans of the pancreas. The demonstrated accessibility of G3H8 antibody to the islets infiltrating APC is essential for its therapeutic goal by blocking the down-stream activation of autoreactive T cells by these APC.

Example 5

Isolation of Specific MHC Class II and GAD Autoantigenic Peptide Complexes

Table 3, hereinbelow, provides a list of MHC class II restricted GAD autoantigens which can form a complex with MHC class II. Such complexes are used for isolation of specific antibodies useful for diagnostic and therapeutic purposes.

TABLE 3

| SEQ ID NO: | GAD autoantigenic peptide | MHC class II |
|---|---|---|
| 61 | VNFFRMVISNPAATHQD | DR4 |
| 62 | DKVNFFRMVISNPAATHQDID | DR4 |
| 22 | NFFRMVISNPAAT | DR4 |

Table 3: Provided are the GAD autoantigenic peptides (with their sequence identifiers, SEQ ID NO:) and the MHC class II molecules which bind thereto.

Example 6

Binding and Specificity of Whole IGG G3H8 Antibody

Experimental Results
Generation of G3H8 IgG Antibody
The G3H8 Fab was cloned into a fully human whole IgG molecule. The H and L Fab genes were cloned for expression as human IgG1 κ Ab into the eukaryotic expression vector pCMV/myc/ER. For the H chain, the multiple cloning site, the myc epitope tag, and the endoplasmic reticulum (ER) retention signal of pCMV/myc/ER were replaced by a cloning site containing recognition sites for BssHI and NheI followed by the human IgG1 constant H chain region cDNA isolated by RT-PCR from human lymphocyte total RNA. A similar construct was generated for the L chain. Each shuttle expression vector carries a different antibiotic resistance gene. Expression was facilitated by co-transfection of the two constructs into the human embryonic kidney HEK293 cell by using the FuGENE 6 Transfection Reagent (Roche). After co-transfection, cells were grown on selective medium. Clones that reacted specifically with Preiss cells pulsed with GAD-555-567 peptide were adapted to growth in 0.5% serum and were further purified using protein A affinity chromatography. SDS-PAGE analysis of the purified protein revealed homogenous, pure IgG with the expected molecular mass of 150 kDa.

Specificity of the G3H8 Antibody Towards Cells Presenting the HLA-DR4-GAD-555-567 Complexes Ex Vivo
G3H8 TCRL specificity towards GAD antigen presenting cells (APCs) was demonstrated also ex vivo by flow cytometry on inguinal (draining) lymph nodes (LNs) derived from GAD-555-567 immunized HLA-DR4 Transgenic (Tg) mice. Briefly, mice were immunized with 100 µg peptide in 100 µl 50% CFA/PBS subcutaneously at the base of the tail. Tissues were harvested on day 5 and single cell suspensions were analyzed by flow cytometry. LN cells were washed and incubated with 0.125 µg/ml G3H8 IgG for 1 hour at 4° C. followed by incubation with anti-human-PE as a secondary Ab (2.5 µg/ml).

As shown in FIGS. 10A-B (the results shown were obtained with IgG antibodies, but similar results were obtained with Fab antibodies, not shown), the G3H8 TCRL Ab specifically stained APCs in LNs derived from GAD immunized mice which included 6.5% positive cells (i.e., cells presenting the HLA-DR4-GAD-555-567 complexes) but not APCs presenting the HLA-DR4-HA-307-319 complex from mice immunized with the control HA-307-319 peptide.

G3H8 IgG Exhibits Enhanced Binding and Potency as Compared to the Fab

The G3H8 IgG form was found to exhibit enhanced binding as compared to the Fab fragment (FIG. 11A). Moreover, the whole IgG TCRL molecule, which has increased avidity, inhibited GAD-specific T cell activation/function with >10-fold higher potency compared to the Fab (FIG. 11B) while maintaining its unique TCR-like specificity (FIG. 11C).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

1. Svendsen, P., C. B. Andersen, N. Willcox, A. J. Coyle, R. Holmdahl, T. Kamradt, and L. Fugger. 2004. Tracking of Proinflammatory Collagen-Specific T Cells in Early and Late Collagen Induced Arthritis in Humanized Mice. J Immunol 173:7037-7045;
2. de Haard H. J., van Neer N., Reurs A., Hufton S. E., Roovers R. C., Henderikx P., de Bruine A. P., Arends J. W., Hoogenboom H. R. A large non-immunized human Fab fragment phage library that permits rapid isolation and kinetic analysis of high affinity antibodies. J. Biol. Chem., 274: 18218-18230, 1999;
3. Cohen C J, Denkberg G, Lev A, Epel M, Reiter Y. 2003. Recombinant antibodies with MHC-restricted, peptide-specific, T-cell receptor-like specificity: new tools to study antigen presentation and TCR-peptide-MHC interactions. Journal of Molecular Recognition 16:324-332;
4. Krogsgaard M., Wucherpfennig K W., Cannella B., et al. Visualization of Myelin Basic Protein (MBP) T Cell Epitopes in Multiple Sclerosis Lesions using a Monoclonal Antibody Specific for the Human Histocompatibility Leukocyte Antigen (HLA)-DR2-MBP 85-99 Complex. Journal of Experimental Medicine, vol. 191, pages 1395-1412, 2000.
5. Nepom G T, Lippolis J D, White F M, Masewicz S, Marto J A, Herman A, Luckey C J, Falk B, Shabanowitz J, Hunt D F, Engelhard V H, Nepom B S. Identification and modulation of a naturally processed T cell epitope from the diabetes-associated autoantigen human glutamic acid decarboxylase 65 (hGAD65). Proc Natl Acad Sci USA. 2001 Feb. 13; 98(4):1763-8;
6. John A. Gebe, Susan A. Masewicz, Sharon A. Kochik, Helena Reijonen and Gerald T. Nepom. Inhibition of altered peptide ligand-mediated antagonism of human GAD65-responsive CD4 T cells by non-antagonizable T cells. Eur. J. Immunol. 2004. 34: 3337-3345;
7. Gebe J A, Unrath K A, Falk B A, Ito K, Wen L, Daniels T L, Lernmark A, Nepom G T Clin Immunol. Age-dependent loss of tolerance to an immunodominant epitope of glutamic acid decarboxylase in diabetic-prone RIP-B7/DR4 mice. Clin immunol. 2006 December; 121 (3):294-304;
8. Masewicz, S. A., Papadopoulos, G. K., Swanson, E., Moriarity, L., Moustakas, A. K., and Nepom, G. T. Modulation of T cell response to hGAD65 peptide epitopes. Tissue Antigens, 59: 101-112, 2002.
9. Bach, J. M., Otto, H., Nepom, G. T., Jung, G., Cohen, H., Timsit, J., Boitard, C., and van Endert, P. M. High Affinity Presentation of an Autoantigenic Peptide in Type I Diabetes by an HLA Class II Protein Encoded in a Haplotype Protecting From Disease. Journal of Autoimmunity, 10: 375-386, 1997.
10. Ou, D., Jonsen, L. A., Metzger, D. L., and Tingle, A. J. CD4+ and CD8+ T-cell clones from congenital rubella syndrome patients with IDDM recognize overlapping GAD65 protein epitopes: Implications for HLA class I and II allelic linkage to disease susceptibility. Human Immunology, 60: 652-664, 1999.
11. Roep, B. O., Atkinson, M. A., van Endert, P. M., Gottlieb, P. A., Wilson, S. B., and Sachs, J. A. Autoreactive T cell Responses in Insulin-dependent (Type 1) Diabetes Mellitus. Report of the First International Workshop for Standardization of T cell assays. Journal of Autoimmunity, 13: 267-282, 1999.
12. Lohmann, T., Leslie, R. D., and Londei, M. T cell Clones to Epitopes of Glutamic Acid Decarboxylase 65 Raised from Normal Subjects and Patients with Insulin-dependent Diabetes. Journal of Autoimmunity, 9: 385-389, 1996.
13. Rharbaoui, Mayer, Granier, Bouanani, Thivolet, Pau, Orgiazzi, and Madec. T cell response pattern to glutamic acid decarboxylase 65 (GAD65) peptides of newly diagnosed type 1 diabetic patients sharing susceptible HLA haplotypes. Clinical & Experimental Immunology, 117: 30-37, 1999.
14. Reijonen, H., Novak, E. J., Kochik, S., Heninger, A., Liu, A. W., Kwok, W. W., and Nepom, G. T. Detection of GAD65-Specific T-Cells by Major Histocompatibility Complex Class II Tetramers in Type 1 Diabetic Patients and At-Risk Subjects. Diabetes, 51: 1375-1382, 2002.

15. Patel, S. D., Cope, A. P., Congia, M., Chen, T. T., Kim, E., Fugger, L., Wherrett, D., and Sonderstrup-McDevitt, G. Identification of immunodominant T cell epitopes of human glutamic acid decarboxylase 65_by using HLA-DR(alpha 1*0101,beta 1*0401) transgenic_mice. Proceedings of the National Academy of Sciences, 94: 8082-8087, 1997.

16. Oling, V., Marttila, J., Ilonen, J., Kwok, W. W., Nepom, G., Knip, M., Simell, O., and Reijonen, H. GAD65- and proinsulin-specific CD4+ T-cells detected by MHC class II tetramers in peripheral blood of type 1 diabetes patients and at-risk subjects. Journal of Autoimmunity, 25: 235-243, 2005.

What is claimed is:

1. An isolated complex comprising a major histocompatibility complex (MHC) class II HLA-DR4 and a glutamic acid decarboxylase (GAD) autoantigenic peptide, wherein said GAD autoantigenic peptide comprises a core amino acid sequence set forth by SEQ ID NO:14 (GAD556-565, FFRMVISNPA), wherein said GAD autoantigenic peptide is covalently attached at a C-terminus thereof to a linker peptide and wherein said autoantigenic peptide and said linker peptide are covalently inserted anywhere between amino acids 1-6 of an extracellular domain of a beta chain of said MHC class II HLA-DR4, wherein said linker peptide confers flexibility to said beta chain and enables folding of said GAD autoantigenic peptide within peptide-binding grooves within said MHC class II HLA-DR4.

2. The isolated complex of claim 1, wherein said GAD autoantigenic peptide is covalently inserted between the third and fourth amino acid of said extracellular domain of said beta chain of said MHC class II HLA-DR4.

3. The isolated complex of claim 1, having a structural conformation which enables isolation of an antibody which comprises an antigen binding domain capable of specifically binding to a native conformation of a complex composed of said MHC class II HLA-DR4 and said GAD autoantigenic peptide.

4. The isolated complex of claim 3, wherein said native conformation comprises the structural conformation of said complex of said GAD autoantigenic peptide and said MHC class II HLA-DR4 when presented on an antigen presenting cell (APC).

5. The isolated complex of claim 1, wherein said GAD autoantigen comprises no more than 30 amino acids.

6. The isolated complex of claim 1, wherein said GAD autoantigen is set forth by SEQ ID NO: 22 (NFFRMVISNPAAT, $GAD_{555-567}$).

7. The isolated complex of claim 3, wherein said antibody does not bind to said MHC class II HLA-DR4 in an absence of said GAD autoantigenic peptide, wherein the antibody does not bind to said GAD autoantigenic peptide in an absence of said MHC class II HLA-DR4.

8. The isolated complex of claim 1, wherein the isolated complex does not include a heterologous immunoglobulin attached thereto.

* * * * *